US008540987B2

(12) United States Patent
Azuma et al.

(10) Patent No.: US 8,540,987 B2
(45) Date of Patent: Sep. 24, 2013

(54) COMPOSITION FOR NEUTRALIZING BOTULINUS TOXIN TYPE-A, AND HUMAN ANTI-BOTULINUS TOXIN TYPE-A ANTIBODY

(75) Inventors: Masachika Azuma, Nagoya (JP); Motohide Takahashi, Musashimurayama (JP); Shunji Kozaki, Sakai (JP); Masafumi Mukamoto, Sakai (JP); Tomoko Kohda, Sakai (JP); Gene Kurosawa, Nagoya (JP); Yoshikazu Kurosawa, Nagoya (JP)

(73) Assignees: Institute for Antibodies Co., Ltd., Nagoya-shi (JP); Japan as Represented by Director-General of National Institute of Infectious Diseases, Tokyo (JP); Osaka Prefecture University Public Corporation, Sakai-shi (JP)

( * ) Notice: Subject to any disclaimer, the term of this patent is extended or adjusted under 35 U.S.C. 154(b) by 231 days.

(21) Appl. No.: 12/864,018

(22) PCT Filed: Jan. 23, 2009

(86) PCT No.: PCT/JP2009/000250
§ 371 (c)(1),
(2), (4) Date: Oct. 7, 2010

(87) PCT Pub. No.: WO2009/096162
PCT Pub. Date: Aug. 6, 2009

(65) Prior Publication Data
US 2011/0014211 A1   Jan. 20, 2011

(30) Foreign Application Priority Data

Jan. 29, 2008   (JP) ................................. 2008-017152

(51) Int. Cl.
*A61K 39/395* (2006.01)
*A61K 39/00* (2006.01)
*C07K 16/00* (2006.01)
*C12P 21/08* (2006.01)

(52) U.S. Cl.
USPC .................. 424/130.1; 424/133.1; 424/134.1; 530/387.1; 530/388.1; 530/387.2; 530/387.3

(58) Field of Classification Search
None
See application file for complete search history.

(56) References Cited

U.S. PATENT DOCUMENTS

| 2002/0155114 | A1* | 10/2002 | Marks et al. | 424/150.1 |
| 2004/0009178 | A1* | 1/2004 | Bowdish et al. | 424/164.1 |
| 2004/0175385 | A1* | 9/2004 | Marks et al. | 424/164.1 |
| 2004/0258699 | A1* | 12/2004 | Bowdish et al. | 424/184.1 |
| 2005/0042775 | A1 | 2/2005 | Pomato et al. | |
| 2009/0297452 | A1* | 12/2009 | Harakawa et al. | 424/9.2 |
| 2009/0324606 | A1* | 12/2009 | Marks et al. | 424/150.1 |
| 2010/0004139 | A1* | 1/2010 | Ramesh et al. | 506/14 |
| 2010/0166773 | A1* | 7/2010 | Marks et al. | 424/167.1 |
| 2010/0203559 | A1* | 8/2010 | Ester et al. | 435/7.92 |
| 2010/0222555 | A1* | 9/2010 | Dessain et al. | 530/387.3 |
| 2011/0014211 | A1* | 1/2011 | Azuma et al. | 424/167.1 |
| 2011/0105490 | A1* | 5/2011 | Zhang et al. | 514/230.5 |
| 2011/0200615 | A1* | 8/2011 | Marks et al. | 424/167.1 |
| 2012/0123098 | A1* | 5/2012 | Ramesh et al. | 530/387.3 |
| 2012/0225436 | A1* | 9/2012 | Fernandez-Salas et al. | 435/7.1 |

FOREIGN PATENT DOCUMENTS

| EP | 2246426 A1 * | 11/2010 |
| JP | 2006-311857 A | 11/2006 |
| WO | WO 03/076568 A2 * | 9/2003 |
| WO | WO-2005/016232 A2 | 2/2005 |
| WO | WO-2007/094754 A2 | 8/2007 |
| WO | WO 2007/094754 A2 * | 8/2007 |
| WO | WO 2009/008916 A2 * | 1/2009 |
| WO | WO 2010/014854 A2 * | 2/2010 |

OTHER PUBLICATIONS

Goschel et al, Experimental Neurology, 1997, 147:96-102.*
Hatheway et al, J. Infectious Diseases, Sep. 1984, 150/3:407-412.*
Bendig (Methods: A Companion to Methods in Enzymology 1995; 8:83- 93).*
Padlan et al. (PNAS 1989, 86:5938-5942).*
Colman P. M. (Research in Immunology, 145:33-36, 1994).*
Rudikoff et al (Proc. Natl. Acad. Sci. USA, 79(6):1979-1983, Mar. 1982).*
(Paul, Fundamental Immunology, 3rd Edition, 1993, pp. 292-295.*
Mullaney et al, Infection and Immunity, Oct. 2001, 69/10:6511-6514.*
Rusnak et al, Human Vaccines 5:12, 794-805; Dec. 2009.*
National Institute of Allergy and Infectious Diseases, "Summary of the Niaid Expert Panel on Botulinum Toxins," Nov. 20, 2002, 10 pages.
Supplementary European Search Report dated Jul. 8, 2011, issued for the corresponding European patent application No. 09706257.4.
Sugiyama, "*Clostridium botulinum* Neurotoxin," *Microbiol. Rev.* vol. 44, No. 3, Sep. 1980, pp. 419-448.
Arnon et al., "Infant Botulism: Epidemiology and Relation to Sudden Infact Death Syndrome," *Epidemiol. Rev.*, vol. 3, 1981, pp. 45-67.
Tacket et al., "Equine Antitoxin Use and Other Factors That Predict Outcome in Type A Foodborne Botulism," Am. J. Med., vol. 76, May 1984, pp. 794-799.
Amersdorfer et al., "Molecular characterization of murine humoral immune response to botulinum neurotoxin type a binding domain as assessed by using phage antibody libraries," *Infect. Immun.*, 65(9), 1997, pp. 3743-3752.

(Continued)

*Primary Examiner* — Nita M Minnifield
(74) *Attorney, Agent, or Firm* — Edwards Wildman Palmer LLP; James E. Armstrong, IV; Edmund J. Koundakjian

(57) ABSTRACT

Provided herein is a means which is effective for botulism diseases and the prevention of the botulism diseases. Specifically provided is a plurality of human anti-botulinum toxin type-A antibodies having different epitopes from one another. Also specifically provided is a composition for neutralizing botulinum toxin type-A, which comprises a combination of two or more of the antibodies and which has a high neutralizing activity.

13 Claims, 32 Drawing Sheets

(56) References Cited

OTHER PUBLICATIONS

Amersdorfer et al., "Genetic and immunological comparison of anti-botulinum type A antibodies from immune and non-immune human phage libraries," *Vaccine* 20, 2002, pp. 1640-1648.

Nowakowski et al, "Potent neutralization of botulinum neurotoxin by recombinant oligoclonal antibody," *Proc. Natl. Acad. Sci. USA* vol. 99, No. 17, 2002, pp. 11346-11350.

Takahashi, "Kouseiroudoukagakukenkyu kenkyu-hi hojokin soukatsu kennkyu houkokusyo" 2006, pp. 21-23.

Takahashi, "Kouseiroudoukagakukenkyu kenkyu-hi hojokin soukatsu kennkyu houkokusyo" 2005, pp. 1-7.

Takahashi, "Kouseiroudoukagakukenkyu kenkyu-hi hojokin soukatsu kennkyu houkokusyo" 2005, pp. 23-26.

Takahashi, "Kouseiroudoukagakukenkyu kenkyu-hi hojokin soukatsu kennkyu houkokusyo" 2008, pp. 15-20.

H. Sugiyama, "*Clostridium botulinum* Neurotoxin," Microbiol. Rev. vol. 44, No. 3, Sep. 1980, pp. 419-448.

S. Arnon et al., "Infant Botulism: Epidemiology and Relation to Sudden Infact Death Syndrome," Epidemiol. Rev., vol. 3, 1981, pp. 45-67.

C. O. Tacket et al., "Equine Antitoxin Use and Other Factors That Predict Outcome in Type A Foodborne Botulism," Am. J. Med., vol. 76, May 1984, pp. 794-799.

P. Amersdorfer et al., "Molecular characterization of murine humoral immune response to botulinum neurotoxin type A binding domain as assessed by using phage antibody libraries," Infect. Immun., 65(9), 1997, pp. 3743-3752.

P. Amersdorfer et al., "Genetic and immunological comparison of anti-botulinum type A antibodies from immune and non-immune human phage libraries," Vaccine 20, 2002, pp. 1640-1648.

A. Nowakowski et al., "Potent neutralization of botulinum neurotoxin by recombinant oligoclonal antibody," Proc. Natl. Acad. Sci. USA vol. 99, No. 17, 2002, pp. 11346-11350.

M Takahashi, "Kouseiroudoukagakukenkyu kenkyu-hi hojokin soukatsu kennkyu houkokusyo, " 2006, pp. 21-23.

M Takahashi, "Kouseiroudoukagakukenkyu kenkyu-hi hojokin soukatsu kennkyu houkokusyo, " 2005, pp. 1-7.

M Takahashi, "Kouseiroudoukagakukenkyu kenkyu-hi hojokin soukatsu kennkyu houkokusyo," 2005, pp. 23-26.

M Takahashi, "Kouseiroudoukagakukenkyu kenkyu-hi hojokin soukatsu kennkyu houkokusyo," 2008, pp. 15-20.

International Search Report dated Feb. 24, 2009, issued for PCT/JP2009/000250.

\* cited by examiner

Fig. 3

| | IU/ml | | Antitoxin | Toxin | 0.2 ml Subcutaneous inoculation | | | | | |
|---|---|---|---|---|---|---|---|---|---|---|
| Standard antitoxin type-A | | | | 500-Fold dilution of test toxin | After one day (11.15) | | After two days (11.16) | | After three days (11.17) | |
| Japanese standard antitoxin | 1-Fold | | 0.25 | 0.25 | − | − | − | − | − | − |
| | 3-Fold dilution | 0.25 | 0.125 | 0.25 | − | − | − | − | − | − |
| | 9-Fold dilution | 0.25 | 0.125 | 0.25 | − | − | − | − | − | − |
| | 27-Fold dilution | 0.25 | 0.125 | 0.25 | − | − | − | − | − | − |
| | 81-Fold dilution | 0.25 | 0.125 | 0.25 | − | ± | − | ± | − | − |
| | | 0.25 | 0.125 | 0.25 | + | ± | + | + | + | + |
| | | 0.125 discard | | 0.25 | + | + | + | + | + | + |
| Sample | 3.0× inter | PBS | Antibody | | | | | | | |
| BT-015 | 5-Fold dilution | | 0.25 | 0.25 | − | − | − | − | − | − |
| | 15-Fold dilution | 0.25 | 0.125 | 0.25 | − | − | − | − | − | − |
| | 45-Fold dilution | 0.25 | 0.125 | 0.25 | − | − | − | − | − | − |
| | 135-Fold dilution | 0.25 | 0.125 | 0.25 | − | − | − | − | − | − |
| | 405-Fold dilution | 0.25 | 0.125 | 0.25 | − | ± | − | − | − | − |
| | | 0.125 discard | | 0.25 | | | | | | |
| BT-037 | 5-Fold dilution | | 0.25 | 0.25 | + | + | + | + | + | + |
| | 15-Fold dilution | 0.25 | 0.125 | 0.25 | + | + | + | + | + | + |
| | 45-Fold dilution | 0.25 | 0.125 | 0.25 | + | + | + | + | + | + |
| | 135-Fold dilution | 0.25 | 0.125 | 0.25 | + | + | + | + | + | + |
| | 405-Fold dilution | 0.25 | 0.125 | 0.25 | + | + | ++ | ++ | ++ | ++ |
| | | 0.125 discard | | 0.25 | | | | | | |
| BT-039 | 5-Fold dilution | | 0.25 | 0.25 | ± | + | − | + | − | + |
| | 15-Fold dilution | 0.25 | 0.125 | 0.25 | + | + | + | ++ | + | ++ |
| | 45-Fold dilution | 0.25 | 0.125 | 0.25 | + | + | + | ++ | + | ++ |
| | 135-Fold dilution | 0.25 | 0.125 | 0.25 | + | + | + | + | + | + |
| | 405-Fold dilution | 0.25 | 0.125 | 0.25 | + | + | + | + | + | + |
| | | 0.125 discard | | 0.25 | | | | | | |
| BT-044 | 5-Fold dilution | | 0.25 | 0.25 | + | + | + | + | + | + |
| | 15-Fold dilution | 0.25 | 0.125 | 0.25 | + | + | + | + | + | + |
| | 45-Fold dilution | 0.25 | 0.125 | 0.25 | + | + | ++ | + | + | + |
| | 135-Fold dilution | 0.25 | 0.125 | 0.25 | + | + | ++ | + | ++ | + |
| | 405-Fold dilution | 0.25 | 0.125 | 0.25 | + | + | + | + | + | + |

| Sample | | | | | | | | | | | Discontinued |
|---|---|---|---|---|---|---|---|---|---|---|---|
| | IU/ml | | PBS | AT | Tn | | Ratio | | | | |
| Standard antitoxin type-A | | | | | 10 x stock Tn | body weight | Day 1 | | Day 2 | Day 3 | Day 4 |
| | | | | | | | AM | PM | PM | AM | AM |
| Sample | No. | | PBS | volume | Tn | | | | | | |
| 1 | 139 | 1x | | 0.25 | 0.25 | | ++, ++ | d, d | | | |
| 2 | 140 | 1x | | 0.25 | 0.25 | | ++, ++ | ++, ++ | d, +++ | d | |
| 3 | 141 | 1x | | 0.25 | 0.25 | | d, d | | | | |
| 4 | 142 | 1x | | 0.25 | 0.25 | | ++, ++ | ++, d | d | | |
| 5 | 144 | 1x | | 0.25 | 0.25 | | +++, +++ | d, d | | | |
| 6 | 148 | 1x | | 0.25 | 0.25 | | d, +++ | d | | | |
| 7 | 153 | 1x | | 0.25 | 0.25 | | +++, +++ | d, d | | | |
| 8 | 155 | 1x | | 0.25 | 0.25 | | d, +++ | d | | | |
| 9 | 156 | 1x | | 0.25 | 0.25 | | +++, +++ | d, d | | | |
| 10 | 165 | 1x | | 0.25 | 0.25 | | +++, +++ | d, d | | | |
| 11 | 175 | 1x | | 0.25 | 0.25 | | ++, ++ | +++, +++ | +++, +++ | +++, +++ | +++, +++ |
| 12 | 178 | 1x | | 0.25 | 0.25 | | +++, +++ | d, d | | | |
| 13 | 180 | 1x | | 0.25 | 0.25 | | d, d | | | | |
| 14 | 182 | 1x | | 0.25 | 0.25 | | +++, +++ | d, d | | | |
| 15 | 184 | 1x | | 0.25 | 0.25 | | +++, +++ | +++, +++ | d, d | | |
| 16 | 198 | 1x | | 0.25 | 0.25 | | d, d | | | | |
| 17 | 202 | 1x | | 0.25 | 0.25 | | d, +++ | d | | | |
| 18 | 203 | 1x | | 0.25 | 0.25 | | d, d | | | | |
| 19 | 208 | 1x | | 0.25 | 0.25 | | ++, ++ | +++, +++ | d, d | | |
| 20 | 218 | 1x | | 0.25 | 0.25 | | +++, d | d | | | |
| 21 | 219 | 1x | | 0.25 | 0.25 | | ++, ++ | d, d | | | |
| 22 | 222 | 1x | | 0.25 | 0.25 | | ++, d | d | | | |
| 23 | 225 | 1x | | 0.25 | 0.25 | | +++, +++ | +++, +++ | d, d | | |
| 24 | 230 | 1x | | 0.25 | 0.25 | | +++, +++ | d, d | | | |
| 25 | 231 | 1x | | 0.25 | 0.25 | | +++, +++ | d, d | | | |
| 26 | 232 | 1x | | 0.25 | 0.25 | | +++, ++ | d, d | | | |
| 27 | MIX | 1x | | 0.25 | 0.25 | | d, +++ | d | | | |

Fig. 9

|  | Number of introduced phages | Number of collected phages | Number of clones tested by ELIZA | Neutralizing antibody |  |
|---|---|---|---|---|---|
| 1st | $1.0 \times 10^{13}$ | $9.36 \times 10^{7}$ |  |  |  |
| 2nd | $3.64 \times 10^{13}$ | $4.98 \times 10^{7}$ |  |  |  |
| 3rd | $3.60 \times 10^{13}$ | $6.22 \times 10^{8}$ | 1-46 | BT-015 | Screening experiment 1 |
| 4th | $1.56 \times 10^{13}$ | $9.6 \times 10^{8}$ | 47-92 |  | Screening experiment 2 |
| 3rd -2 | $3.60 \times 10^{13}$ | $4.72 \times 10^{7}$ | 93-138 |  | Screening experiment 3 |
| 4th -2 | $7.24 \times 10^{12}$ | $7.52 \times 10^{8}$ | 139-232 | BT-175 | Screening experiment 4 |

| | Number of introduced phages | Number of collected phages | Number of clones tested by ELIZA | Neutralizing antibody | |
|---|---|---|---|---|---|
| 1st | $1.0 \times 10^{13}$ | $2.34 \times 10^{8}$ | | | |
| 2nd | $2.60 \times 10^{13}$ | $9.68 \times 10^{7}$ | | | |
| 3rd | $4.56 \times 10^{13}$ | $1.6 \times 10^{8}$ | NT001-096 | | |
| | | | NT101-195 | | |
| 4th | $2.64 \times 10^{13}$ | $1.58 \times 10^{8}$ | NT201-296 | NT-221 | Screening experiment 5 |
| | | | NT301-392 | NT-320 | |
| 4th-2 | $1.98 \times 10^{13}$ | $3.59 \times 10^{7}$ | NT401-496 | | Screening experiment 6 |
| | | | NT501-596 | NT-523,NT-539 | |

Antigen: neurotoxin

Fig. 16

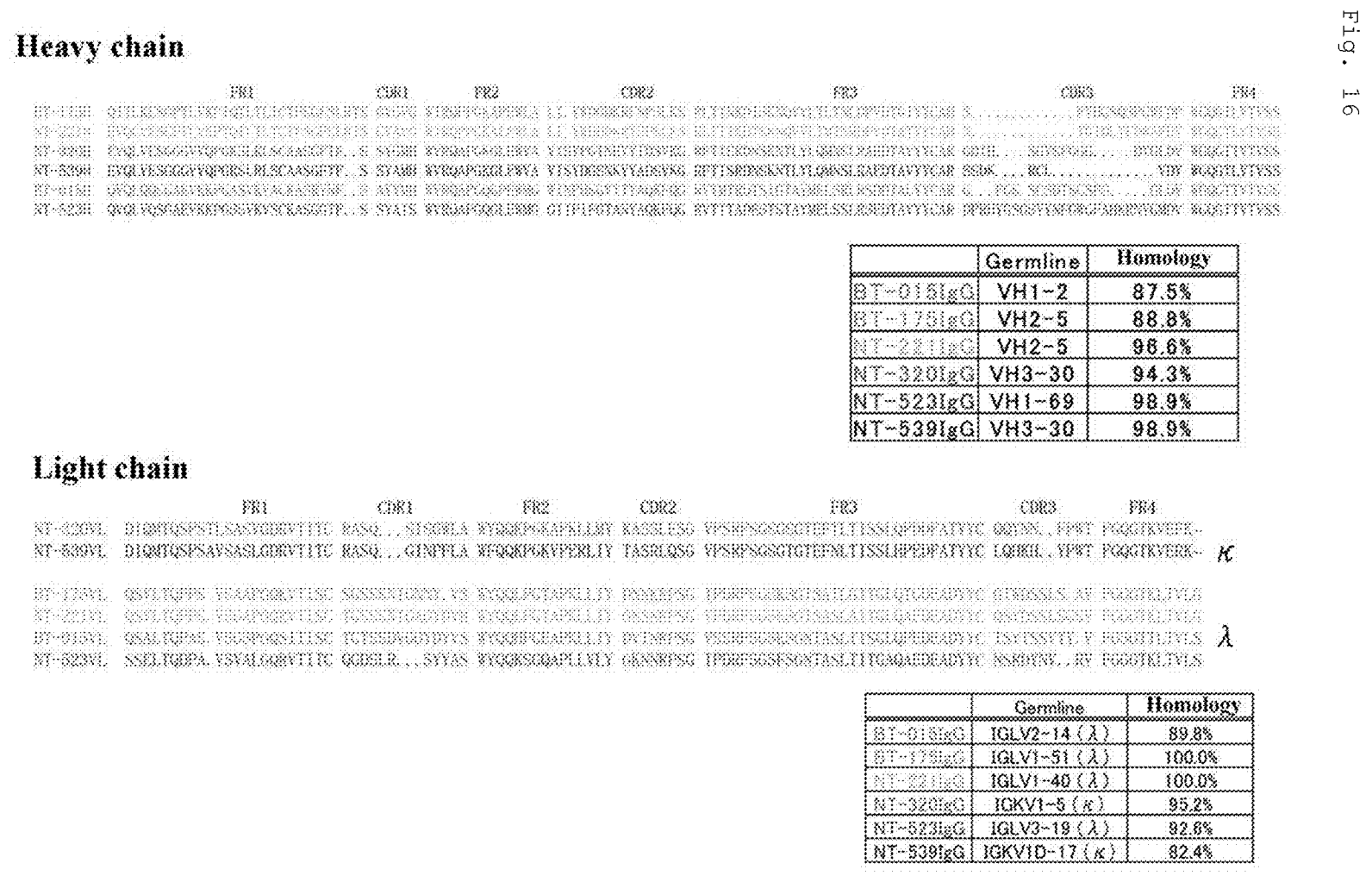

Heavy chain

| Germline | Homology |
|---|---|
| NT-018IgG | VH1-2 | 87.5% |
| NT-179IgG | VH2-5 | 88.8% |
| NT-211IgG | VH2-5 | 96.6% |
| NT-320IgG | VH3-30 | 94.3% |
| NT-523IgG | VH1-69 | 98.9% |
| NT-539IgG | VH3-30 | 98.9% |

Light chain

| Germline | Homology |
|---|---|
| NT-018IgG | IGLV2-14 (λ) | 89.8% |
| NT-179IgG | IGLV1-51 (λ) | 100.0% |
| NT-211IgG | IGLV1-40 (λ) | 100.0% |
| NT-320IgG | IGKV1-5 (κ) | 95.2% |
| NT-523IgG | IGLV3-19 (λ) | 92.8% |
| NT-539IgG | IGKV1D-17 (κ) | 82.4% |

Antibody : BT-015

| Antigen | Concentration of antibody (ug/ml) 1 | 0.5 | 0.25 | 0.125 |
|---|---|---|---|---|
| BoNT/A1 | >3.500 | >3.500 | 3.149 | 2.491 |
| H chain | 0.071 | 0.064 | 0.050 | 0.045 |
| L chain | 0.100 | 0.087 | 0.082 | 0.079 |
| BoNT/A2 | >3.500 | >3.500 | >3.500 | ND |

Antibody : NT-320

| Antigen | Concentration of antibody (ug/ml) 10 | 5 | 2.5 | 1.25 |
|---|---|---|---|---|
| BoNT/A1 | 2.620 | 2.475 | 2.464 | 2.250 |
| H chain | 1.059 | 1.062 | 1.065 | 1.000 |
| L chain | 0.197 | 0.097 | 0.082 | 0.034 |
| BoNT/A2 | 1.121 | 0.867 | 0.389 | ND |

Antibody : BT-175

| Antigen | Concentration of antibody (ug/ml) 1 | 0.5 | 0.25 | 0.125 |
|---|---|---|---|---|
| BoNT/A1 | >3.500 | >3.500 | >3.500 | 3.004 |
| H chain | 0.078 | 0.052 | 0.037 | 0.029 |
| L chain | 0.194 | 0.153 | 0.115 | 0.076 |
| BoNT/A2 | >3.500 | >3.500 | >3.500 | ND |

Antibody : NT-523

| Antigen | Concentration of antibody (ug/ml) 10 | 5 | 2.5 | 1.25 |
|---|---|---|---|---|
| BoNT/A1 | >3.500 | >3.500 | >3.500 | >3.500 |
| H chain | 1.828 | 1.752 | 1.598 | 1.498 |
| L chain | 2.656 | 2.212 | 1.947 | 1.398 |
| BoNT/A2 | 0.949 | 0.945 | 0.871 | ND |

Antibody : NT-221

| Antigen | Concentration of antibody (ug/ml) 1 | 0.5 | 0.25 | 0.125 |
|---|---|---|---|---|
| BoNT/A1 | >3.500 | >3.500 | 2.918 | 2.102 |
| H chain | 0.104 | 0.079 | 0.054 | 0.042 |
| L chain | 0.131 | 0.096 | 0.088 | 0.071 |
| BoNT/A2 | 1.133 | 1.105 | 0.893 | ND |

Antibody : NT-539

| Antigen | Concentration of antibody (ug/ml) 10 | 5 | 2.5 | 1.25 |
|---|---|---|---|---|
| BoNT/A1 | 2.360 | 1.909 | 1.505 | 1.202 |
| H chain | 0.261 | 0.206 | 0.114 | 0.083 |
| L chain | 0.314 | 0.209 | 0.102 | 0.094 |
| BoNT/A2 | 2.065 | 1.272 | 0.646 | ND |

Fig. 30

1) A1 Neurotoxin (NT)

2) Recombinant Hc

Fig. 32

|  | BT-015 | BT-175 | NT-221 | NT-320 | NT-523 | NT-539 |
|---|---|---|---|---|---|---|
| ELISA | NT | NT | NT | H | NT | NT |
| Blotting | – | – | – | – | Hc | – |
| Immunoprecipitation | H | L(?) | NT | NT | H | H |
| Epitope candidate | H | L(?) | – | H | Hc | H |

COMPOSITION FOR NEUTRALIZING BOTULINUS TOXIN TYPE-A, AND HUMAN ANTI-BOTULINUS TOXIN TYPE-A ANTIBODY

CROSS-REFERENCE TO RELATED APPLICATIONS

This application is the U.S. national phase, pursuant to 35 U.S.C. §371, of PCT international application Ser. No. PCT/JP2009/000250, filed Jan. 23, 2009, designating the United States and published in Japanese on Aug. 6, 2009 as publication WO2009/096162. PCT/JP2009/000250 claims priority to Japanese Patent Application Ser. No. 2008-017152, filed Jan. 29, 2008. The entire contents of the aforementioned patent applications are incorporated herein by reference.

TECHNICAL FIELD

The present invention relates to a genetically recombinant antibody having a binding activity to botulinum toxin type-A and having a fully human variable region; a nucleic acid molecule encoding the antibody; a transformant producing the antibody; a method for producing an antibody using the transformant; a composition for neutralizing botulinum toxin type-A using the antibody; and the like.

BACKGROUND ART

Toxins produced by *Clostridium botulinum* are classified into types A to G depending on the difference in serotypes. The toxin types A, B, E, and F have a serious influence on the human health. There are four kinds of botulinum diseases in humans, such as "foodborne botulism (botulinum food poisoning)", "infant botulism", "wound botulism" and "infectious botulism". The toxin type-A is involved in 26% of botulinum food poisoning. The toxin type-A is involved in 26% of botulinum food poisoning. The toxin types B and E are followed by this, and toxin type-F is relatively low in the ratio involved in botulinum food poisoning. In addition, it is reported that wound botulism is caused only by toxin type-A or type-B (Non-Patent Document 1).

Food poisoning botulism in adults is usually developed by oral intake of toxins produced as a result of the growth of bacteria and spores in food, while in the case of infant botulism, symptoms of poisoning are caused by the bacterial growth and proliferation leading to toxin production in the intestinal tract as a result of oral intake of bacteria and spores in food such as honey and the like. Although toxins that cause food poisoning differ somewhat depending on countries, cases caused by toxin types A, B, and E have been reported. Moreover, the majority of the infant botulisms are type-A and type B, but toxin types E and F by *C. butiricum* also have been reported.

Botulinum toxin is a molecule having a structure in which an S—S bond (disulfide bond) is formed between the heavy chain and the light chain. The botulinum toxin blocks the neurotransmission to muscles, causing hereby flaccid paralysis. When botulinum toxin comes into the respiratory tract or respiratory muscle, fatal breathing disorder will be caused. The mortality rate by the botulinum toxin is 12%, and it becomes higher in a specific risk group (Non-Patent Document 3).

On the other hand, since the botulinum toxin is the most fatal toxin as a biological toxin (the fatal dose of the purified toxin type-A in a human of 70 kg is 0.09-0.15 µg (i.v. or i.m.), 0.70-0.90 µg (inhalation), and 70 µg (even oral) (JAMA. 2001 Feb. 28; 285(8):1059-70)), such a botulinum toxin possesses a particularity such as an applicability to the bioterrorism as an another aspect other than usual poisoning. Therefore, a social attention has been paid to it.

The neutralizing agent for botulinum toxins, approved in Japan, is a preparation using an equine serum as a raw material. This preparation may have a danger to cause an immunoreaction such as anaphylactic reaction, etc. because it contains, as a main component, globulin derived from equine serum, i.e. a heterologous protein to humans. In addition, there are problems of unknown viral infections and serum diseases in the preparation. Furthermore, stable supply of this preparation is also difficult. Besides, since one year or more are needed for the production of the preparations, emergency response to bioterrorism and the like is in a difficult situation. In addition, this preparation is not suitable for a storage purpose because there is a problem in the management of horse rearing.

As for infant botulism, it is a current state that treatment with this equine globulin preparation has not been employed because of avoidance of serious side effects such as anaphylactic reactions and the like. In the United States of America, a specific treatment for the infant botulism is performed with use of a human globulin preparation prepared from the plasma having a high neutralizing antibody titer obtained by immunizing a healthy person with a botulinum toxin. Actually, in the United States of America, the drug under the brand name called BabyBIG® for the infant botulism has been granted orphan drug designation for its marketing by FDA. However, this method holds problems of raw material availability and biohazard issues in addition to ethical issues, as well as problems of various virus inspections to be needed from the viewpoint of safe security necessary in the production. In addition, the preparation has not yet been approved in Japan and cannot be used.

It was reported to have succeeded in producing a recombinant neutralizing chimeric antibody against toxin type-A (Patent Document 1). However, it is necessary to solve the problems such as appearance of HACA (human anti-chimeric antibody) or anaphylactic reactions when the antibody is used.

Meanwhile, a research and development for toxin neutralization have been performed from the viewpoint of preparing for particularly bioterrorism threats in the United States of America, and a method of producing a phage antibody library from human B lymphocytes obtained by immunization with a botulinum toxin pentamer and selecting a desired full length human neutralizing antibody from the library was undertaken. However, such a method has not succeeded in obtaining an antibody clone that exerts a sufficient neutralizing activity against the toxin type-A alone. Therefore, it could not but enhance the neutralizing activity by mixing (oligo cloning) one kind of human antibody obtained as a result of phage display screening, with one kind of clone derived from XENO mice and further a humanized mouse antibody obtained by immunization in mice. Accordingly, intended purpose, that is, neutralization of the toxin with the full length human neutralizing antibody has not been achieved (Patent Documents 2 and 3, and Non-Patent Documents 4, 5, and 6).

Patent Document 1: Japanese Patent Laid-Open Publication No. 2006-311857
Patent Document 2: PCT WO 2005/016232 Pamphlet
Patent Document 3: PCT WO 2007/094754 Pamphlet
Non-Patent Document 1: H. Sugiyama, Microbiol. Rev. 44:419, 1980
Non-Patent Document 2: S. Arnon, Epidemiol. Rev. 3:45, 1981

Non-Patent Document 3: C. O. Tacket et al., Am. J. Med. 76:794, 1984

Non-Patent Document 4: P. Amersdorfer et al., Infect. Immun. 65(9):3743, 1997

Non-Patent Document 5: P. Amersdorfer et al., Vaccine 20: 1640, 2002

Non-Patent Document 6: Nowakowski et al., Proc. Natl. Acad. Sci. USA 99(17):11346, 2002

DISCLOSURE OF THE INVENTION

Problems to be Solved by the Invention

The present invention provides a composition useful for neutralizing botulinum toxin type-A in view of the above-mentioned background and is intended to solve various problems (anaphylactic reactions and contaminations with heterologous proteins or viruses) in conventional technologies. In addition, in view of the situation that it is difficult to objectively evaluate a neutralizing activity by the previous recombination antibody assay, a technical problem as another aspect of the present invention also resides in showing a neutralizing activity in terms of values adapted to an international standard when the composition for neutralizing botulinum toxin type-A is provided.

Means to Solve the Problems

The present inventors, at first, constructed a human phage antibody library according to a precedent, and tried to isolate an antibody clone that specifically recognizes botulinum toxin type-A. When a screening had been repeatedly performed, it was found that antibodies having each the common epitope were repeatedly selected though the plurality of antibody clones was obtained by the screening each time. As a result of having examined the cause that this phenomenon has occurred, it was expected that an epitope having an extremely high antigenicity would be present, causing the overlap of the epitope. According to this supposition, blocking of the epitope becomes an effective means for acquiring an antibody having a different epitope effectively. The present inventors planed a strategy of reacting the botulinum toxin type-A with a phage antibody library after the epitope with a strong antigenicity had been blocked (masked) by adding antibody fragments obtained redundantly through two or more screening tests. The present inventors succeeded in acquiring the plurality of antibody clones having each a different epitope by screening again according to the strategy. As a result of having analyzed the epitope of each antibody that had been successfully obtained, these antibodies were classified into four kinds by an epitope difference. In other words, it was found that specific antibody clones with regards to four epitopes were successfully obtained.

Next, neutralizing activity of combinations of three or four antibodies was compared and evaluated according to the international standard (The Japanese Pharmacopoeia; according to the clause 3.2.7 "titer test" of "freeze-dried botulism antitoxin, equine" (freeze-dried botulinum antitoxin) described in biological products listed in each monograph on drugs). As a result, the combination of three kinds of antibody clones was found as a combination of antibody clones giving a high neutralizing activity. In addition, it was shown that the neutralizing activity was improved if one more kind of antibody clone was further combined.

As mentioned above, the present inventors have succeeded in the acquisition of two or more antibody clones that brought a high neutralizing activity against botulinum toxin type-A, and clarified the relation between four epitopes recognized by the antibodies and neutralizing activities. This invention is primarily based on these findings and is as follows.

[1] A composition for neutralizing botulinum toxin type-A comprising:

a first human anti-botulinum toxin type-A antibody that recognizes an epitope of an antibody having a heavy chain variable region comprising an amino acid sequence of SEQ ID NO: 4 and a light chain variable region comprising an amino acid sequence of SEQ ID NO: 8, a second human anti-botulinum toxin type-A antibody that recognizes an epitope of an antibody having a heavy chain variable region comprising an amino acid sequence of SEQ ID NO: 36 and a light chain variable region comprising an amino acid sequence of SEQ ID NO: 40, and a third human anti-botulinum toxin type-A antibody that recognizes an epitope of an antibody having a heavy chain variable region comprising an amino acid sequence of SEQ ID NO: 44 and a light chain variable region comprising an amino acid sequence of SEQ ID NO: 48, or an epitope of an antibody having a heavy chain variable region comprising an amino acid sequence of SEQ ID NO: 52 and a light chain variable region comprising an amino acid sequence of SEQ ID NO: 56.

[2] The composition for neutralizing botulinum toxin type-A according to the above item [1], wherein:

the first human anti-botulinum toxin type-A antibody is any one of antibodies selected from the group consisting of the followings (1) to (3);

the second human anti-botulinum toxin type-A antibody is an antibody of the following (4) or (5); and the third human anti-botulinum toxin type-A antibody is any one of antibodies selected from the group consisting of the followings (6) to (8):

(1) an antibody having a heavy chain complementarity-determining region 1 comprising an amino acid sequence of SEQ ID NO: 1, a heavy chain complementarity-determining region 2 comprising an amino acid sequence of SEQ ID NO: 2, a heavy chain complementarity-determining region 3 comprising an amino acid sequence of SEQ ID NO: 3, a light chain complementarity-determining region 1 comprising an amino acid sequence of SEQ ID NO: 5, a light chain complementarity-determining region 2 comprising an amino acid sequence of SEQ ID NO: 6, and a light chain complementarity-determining region 3 comprising an amino acid sequence of SEQ ID NO: 7;

(2) an antibody having a heavy chain complementarity-determining region 1 comprising an amino acid sequence of SEQ ID NO: 9, a heavy chain complementarity-determining region 2 comprising an amino acid sequence of SEQ ID NO: 10, a heavy chain complementarity-determining region 3 comprising an amino acid sequence of SEQ ID NO: 11, a light chain complementarity-determining region 1 comprising an amino acid sequence of SEQ ID NO: 13, a light chain complementarity-determining region 2 comprising an amino acid sequence of SEQ ID NO: 14, and a light chain complementarity-determining region 3 comprising an amino acid sequence of SEQ ID NO: 15;

(3) an antibody having a heavy chain complementarity-determining region 1 comprising an amino acid sequence of SEQ ID NO: 17, a heavy chain complementarity-determining region 2 comprising an amino acid sequence of SEQ ID NO: 18, a heavy chain complementarity-determining region 3 comprising an amino acid sequence of SEQ ID NO: 19, a light chain complementarity-determining region 1 comprising an amino acid sequence of SEQ ID NO: 21, a light chain complementarity-determining region 2 comprising an amino acid sequence of SEQ ID NO: 22, and a light chain complementarity-determining region 3 comprising an amino acid sequence of SEQ ID NO: 23;

(4) an antibody having a heavy chain complementarity-determining region 1 comprising an amino acid sequence of SEQ ID NO: 25, a heavy chain complementarity-determining region 2 comprising an amino acid sequence of SEQ ID NO: 26, a heavy chain complementarity-determining region 3 comprising an amino acid sequence of SEQ ID NO: 27, a light chain complementarity-determining region 1 comprising an amino acid sequence of SEQ ID NO: 29, a light chain complementarity-determining region 2 comprising an amino acid sequence of SEQ ID NO: 30, and a light chain complementarity-determining region 3 comprising an amino acid sequence of SEQ ID NO: 31;

(5) an antibody having a heavy chain complementarity-determining region 1 comprising an amino acid sequence of SEQ ID NO: 33, a heavy chain complementarity-determining region 2 comprising an amino acid sequence of SEQ ID NO: 34, a heavy chain complementarity-determining region 3 comprising an amino acid sequence of SEQ ID NO: 35, a light chain complementarity-determining region 1 comprising an amino acid sequence of SEQ ID NO: 37, a light chain complementarity-determining region 2 comprising an amino acid sequence of SEQ ID NO: 38, and a light chain complementarity-determining region 3 comprising an amino acid sequence of SEQ ID NO: 39;

(6) an antibody having a heavy chain complementarity-determining region 1 comprising an amino acid sequence of SEQ ID NO: 41, a heavy chain complementarity-determining region 2 comprising an amino acid sequence of SEQ ID NO: 42, a heavy chain complementarity-determining region 3 comprising an amino acid sequence of SEQ ID NO: 43, a light chain complementarity-determining region 1 comprising an amino acid sequence of SEQ ID NO: 45, a light chain complementarity-determining region 2 comprising an amino acid sequence of SEQ ID NO: 46, and a light chain complementarity-determining region 3 comprising an amino acid sequence of SEQ ID NO: 47;

(7) an antibody having a heavy chain complementarity-determining region 1 comprising an amino acid sequence of SEQ ID NO: 49, a heavy chain complementarity-determining region 2 comprising an amino acid sequence of SEQ ID NO: 50, a heavy chain complementarity-determining region 3 comprising an amino acid sequence of SEQ ID NO: 51, a light chain complementarity-determining region 1 comprising an amino acid sequence of SEQ ID NO: 53, a light chain complementarity-determining region 2 comprising an amino acid sequence of SEQ ID NO: 54, and a light chain complementarity-determining region 3 comprising an amino acid sequence of SEQ ID NO: 55; and (8) an antibody having a heavy chain complementarity-determining region 1 comprising an amino acid sequence of SEQ ID NO: 57, a heavy chain complementarity-determining region 2 comprising an amino acid sequence of SEQ ID NO: 58, a heavy chain complementarity-determining region 3 comprising an amino acid sequence of SEQ ID NO: 59; a light chain complementarity-determining region 1 comprising an amino acid sequence of SEQ ID NO: 61, a light chain complementarity-determining region 2 comprising an amino acid sequence of SEQ ID NO: 62, and a light chain complementarity-determining region 3 comprising an amino acid sequence of SEQ ID NO: 63.

[3] The composition for neutralizing botulinum toxin type-A according to the above item [2], wherein:
the first human anti-botulinum toxin type-A antibody is any one of antibodies selected from the group consisting of the above-mentioned (1) to (3);
the second human anti-botulinum toxin type-A antibody is the above-mentioned antibody (4) or (5);
the third human anti-botulinum toxin type-A antibody is the above-mentioned antibody (6); and
the above-mentioned antibody (7) or (8) is further included as a fourth human anti-botulinum toxin type-A antibody.

[4] The composition for neutralizing botulinum toxin type-A according to the above item [2], wherein:
the first human anti-botulinum toxin type-A antibody is the above-mentioned antibody (1);
the second human anti-botulinum toxin type-A antibody is the above-mentioned antibody (5); and
the third human anti-botulinum toxin type-A antibody is the above-mentioned antibody (6).

[5] The composition for neutralizing botulinum toxin type-A according to the above item [4], wherein the above-mentioned antibody (7) is further included as a fourth human anti-botulinum toxin type-A antibody.

[6] The composition for neutralizing botulinum toxin type-A according to the above item [2], wherein:
the first human anti-botulinum toxin type-A antibody is the above-mentioned antibody (1);
the second human anti-botulinum toxin type-A antibody is the above-mentioned antibody (5); and
the third human anti-botulinum toxin type-A antibody is the above-mentioned antibody (7).

[7] The composition for neutralizing botulinum toxin type-A according to the above item [6], wherein the above-mentioned antibody (4) is further included as a fourth human anti-botulinum toxin type-A antibody.

[8] The composition for neutralizing botulinum toxin type-A according to any one of the above items [2] to [7], wherein:
the above-mentioned antibody (1) has a heavy chain variable region comprising an amino acid sequence of SEQ ID NO: 4 and a light chain variable region comprising an amino acid sequence of SEQ ID NO: 8;
the above-mentioned antibody (2) has a heavy chain variable region comprising an amino acid sequence of SEQ ID NO: 12 and a light chain variable region comprising an amino acid sequence of SEQ ID NO: 16;
the above-mentioned antibody (3) has a heavy chain variable region comprising an amino acid sequence of SEQ ID NO: 20 and a light chain variable region comprising an amino acid sequence of SEQ ID NO: 24;
the above-mentioned antibody (4) has a heavy chain variable region comprising an amino acid sequence of SEQ ID NO: 28 and a light chain variable region comprising an amino acid sequence of SEQ ID NO: 32;
the above-mentioned antibody (5) has a heavy chain variable region comprising an amino acid sequence of SEQ ID NO: 36 and a light chain variable region comprising an amino acid sequence of SEQ ID NO: 40;
the above-mentioned antibody (6) has a heavy chain variable region comprising an amino acid sequence of SEQ ID NO: 44 and a light chain variable region comprising an amino acid sequence of SEQ ID NO: 48;
the above-mentioned antibody (7) has a heavy chain variable region comprising an amino acid sequence of SEQ ID NO: 52 and a light chain variable region comprising an amino acid sequence of SEQ ID NO: 56; and the above-mentioned antibody (8) has a heavy chain variable region comprising an amino acid sequence of SEQ ID NO: 60 and a light chain variable region comprising an amino acid sequence of SEQ ID NO: 64.

[9] An isolated human anti-botulinum toxin type-A antibody comprising any one of (1) to (8) as defined in the item [2].

[10] The isolated human anti-botulinum toxin type-A antibody according to the item [9], wherein:

the above-mentioned antibody (1) has a heavy chain variable region comprising an amino acid sequence of SEQ ID NO: 4 and a light chain variable region comprising an amino acid sequence of SEQ ID NO: 8;

the above-mentioned antibody (2) has a heavy chain variable region comprising an amino acid sequence of SEQ ID NO: 12 and a light chain variable region comprising an amino acid sequence of SEQ ID NO: 16;

the above-mentioned antibody (3) has a heavy chain variable region comprising an amino acid sequence of SEQ ID NO: 20 and a light chain variable region comprising an amino acid sequence of SEQ ID NO: 24;

the above-mentioned antibody (4) has a heavy chain variable region comprising an amino acid sequence of SEQ ID NO: 28 and a light chain variable region comprising an amino acid sequence of SEQ ID NO: 32;

the above-mentioned antibody (5) has a heavy chain variable region comprising an amino acid sequence of SEQ ID NO: 36 and a light chain variable region comprising an amino acid sequence of SEQ ID NO: 40;

the above-mentioned antibody (6) has a heavy chain variable region comprising an amino acid sequence of SEQ ID NO: 44 and a light chain variable region comprising an amino acid sequence of SEQ ID NO: 48;

the above-mentioned antibody (7) has a heavy chain variable region comprising an amino acid sequence of SEQ ID NO: 52 and a light chain variable region comprising an amino acid sequence of SEQ ID NO: 56; and the above-mentioned antibody (8) has a heavy chain variable region comprising an amino acid sequence of SEQ ID NO: 60 and a light chain variable region comprising an amino acid sequence of SEQ ID NO: 64.

[11] An isolated nucleic acid molecule encoding a heavy chain variable region and/or a light chain variable region of the antibody of the item [10].

[12] A vector having the nucleic acid molecule of the item [11].

[13] A transformant obtainable by transformation with the vector of the item [12].

[14] A method for producing a human anti-botulinum toxin type-A antibody comprising the steps of:

culturing the transformant of the item [13] to produce a human anti-botulinum toxin type-A antibody, and collecting the culture supernatant and purifying the human anti-botulinum toxin type-A antibody from the culture supernatant.

TERMINOLOGY

For convenience of explanation, definitions of certain terms as used in this description are explained below.

In the present description, the term "include (comprise)" or "including (comprising)" is used to include the meaning of "consisting of". Therefore, for example, "a product (or a method) including (comprising) a plurality of elements (members)" also means a product (or a method) consisted of a plurality of elements (members)" as one of meanings.

The term "isolated" refers to a state of being taken out from its original environment (for example, natural environment in the case of natural substances), that is, a state that is different from the original existing state by an artificial manipulation.

The "isolated antibody" does not include an antibody that is natural without any external manipulation (artificial manipulation), that is, the term does not include an antibody in a state of being produced in an individual body and remaining therein. Further, an isolated antibody is typically present in a state in which other kinds of antibodies are not contaminated, that is, it exists alone (as a group of the same kind of antibodies).

As for the "complementarity-determining region (CDR)", it follows the definition by Kabat et al. (see "Sequences of Proteins of Immunological Interest", 4th edition US Department of Health and Human Services (1987)).

The "composition for neutralizing botulinum toxin type-A" refers to a pharmaceutical mixture that contains a plurality of kinds of antibodies as an active ingredient and shows a neutralizing activity against botulinum toxin type-A.

The "antitoxin titer" in the present invention is expressed in terms of an international unit unless otherwise particularly specified. The "antitoxin titer" is determined according to The Japanese Pharmacopoeia, clause 3.2.7 "titer test" of "freeze-dried botulism antitoxin, equine" (freeze-dried botulinum antitoxin) described in biological products listed in each monograph on drugs).

In this description, the following abbreviations (the terms inside the parentheses) are used according to practice, if necessary.

Heavy chain (H-chain), light chain (L-chain), heavy chain variable region (VH), light chain variable region (VL), complementarity-determining region (CDR), complementarity-determining region 1 (CDR1), complementarity-determining region 2 (CDR2), complementarity-determining region 3 (CDR3), heavy chain complementarity-determining region 1 (VH CDR1), heavy chain complementarity-determining region 2 (VH CDR2), heavy chain complementarity-determining region 3 (VH CDR3), light chain complementarity-determining region 1 (VL CDR1), light chain complementarity-determining region 2 (VL CDR2), and light chain complementarity-determining region 3 (VL CDR3).

BRIEF DESCRIPTION OF THE DRAWINGS

FIG. 3 shows the result of a neutralization test (animal test) using the antibody obtained in screening experiment 1 as a sample. The symbols (+, –, etc.) in the Table show the severity of the symptoms. The symptom is severe in the order of ±, +, and ++.

FIG. 5 shows a binding activity of the antibody obtained in screening experiment 2 (lower part (4th) of FIG. 5) and a binding activity of the antibody obtained in screening experiment 3 (upper part of FIG. 5 (third-2)).

FIG. 6 represents the sequence (SEQ ID NO. 20) of VH of BT-058, sequence (SEQ ID NO. 12) of VH of BT-047, sequence (SEQ ID NO. 4) of VH of BT-015, sequence (SEQ ID NO. 24) of VL of BT-058, sequence (SEQ ID NO. 16) of VL of BT-047, and sequence (SEQ ID NO. 8) of VL of BT-015.

FIG. 8 shows the result of a neutralization test (animal test) using the antibody obtained in screening experiment 4 as a sample. The symbols (+, ++, etc.) in the Table show the severity of the symptoms. The symptom is severe in the order of ++, and +++. The symbol "d" represents "mouse death".

FIG. 9 shows the process of screening using botulinum toxoid.

FIG. 14 shows the result of a neutralization test (animal test) using the antibodies obtained in screening experiments 5 and 6 as a sample. The symbols (+, ++, etc.) in the Table show the severity of the symptoms. The symptom is severe in the order of ±, +, ++, and +++. The symbol "d" represents "mouse death".

FIG. 15 shows the process of screening using neurotoxin (concentration of neurotoxin-specific antibody).

FIG. 16 shows the comparison of an amino acid sequence of the antibodies obtained in screening experiments 1 to 6. From top in order, FIG. 16 represents the sequence (SEQ ID NO. 36) of VH of BT-175, sequence (SEQ ID NO. 28) of VH of NT-221, sequence (SEQ ID NO. 44) of VH of NT-320, sequence (SEQ ID NO. 60) of VH of NT-539, sequence (SEQ ID NO. 4) of VH of BT-015, sequence (SEQ ID NO. 52) of VH of NT-523, sequence (SEQ ID NO. 48) of VL of NT-320, sequence (SEQ ID NO. 64) of VL of NT-539, sequence (SEQ ID NO. 32) of VL of NT-221, sequence (SEQ ID NO. 40) of VL of BT-175, sequence (SEQ ID NO. 8) of VL of BT-015, and sequence (SEQ ID NO. 56) of VL of NT-523. Further, homology with Germline was also shown.

Figure 28:
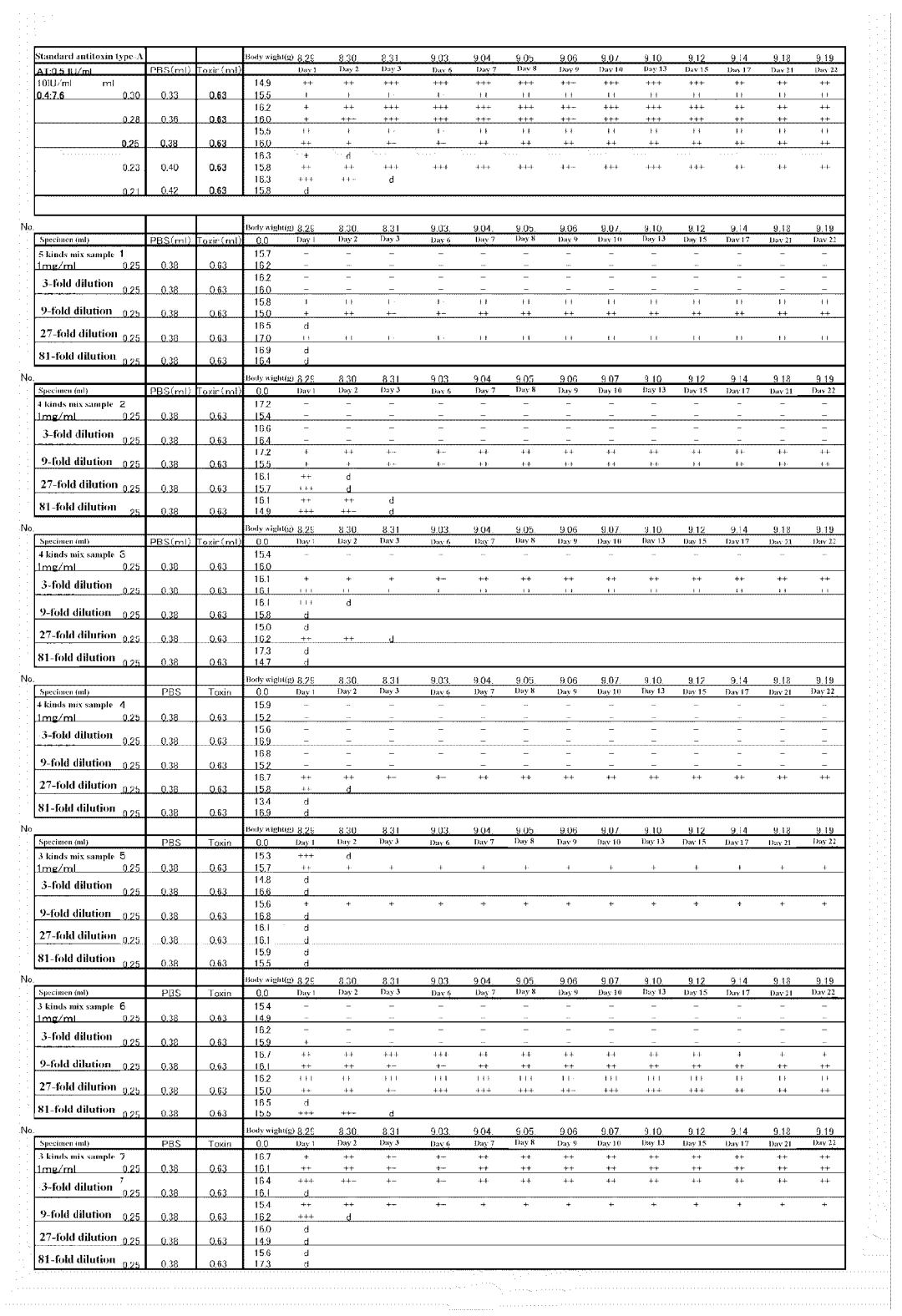

FIG. 28 shows the result of a neutralization test using five kinds of antibody clones (BT-015, BT-175, NT-221, NT-320, NT-523) as a sample. The symbols (+, ++, etc.) in the Table show the severity of the symptoms. The symptom is severe in the order of +, ++, and +++. The symbol "−" means "no detection of the symptom" and the symbol "d" represents "mouse death", respectively.

FIG. 29 shows an epitope analysis of the antibody by ELISA and the reactivity to toxin subtype-A2. In order to analyze the epitopes of six kinds of neutralizing antibodies (BT-015, BT-175, NT-221, NT-320, NT-523, NT-539) in more detail and also to confirm the reactivity to a subtype-A2 thereof, neurotoxin (CHIBA-H) at the same time, ELISA was carried out using the antigen described below. The values of OD492 nm of each clone were shown in a table form.

FIG. 30 shows an epitope analysis by immunoblotting. The results of the epitope analysis by immunoblotting neurotoxin (NT) and the neuronal cell binding domain of the heavy chain C-terminal end (Hc, E. coli recombinant protein) were shown. Each antibody clone was diluted into two kinds of concentrations (50 µg/ml (solid line lane) and 5 µg/ml (dashed line lane), and then allowed to react. The primary structure of the Hc domain is recognized in NT-523. However, in this experiment, any band about other antibodies was not detected.

FIG. 32 is a table showing the summarized results of the epitope analysis, and the classification of the epitopes of 6 kinds of the antibodies. Based on comprehensive evaluation on the epitope analysis results, the candidates of antibody epitopes were summarized at the bottom line of the table. In addition, as for the binding activity of each clone (epitope candidate), the case where the binding to neurotoxin was observed, it was expressed as NT, the case where the binding to the H-chain was observed, it was expressed as H, the case where the binding to neuronal cell-binding domain at the C-terminal end of the H-chain was observed, it was expressed as Hc, and the case where the binding to L-chain was observed, it was expressed as L. The symbol "(−)" indicates that determination is not possible.

BEST MODE FOR CARRYING OUT THE INVENTION

Figure 1:
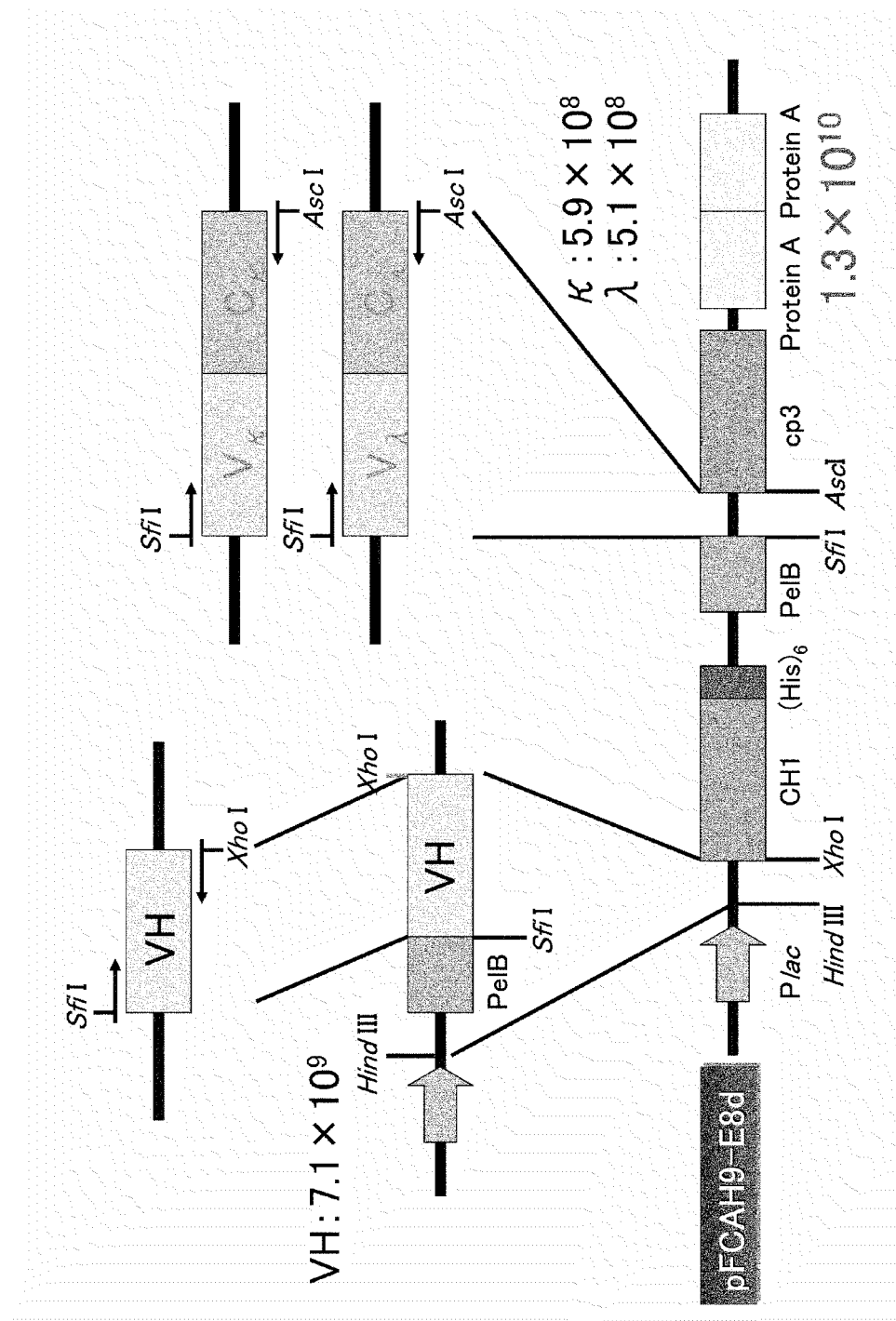
FIG. 1 shows the construction of an antibody library.

A first aspect of the present invention relates to a composition for neutralizing botulinum toxin type-A (hereinafter also referred to as "composition of the present invention"). At least three kinds of antibodies are used in the composition of the present invention. Any of these three antibodies are each a human antibody that recognizes botulinum toxin type-A. In the present description, the three antibodies are called as "a first human anti-botulinum toxin type-A antibody", "a second human anti-botulinum toxin type-A antibody", and "a third human anti-botulinum toxin type-A antibody". In addition, for convenience of explanation, "the first human anti-botulinum toxin type-A antibody" is hereinafter abbreviated as "the first antibody", "the second human anti-botulinum toxin type-A antibody" is hereinafter abbreviated as "the second antibody", and "the third human anti-botulinum toxin type-A antibody" is hereinafter abbreviated as "the third antibody".

The present inventors have succeeded in obtaining a human antibody clone (BT-015, BT-047, BT-058, NT-221, BT-175, NT-320, NT-523, NT-539) effective for neutralization of botulinum toxin type-A (see the description of Examples). In addition, it was shown that the human antibody clones that had successfully obtained were classified into four kinds based on the difference of epitope. The first antibody is the one corresponding to an antibody clone BT-015 that was shown to be effective for neutralizing botulinum toxin type-A when used in combination with other antibody clone, and is characterized by recognizing the epitope of the antibody clone BT-015 (i.e. an antibody having a heavy chain variable region comprising an amino acid sequence of SEQ ID No. 4 and a light chain variable region comprising an amino acid sequence of SEQ ID No. 8). Because the epitope of the first antibody accords with the epitope of the antibody clone BT-015, competition is observed if the first antibody and the antibody clone BT-015 are reacted with the botulinum toxin at the same time. Therefore, the eligibility as the first antibody can be confirmed by a competitive experiment using the antibody clone BT-015.

The second antibody is the one corresponding to an antibody clone BT-175 that was shown to be effective for neutralizing botulinum toxin type-A when used in combination with other antibody clone, and is characterized by recognizing the epitope of the antibody clone BT-175 (i.e. an antibody having a heavy chain variable region comprising an amino acid sequence of SEQ ID No. 36 and a light chain variable region comprising an amino acid sequence of SEQ ID No. 40). Note that the eligibility as the second antibody can be confirmed in the same manner as in the first antibody clone.

The third antibody is the one corresponding to an antibody clone (NT-320 or NT-523) that was shown to be effective for neutralizing botulinum toxin type-A when used in combination with an antibody clone BT-015 and an antibody clone BT-175, and is characterized by recognizing the epitope of the antibody clone NT-320 (i.e. an antibody having a heavy chain variable region comprising an amino acid sequence of SEQ ID No. 44 and a light chain variable region comprising an amino acid sequence of SEQ ID No. 48), or the epitope of the antibody clone NT-523 (i.e. an antibody having a heavy chain variable region comprising an amino acid sequence of SEQ ID No. 52 and a light chain variable region comprising an amino acid sequence of SEQ ID No. 56). Note that the eligibility as the third antibody can be confirmed in the same manner as in the first antibody clone.

In one aspect of the present invention, the first antibody is any one of antibodies selected from the group consisting of the following (1) to (3); the second antibody is the following antibody (4) or (5); and the third antibody is any one of antibodies selected from the group consisting of the following (6) to (8):

(1) an antibody having a heavy chain complementarity-determining region 1 comprising an amino acid sequence of SEQ ID NO: 1, a heavy chain complementarity-determining region 2 comprising an amino acid sequence of SEQ ID NO: 2, a heavy chain complementarity-determining region 3 comprising an amino acid sequence of SEQ ID NO: 3, a light chain complementarity-determining region 1 comprising an amino acid sequence of SEQ ID NO: 5, a light chain complementarity-determining region 2 comprising an amino acid sequence of SEQ ID NO: 6, and a light chain complementarity-determining region 3 comprising an amino acid sequence of SEQ ID NO: 7;

(2) an antibody having a heavy chain complementarity-determining region 1 comprising an amino acid sequence of SEQ ID NO: 9, a heavy chain complementarity-determining region 2 comprising an amino acid sequence of SEQ ID NO: 10, a heavy chain complementarity-determining region 3 comprising an amino acid sequence of SEQ ID NO: 11, a light chain complementarity-determining region 1 comprising an amino acid sequence of SEQ ID NO: 13, a light chain complementarity-determining region 2 comprising an amino acid sequence of SEQ ID NO: 14, and a light chain complementarity-determining region 3 comprising an amino acid sequence of SEQ ID NO: 15;

(3) an antibody having a heavy chain complementarity-determining region 1 comprising an amino acid sequence of SEQ ID NO: 17, a heavy chain complementarity-determining region 2 comprising an amino acid sequence of SEQ ID NO: 18, a heavy chain complementarity-determining region 3 comprising an amino acid sequence of SEQ ID NO: 19, a light chain complementarity-determining region 1 comprising an amino acid sequence of SEQ ID NO: 21, a light chain complementarity-determining region 2 comprising an amino acid sequence of SEQ ID NO: 22, and a light chain complementarity-determining region 3 comprising an amino acid sequence of SEQ ID NO: 23;

(4) an antibody having a heavy chain complementarity-determining region 1 comprising an amino acid sequence of SEQ ID NO: 25, a heavy chain complementarity-determining region 2 comprising an amino acid sequence of SEQ ID NO: 26, a heavy chain complementarity-determining region 3 comprising an amino acid sequence of SEQ ID NO: 27, a light chain complementarity-determining region 1 comprising an amino acid sequence of SEQ ID NO: 29, a light chain complementarity-determining region 2 comprising an amino acid sequence of SEQ ID NO: 30, and a light chain complementarity-determining region 3 comprising an amino acid sequence of SEQ ID NO: 31;

(5) an antibody having a heavy chain complementarity-determining region 1 comprising an amino acid sequence of SEQ ID NO: 33, a heavy chain complementarity-determining region 2 comprising an amino acid sequence of SEQ ID NO: 34, a heavy chain complementarity-determining region 3 comprising an amino acid sequence of SEQ ID NO: 35, a light chain complementarity-determining region 1 comprising an amino acid sequence of SEQ ID NO: 37, a light chain complementarity-determining region 2 comprising an amino acid sequence of SEQ ID NO: 38, and a light chain complementarity-determining region 3 comprising an amino acid sequence of SEQ ID NO: 39;

(6) an antibody having a heavy chain complementarity-determining region 1 comprising an amino acid sequence of SEQ ID NO: 41, a heavy chain complementarity-determining region 2 comprising an amino acid sequence of SEQ ID NO: 42, a heavy chain complementarity-determining region 3 comprising an amino acid sequence of SEQ ID NO: 43, a light chain complementarity-determining region 1 comprising an amino acid sequence of SEQ ID NO: 45, a light chain complementarity-determining region 2 comprising an amino acid sequence of SEQ ID NO: 46, and a light chain complementarity-determining region 3 comprising an amino acid sequence of SEQ ID NO: 47;

(7) an antibody having a heavy chain complementarity-determining region 1 comprising an amino acid sequence of SEQ ID NO: 49, a heavy chain complementarity-determining region 2 comprising an amino acid sequence of SEQ ID NO: 50, a heavy chain complementarity-determining region 3 comprising an amino acid sequence of SEQ ID NO: 51, a light chain complementarity-determining region 1 comprising an amino acid sequence of SEQ ID NO: 53, a light chain complementarity-determining region 2 comprising an amino acid sequence of SEQ ID NO: 54, and a light chain complementarity-determining region 3 comprising an amino acid sequence of SEQ ID NO: 55; and (8) an antibody having a heavy chain complementarity-determining region 1 comprising an amino acid sequence of SEQ ID NO: 57, a heavy chain complementarity-determining region 2 comprising an amino acid sequence of SEQ ID NO: 58, a heavy chain complementarity-determining region 3 comprising an amino acid sequence of SEQ ID NO: 59; a light chain complementarity-determining region 1 comprising an amino acid sequence of SEQ ID NO: 61, a light chain complementarity-determining region 2 comprising an amino acid sequence of SEQ ID NO: 62, and a light chain complementarity-determining region 3 comprising an amino acid sequence of SEQ ID NO: 63.

The above antibody (1) corresponds to an antibody clone BT-015, the above antibody (2) corresponds to an antibody clone BT-047, the above antibody (3) corresponds to a human antibody clone BT-058, the above antibody (4) corresponds to a human antibody clone NT-221, the above antibody (5) corresponds to a human antibody clone BT-175, the above antibody (6) corresponds to a human antibody clone NT-320, the above antibody (7) corresponds to a human antibody clone NT-523, and the above antibody (8) corresponds to a human antibody clone NT-539. Sequence information of each clone is given below.

```
(BT-015)
VH CDR1:        SEQ ID NO 1
VH CDR2:        SEQ ID NO 2
VH CDR3:        SEQ ID NO 3
VH:             SEQ ID NO 4
VL CDR1:        SEQ ID NO 5
VL CDR2:        SEQ ID NO 6
VL CDR3:        SEQ ID NO 7
VL:             SEQ ID NO 8
(BT-047)
VH CDR1:        SEQ ID NO 9
VH CDR2:        SEQ ID NO 10
VH CDR3:        SEQ ID NO 11
VH:             SEQ ID NO 12
VL CDR1:        SEQ ID NO 13
VL CDR2:        SEQ ID NO 14
VL CDR3:        SEQ ID NO 15
VL:             SEQ ID NO 16
(BT-058)
VH CDR1:        SEQ ID NO 17
```

-continued

```
VH CDR2:        SEQ ID NO 18
VH CDR3:        SEQ ID NO 19
VH:             SEQ ID NO 20
VL CDR1:        SEQ ID NO 21
VL CDR2:        SEQ ID NO 22
VL CDR3:        SEQ ID NO 23
VL:             SEQ ID NO 24
(NT-221)
VH CDR1:        SEQ ID NO 25
VH CDR2:        SEQ ID NO 26
VH CDR3:        SEQ ID NO 27
VH:             SEQ ID NO 28
VL CDR1:        SEQ ID NO 29
VL CDR2:        SEQ ID NO 30
VL CDR3:        SEQ ID NO 31
VL:             SEQ ID NO 32
(BT-175)
VH CDR1:        SEQ ID NO 33
VH CDR2:        SEQ ID NO 34
VH CDR3:        SEQ ID NO 35
VH:             SEQ ID NO 36
VL CDR1:        SEQ ID NO 37
VL CDR2:        SEQ ID NO 38
VL CDR3:        SEQ ID NO 39
VL:             SEQ ID NO 40
(NT-320)
VH CDR1:        SEQ ID NO 41
VH CDR2:        SEQ ID NO 42
VH CDR3:        SEQ ID NO 43
VH:             SEQ ID NO 44
VL CDR1:        SEQ ID NO 45
VL CDR2:        SEQ ID NO 46
VL CDR3:        SEQ ID NO 47
VL:             SEQID NO 48
(NT-523)
VH CDR1:        SEQ ID NO 49
VH CDR2:        SEQ ID NO 50
VH CDR3:        SEQ ID NO 51
VH:             SEQ ID NO 52
VL CDR1:        SEQ ID NO 53
VL CDR2:        SEQ ID NO 54
VL CDR3:        SEQ ID NO 55
```

```
        -continued
VL:                SEQ ID NO 56

(NT-539)
VH CDR1:           SEQ ID NO 57

VH CDR2:           SEQ ID NO 58

VH CDR3:           SEQ ID NO 59

VH:                SEQ ID NO 60

VL CDR1:           SEQ ID NO 61

VL CDR2:           SEQ ID NO 62

VL CDR3:           SEQ ID NO 63

VL:                SEQ ID NO 64
```

In one preferable embodiment, the antibody (1) has a heavy chain variable region comprising an amino acid sequence of SEQ ID NO: 4 and a light chain variable region comprising an amino acid sequence of SEQ ID NO: 8. The antibody (2) has a heavy chain variable region comprising an amino acid sequence of SEQ ID NO: 12 and a light chain variable region comprising an amino acid sequence of SEQ ID NO: 16. The antibody (3) has a heavy chain variable region comprising an amino acid sequence of SEQ ID NO: 20 and a light chain variable region comprising an amino acid sequence of SEQ ID NO: 24. The antibody (4) has a heavy chain variable region comprising an amino acid sequence of SEQ ID NO: 28 and a light chain variable region comprising an amino acid sequence of SEQ ID NO: 32. The antibody (5) has a heavy chain variable region comprising an amino acid sequence of SEQ ID NO: 36 and a light chain variable region comprising an amino acid sequence of SEQ ID NO: 40. The antibody (6) has a heavy chain variable region comprising an amino acid sequence of SEQ ID NO: 44 and a light chain variable region comprising an amino acid sequence of SEQ ID NO: 48. The antibody (7) has a heavy chain variable region comprising an amino acid sequence of SEQ ID NO: 52 and a light chain variable region comprising an amino acid sequence of SEQ ID NO: 56. The antibody (8) has a heavy chain variable region comprising an amino acid sequence of SEQ ID NO: 60 and a light chain variable region comprising an amino acid sequence of SEQ ID NO: 64.

The origin, kind, class, and morphology of each antibody are not limited. Preferably, each antibody is prepared as a fully human IgG antibody. The kind of the constant region in this case is not particularly limited. That is, the heavy chain is not limited to a γ chain, and it may be a μ chain, an α chain or an ε chain. Similarly, the light chain may be a κ chain or a λ chain.

Each antibody can also be prepared as an antibody fragment such as Fab, Fab', F(ab')$_2$, scFv, or dsFv antibodies. Fab can be obtained by digesting an IgG antibody with papain in the presence of cysteine. Fab is a fragment having a molecular weight of about 50,000, and comprising an L-chain region and an H-chain fragment that comprises apart of an H-chain variable region, a CH1 domain, and a hinge region. When a desired IgG antibody is available, Fab can be obtained by digesting this with papain. Furthermore, DNA encoding the L-chain and a part of the H-chain is integrated into an appropriate vector, and Fab can be prepared from the transformant transformed by using this vector.

Fab' is a fragment having a molecular weight of about 50,000, which can be obtained by cutting the disulfide linkage between H-chains of the F(ab')2 mentioned below. If a desired IgG antibody is available, Fab' can be obtained by digesting it with pepsin and cutting the disulfide linkage with use of a reducing agent. Furthermore, similar to Fab, Fab' can be prepared by genetic engineering with a DNA that encodes Fab'.

F(ab')$_2$ can be obtained by pepsin digestion of an IgG antibody. F(ab')$_2$ is a fragment having a molecular weight of about 100,000, wherein a fragment (Fab') comprising an L-chain region and an H-chain fragment that comprises a part of the H-chain variable regions, the CH1 domain, and the hinge region is bound by disulfide linkage. If a desired IgG antibody is available, F(ab')$_2$ can be obtained by digesting it with pepsin. Furthermore, similar to Fab, F(ab')$_2$ can be prepared by genetic engineering with a DNA that encodes F(ab')$_2$.

ScFv is a single stranded antibody fragment in which Fv fragments including an H-chain variable region and an L-chain variable region are linked to each other by linking the C terminal of one chain and the N terminal of the other chain with an appropriate peptide linker. As the peptide linker, for example, (GGGGS)$_3$ having a high flexibility and the like can be used. For example, by using a DNA encoding the H-chain variable region and the L-chain variable region and DNA encoding the peptide linker to construct DNA encoding scFv antibody, and to integrate into an appropriate vector, so that scFv can be prepared from the transformant that has been transformed by using this vector.

dsFv is an Fv fragment in which a Cys residue is introduced into appropriate positions of the H-chain variable region and the L-chain variable region so that the H-chain variable region and the L-chain variable region are stabilized by the disulfide linkage. The position of each chain into which the Cys residue is introduced can be determined based on the three-dimensional structure predicted by molecule modeling. For example, the three-dimensional structure is predicted from the amino acid sequence of the H-chain variable region and the L-chain variable region to construct a DNA encoding each of the H-chain variable region and the L-chain variable region into which mutation is introduced based on the prediction. This is integrated into an appropriate vector, and dsFv can be prepared from the transformant transformed by using this vector.

Here, a preferable combination of the antibodies in the composition of the present invention can include the following combinations. The combinations correspond to those of antibodies that were observed to have the highest neutralizing activity in the neutralization test shown in the following Examples.

The first antibody: Antibody of (1)
The second antibody: Antibody of (5)
The third antibody: Antibody of (6)

When the above-mentioned combination is adopted, the antibody (7) is preferable to be used in combination as the fourth human anti-botulinum toxin type-A antibody (the fourth antibody). The combination of four kinds of antibodies thus obtained corresponds to that of antibodies that were observed to have the highest neutralizing activity in the neutralization test shown in the following Examples.

Another example of a preferable combination of the antibodies is shown below. The combination corresponds to that of the antibody that was observed to have the highest neutralizing activity in the neutralization test shown in the following Examples.

The first antibody: Antibody (1)

The second antibody: Antibody (5)

The third antibody: Antibody (7)

Note that in the case where the antibodies as an active ingredient are limited to three kinds of antibodies, it is preferable to use the antibody (8) as the above third antibody because it retains a stronger binding activity than the antibody (7) against toxin subtype-A2 among toxins type-A.

When the above-mentioned combination is adopted, the antibody (4) is preferable to be used in combination as the fourth human anti-botulinum toxin type-A antibody (as the fourth antibody).

The combination when four kinds of antibodies are used together is not limited to the above-mentioned two examples. Preferable combinations of four kinds of antibodies are shown below.

The first antibody: Any one of the antibodies selected from the group consisting of (1) to (3)
The second antibody: Antibody (4) or (5)
The third antibody: Antibody (6)
The fourth antibody: Antibody (7) or (8)

The antibodies (1) to (8) are those used as an active ingredient of the composition showing a high neutralizing activity to botulinum toxin type-A, and they themselves have a high titer. Thus, as a second aspect of the present invention, an antibody comprising any one of the antibodies (1) to (8) for neutralizing a botulinum toxin type-A is provided. Moreover, as a third aspect of the present invention, an isolated nucleic acid molecule encoding the heavy chain variable region and/or the light chain variable region of the antibody is provided. The nucleotide sequences (the heavy chain variable region and the light chain variable region) of the antibody clone corresponding to each of the antibodies (1) to (8) are shown below.

```
(BT-015)
VH:             SEQ ID NO 65

VL:             SEQ ID NO 66

(BT-047)
VH:             SEQ ID NO 67

VL:             SEQ ID NO 68

(BT-058)
VH:             SEQ ID NO 69

VL:             SEQ ID NO 70

(NT-221)
VH:             SEQ ID NO 71

VL:             SEQ ID NO 72

(BT-175)
VH:             SEQ ID NO 73

VL:             SEQ ID NO 74

(NT-320)
VH:             SEQ ID NO 75

VL:             SEQ ID NO 76

(NT-523)
VH:             SEQ ID NO 77

VL:             SEQ ID NO 78

(NT-539)
VH:             SEQ ID NO 79

VL:             SEQ ID NO 80
```

In addition, each antibody of the above-mentioned (1) to (8) retains a strong binding activity to toxin A2-type that is a subtype of type-A, and can become an active ingredient of the composition showing a strong neutralizing activity.

The antibodies (antibodies (1) to (8)) of the present invention can be prepared by a genetic engineering method based on the sequence information of each antibody clone. That is, such antibodies of the present invention can be typically prepared by a series of steps comprising preparing a gene expression construct encoding a targeted antibody, expressing using an appropriate expression system, and collecting an expressed product.

The expression system is not particularly limited. That is, any expression system can be used so long as an objective recombinant antibody is expressed. However, when an IgG type recombinant antibody is expressed, an expression system using animal cells is preferably used. Moreover, when the antibody fragment such as Fab, Fab', F(ab')$_2$, scFv, or dsFv derived from the variable regions is made to express, it is possible to utilize an expression system using microorganisms in addition to animal cells, such as *E. coli* and yeast. A suitable expression vector is used depending on the host to be used. If a signal peptide is utilized, a target recombinant antibody can be extracellularly secreted, or it can be transported to a periplasm region, or it can be retained in the cells.

In the following, the most common expression method using the animal cell is described in detail. At first, DNA encoding the heavy chain variable region (VH) of a target antibody is prepared by chemical synthesis, biochemical cleavage/recombination, and the like. The resultant DNA encoding the H-chain variable region is ligated with DNA encoding the constant region of the human H-chain to integrate into an expression vector, thereby to obtain an H-chain expression vector. In a similar manner, an L-chain expression vector is made. As to an FR (framework region) that exists with sandwiching of the CDR regions, a variable region with some mutations introduced may also be used. In other words, this is because antibodies whose CDR domains are all identical recognize the identical epitope, and modification of the FR is permitted as far as the finally obtained antibody recognizes botulinum toxin type-A and shows a sufficient binding activity Here, if an amino acid sequence is specified, it is possible to predict a three-dimensional structure (spatial conformation) of the variable region, as well as to predict the change of the three-dimensional structure by having added a specific modification to the FR. In addition, it is possible to construct a molecular model of the variable region by using a computer program ENCAD (Energy Calculation and Dynamics) or it is also possible to decide amino acids in the FR that is adjacent enough to potentially interact with the CDR (e.g., see WO 97/002290). Moreover, a computer program Verify-3D for quantitatively evaluating whether or not the environment is suitable for each amino acid residue, or a modeling technique for exclusive use of immunoglobulin (WAM-Web Antibody Modeling or AbM manufactured by Oxford Molecular) can also be utilized. The mutation of the variable region can be optimized by the routine work using the random PCR and the phage display method (see Manuel B. et al., J. Biol. Chem. Vol. 272 no. 16 10678 "Antibody humanization using monovalent page display" and WO 2007/094754, etc.).

The number of amino acids to be modified is preferably 15% or less of the whole FR, more preferably 10% or less of the whole FR, still more preferably 5% or less of the whole FR, and most preferably 1% or less of the whole FR.

An "expression vector" refers to a nucleic acid molecule capable of introducing a nucleic acid inserted in a vector to a desired cell (a target cell) and expressing it in the cell. The expression vector includes a virus vector and a non-virus vector. The gene introduction method using a virus vector utilizes skillfully the phenomenon that the cell is infected with virus, and high gene introduction efficiency is obtained. The virus vector includes, but not limited to, an SV40 virus based vector, an EB virus based vector, a BPV (papillomavirus) based vector, and the like. As a non-virus vector, liposomes, positively charged liposomes (Felgner, P. L., Gadek, T. R., Holm, M. et al., Proc. Natl. Acad. Sci., 84:7413-7417, 1987), HVJ (Hemagglutinating virus of Japan)-liposomes (Dzau, V. J., Mann, M., Morishita, R. et al., Proc. Natl. Acad. Sci., 93:11421-11425, 1996, Kaneda, Y., Saeki, Y. & Morishita, R., Molecular Med. Today, 5:298-303, 1999) and the like have been developed. The expression vector may be constructed as such a non-viral vector.

The promoters included in the expression vector, such as an SV40 initial promoter, an SV40 late promoter, a cytomegalovirus promoter, and a chicken β-actin promoter are used.

After having prepared an H-chain expression vector and an L-chain expression vector, a host cell is co-transformed using these vectors. As a host cell, CHO cells (Chinese hamster ovary) (A. Wright & S. L. Morrison, J. Immunol. 160, 3393-3402 (1998)), SP2/0 cells (mouse myeloma) (K. Motmans et al., Eur. J. Cancer Prev. 5, 512-519 (1996), R. P. Junghans et al., Cancer Res. 50, 1495-1502 (1990)) and the like are preferably used. For such transformation, the lipofectin method (R. W. Malone et al., Proc. Natl. Acad. Sci. USA 86, 6077 (1989), P. L. Felgner et al., Proc. Natl. Acad. Sci. USA 84, 7413 (1987), the electroporation method, the calcium phosphate method (F. L. Graham & A. J. van der Eb, Virology 52, 456-467 (1973)), the DEAE-Dextran method and the like are preferably used.

The ratio of the H-chain expression vector and the L-chain expression vector, and the timing of the introduction are not particularly limited. The ratio of both vectors (H-chain expression vector:L-chain expression vector (molar ratio)) is, for example, 1:0.5-5, preferably 1:0.8-1.2. With respect to the timing of the introduction of such vectors, the H-chain expression vector and the L-chain expression vector may be introduced into the host cell at the same time, or one of both vectors may be firstly introduced. Moreover, transformation may be performed by constructing an expression vector in which both of DNA encoding VH and DNA encoding VL are integrated and transforming a host cell with the vector, instead of by constructing the H-chain expression vector and the L-chain expression vector separately as mentioned above.

As a marker for use in the selection of transformants (selection marker), generally used marker genes (for example, see A laboratory manual of genetic engineering of animal cells by Michael Kriegler (translated and supervised by Ikunoshin Kato, Takara Shuzo (1994)), including an aminoglycoside 3'-phosphotransferase (neo) gene, a dihydrofolate reductase (dhfr) gene, a puromycin-resistant enzyme gene, a glutamine synthase (GS) gene, etc., can be used.

An antibody is collected (separated/purified) from the transformant cells or the culture solution. The collection of the antibody may be carried out according to a conventional manner. In other words, the antibody is collected by using centrifugation, ammonium sulfate fractionation, salting out, ultrafiltration, affinity chromatography (using Protein A resin and Protein G resin), ion exchange chromatography, gel filtration chromatography, or the like.

The antibody thus obtained is used as an effective ingredient of the composition of the present invention. In constituting the composition of the present invention, it may be formulated according to the conventional method. In the formulation, other ingredients acceptable for formulation (for example, carrier, excipient, disintegrator, buffer, emulsifier, suspending agent, soothing agent, stabilizer, preservative, antiseptic agent, physiological saline, etc.) may be contained.

Examples of the excipient may include water, physiological saline solution, Ringer's solution, dextrose solution, various buffers (phosphate buffer, bicarbonate buffer, Tris-buffer, etc.), lactose, starch, sorbitol, D-mannitol, white soft sugar, and the like. As an example of the disintegrator, starch, carboxymethyl cellulose, calcium carbonate, and the like may be used. As an example of the buffer, phosphate, citrate, acetate, and the like may be used. As an example of the emulsifier, gum Arabic, sodium alginate, tragacanth, and the like may be used. As an example of the suspending agent, glyceryl monostearate, aluminum monostearate, methylcellulose, carboxymethyl cellulose, hydroxymethyl cellulose, sodium lauryl sulfate, and the like may be used. As an example of the soothing agent, benzyl alcohol, chlorobutanol, sorbitol, and the like may be used. As an example of the stabilizer, propylene glycol, diethylene sulfite, ascorbic acid, and the like may be used. As an example of the preservative, phenol, benzalkonium chloride, benzyl alcohol, chlorobutanol, methylparaben, and the like may be used. As an example of the antiseptic agent, benzalkonium chloride, paraoxybenzoate, chlorobutanol, and the like may be used.

There is no particular limitation to the dosage form in the formulation, but pharmaceutical formulations having an immediate action, such as injections, external preparations, or suppositories, are preferable.

The mixing ratio of each antibody as an active ingredient is not particularly limited, but the amount of each antibody present becomes typically the same amount (mixed in an equimolar ratio). In addition, a person skilled in the art could optimize the mixing ratio through a similar test as shown later in the neutralization test of Examples.

Moreover, the class and morphology of each antibody are arbitrary. Therefore, the composition of the present invention may be comprised of a state where a different class of antibodies are present in a mixture form or a state where antibodies with a different morphology are present in a mixture form.

It is preferable to determine the antibody concentration in the composition of the present invention by calculating backwards after taking into consideration of the final dosage form and administration schedule.

The state of the composition of the present invention is not particularly limited. For example, the composition of the present invention is prepared into a liquid state or a dry state (preferably freeze-dried state). For example, in the case of freeze-drying, it may be carried out after having adjusted the concentration to 500 units or more of antitoxin titer as an active ingredient in a final 1 mL dissolved with a solvent. In addition, the content unit of the subdivision container is preferably set to 10000 units or more of the antitoxin titer, according to the clause 5.2 "content unit of subdivision container" of "freeze-dried botulism antitoxin, equine (freeze-dried botulinum antitoxin)" described in biological products listed in each monograph on drugs of The Japanese Pharmacopoeia.

The composition of the present invention is typically used for treatment and prevention of the botulism. The composition of the present invention is applied to a subject (patient) by oral administration or parenteral administration (intravenous injection, intraarterial injection, subcutaneous injection, intramuscular injection, intraperitoneal injection, direct introduction to the target cell, and the like) depending upon the dosage form.

The dose of the composition of the present invention will vary depending on the symptoms, age, sex, body weight, and the like, of the patient, but the person skilled in the art can set an appropriate dose. For example, the dose can be set so that a single dose of the antitoxin for an adult (body weight: about 60 kg) is 10,000 units to 100,000 units. In the setting of the dose and administration schedule, conditions of a patient, and efficacy duration time of the drug can be considered; taking into consideration of a relative titer of the composition of the present invention and the equine antitoxin, with reference to the dose and administration schedule used in the equine antitoxin (Nichii Zasshi (Journal of the Japan Medical Association), vol. 128 no. 1, Jul. 1, 2002).

The antitoxin titer of the composition of the present invention is preferably evaluated by an international standard so that the composition becomes suitable for the international use. The titer of the antitoxin based on the international standard can be calculated by the detection according to the clause of The Japanese Pharmacopoeia, "freeze-dried botulism antitoxin, equine (freeze-dried botulinum antitoxin)", more particularly, the clause 3.2.7 "titer test" described in biological products listed in each monograph on drugs.

EXAMPLES

1. Preparation of Botulinum Toxoid Immune Antibody Library 1-1. Inoculation of Botulinum Toxoid to Human Volunteers A toxoid was prepared by culturing *Clostridium botulinum* types A, B, E and F and using as the material the toxin obtained by purification of the resulting toxin. Especially, the type-A toxin was prepared by purifying a neurotoxin produced from *Clostridium botulinum* strain 97 (*C. botulinum* 97) or 62A (*C. botulinum* 62A) that has been currently used as a therapeutic toxin, according to the method performed in the B type neurotoxin (Infect. Immun. 18: 761-766, 1977). Each type of the purified toxins was inactivated with formalin, mixed with aluminum adjuvant to make a polyvalent mixed toxoid of precipitated ABEF types. This polyvalent toxoid was subcutaneously injected in 0.5 mL each as a basal immunity three times every 3-4 weeks and further once in 0.5 ml approximately 12 months later. Furthermore, ten years later and 20 years later, additional injections were made, and the same amount was further injected about three weeks before the following apheresis.

1-2. Preparation of Antibody Library

An aliquot (about 50 mL) of the blood mononuclear cell component corresponding to 3 liters of blood was taken out from a human who had received the inoculation of the ABEF type botulinum toxoid by apheresis. After diluting the mononuclear cells two-fold with PBS and collecting them, they were layered over Ficoll Paque™ PLUS (GE Healthcare Bioscience) which had been subdivided with a 10 ml/tube, and centrifuged under the conditions of 400 g, room temperature, and 30 minutes to repurify the mononuclear cell fraction only, thereby to fractionate $1.8 \times 10^9$ cells. Using $0.9 \times 10^9$ cells, extraction of total RNA was performed with an RNA Extraction Kit (Amersham) to collect 1.89 mg. After preparation of cDNA with use of a random primer Super Script II™ (Invitrogen™), a target antibody gene was amplified using the primer group specific to the H-chain (VH) of the antibody (see below) and the primer group specific to the L-chain (VLCL: kappa chain and lambda chain) (see below). The H-chain was integrated into a pscFvCA-E8VHd vector (utilization of SfiI-XhoI), and the L-chain was integrated into a phagemid vector (pFCAH9-E8d: see domestic re-publication of PCT international application WO 01/062907, utilization of SfiI-Asc), thereby to obtain an H-chain library, a kappa chain library and a lambda chain library. As for the library size, it was $7.05 \times 10^9$ for the H-chain library, $5.87 \times 10^8$ for the kappa chain library, and $5.05 \times 10^8$ for the lambda chain library.

(1) Primer Group Specific to VH

5'-end primer for obtaining a human antibody heavy chain gene (VH1 to VH7) and 3'-end primer (four kinds (697 to 700) of human JH primers were mixed in an equal amount)

Primer used for amplification of each VH family

Human VH primer (SfiI site are shown with the underline)

```
628 hVH1a (SEQ ID NO: 81):
GTCCTCGCAACTGCGGCCCAGCCGGCCATGGCCCAGGTGCAGCTGGT

GCAGTCTGG 629 hVH2a (SEQ ID NO: 82):
GTCCTCGCAACTGCGGCCCAGCCGGCCATGGCCCAGGTCAACTTAAG

GGAGTCTGG 630 hVH3a (SEQ ID NO: 83):
GTCCTCGCAACTGCGGCCCAGCCGGCCATGGCCGAGGTGCAGCTGGT

GGAGTCTGG 631 hVH4a (SEQ ID NO: 84):
GTCCTCGCAACTGCGGCCCAGCCGGCCATGGCCCAGGTGCAGCTGCA

GGAGTCGGG 632 hVH5a (SEQ ID NO: 85):
GTCCTCGCAACTGCGGCCCAGCCGGCCATGGCCCAGGTGCAGCTGTT

GCAGTCTGC 633 hVH6a (SEQ ID NO: 86):
GTCCTCGCAACTGCGGCCCAGCCGGCCATGGCCCAGGTACAGCTGCA

GCAGTCAGG 629-2 hVH2a-2 (SEQ ID NO: 87):
GTCCTCGCAACTGCGGCCCAGCCGGCCATGGCCCAGRTCACCTTGAA

GGAGTCTGGTCC 631-2 hVH4a-2 (SEQ ID NO: 88):
GTCCTCGCAACTGCGGCCCAGCCGGCCATGGCC CAGGTGCAGCTAC

AGCAGTGGGG 632-2 hVH5a-2 (SEQ ID NO: 89):
GTCCTCGCAACTGCGGCCCAGCCGGCCATGGCC GAGGTGCAGCTGG

TGCAGTCTGG 712 hVH7 (SEQ ID NO: 90):
GTCCTCGCAACTGCGGCCCAGCCGGCCATGGCCCAGGTGCAGCTGGT

GCAATCTGGGTCTGAGT
```

Human JH primer (BstPI, XhoI site are shown with the underline.)

```
697 hJH1-2 (SEQ ID NO: 91):
GGTGGAGGCACTCGAGACGGTGACCAGGGTGC 698 hJH3 (SEQ ID NO: 92):
GGTGGAGGCACTCGAGACGGTGACCATTGTCC 699 hJH4-5 (SEQ ID NO: 93):
GGTGGAGGCACTCGAGACGGTGACCAGGGTTC 700 hJH6 (SEQ ID NO: 94):
GGTGGAGGCACTCGAGACGGTGACCGTGGTCC
```

(2) Primer Group Specific to L-Chain (VLCL: Kappa Chain and Lambda Chain)

Primer annealed to 5'-end of VL for obtaining the light chain gene (κ1 to κ6, λ1 to λ6) and primer annealed to 3'-end of Cκ and cλ (hCKASC primer or hCLASC primer).

L-chain (VLCL: kappa chain and lambda chain)

```
5'-Primer κ1 to κ6
hVK1a (SEQ ID NO: 95):
GTCCTCGCAACTGCGGCCCAGCCGGCCATGGCCGACATCCAGATGAC
CCAGTCTCC hVK2a (SEQ ID NO: 96):
GTCCTCGCAACTGCGGCCCAGCCGGCCATGGCCGATGTTGTGATGAC
TCAGTCTCC hVK3a (SEQ ID NO: 97):
GTCCTCGCAACTGCGGCCCAGCCGGCCATGGCCGAAATTGTGTTGAC
GCAGTCTCC hVK4a (SEQ ID NO: 98):
GTCCTCGCAACTGCGGCCCAGCCGGCCATGGCCGACATCGTGATGAC
CCAGTCTCC hVK5a (SEQ ID NO: 99):
GTCCTCGCAACTGCGGCCCAGCCGGCCATGGCCGAAACGACACTCAC
GCAGTCTCC hVK6a (SEQ ID NO: 100):
GTCCTCGCAACTGCGGCCCAGCCGGCCATGGCCGAAATTGTGCTGAC
TCAGTCTCC 5'-primer λ1 ~λ6
hVL1 (SEQ ID NO: 101):
GTCCTCGCAACTGCGGCCCAGCCGGCCATGGCCCAGTCTGTGTTGAC
GCAGCCGCC hVL2 (SEQ ID NO: 102):
GTCCTCGCAACTGCGGCCCAGCCGGCCATGGCCCAGTCTGCCCTGAC
TCAGCCTGC hVL3a (SEQ ID NO: 103):
GTCCTCGCAACTGCGGCCCAGCCGGCCATGGCCTCCTATGTGCTGAC
TCAGCCACC hVL3b (SEQ ID NO: 104):
GTCCTCGCAACTGCGGCCCAGCCGGCCATGGCCTCTTCTGAGCTGAC
TCAGGACCC hVL4 (SEQ ID NO: 105):
GTCCTCGCAACTGCGGCCCAGCCGGCCATGGCCCACGTTATACTGAC
TCAACCGCC hVL5 (SEQ ID NO: 106):
GTCCTCGCAACTGCGGCCCAGCCGGCCATGGCCCAGGCTGTGCTCAC
TCAGCCGCC hVL6 (SEQ ID NO: 107):
GTCCTCGCAACTGCGGCCCAGCCGGCCATGGCAATTTTATGCTGAC
TCAGCCCCA 3'-primer hCKASC (SEQ ID NO: 108):
TCGACTGGCGCGCCGAACACTCTCCCCTGTTGAAGCTCTTTGTG 3'-primer HCLASC (SEQ ID NO: 109):
TCGACTGGCGCGCCGAACATTCTGTAGGGGCCACTGTCTTCTC
```

The H-chain gene was cut out from an H-chain library with use of HindIII and XhoI, and integrated into an L-chain library which had been prepared by mixing a kappa chain library and a lambda chain library in an equimolar ratio, thereby to finally obtain an Fab type antibody library of which library size was $1.3 \times 10^{10}$, for screening of anti-botulinum toxins (FIG. 1). The kind of the antibody is brought about by the diversity of CDR3 of VH, and it is thought that the huge antibody library made this time is enough to cover the diversity of the isolated antibody gene.

2. Screening of Antibody Libraries by Using Botulinum Toxoid Type-A and Nontoxic Protein Component of Botulinum Toxin 2-1. Screening Experiment 1
(1) Selection/Collection of Specific Clones In order to obtain a neutralizing antibody, it is ideal to screen an antibody binding to the site of neurotoxin having a neural toxin activity. However, in a volunteer blood donor who has been immunized with a toxoid prepared with a full length of the toxin, an antibody that binds to the nontoxic protein component (the antibody that is unnecessary here) has also been produced in the body. In addition, the availability of the neurotoxin having a neural toxin activity is limited, too. Then, a screening strategy was employed, which comprises, first, reacting a nontoxic protein component with a human antibody library to absorb the unnecessary antibody in the nontoxic protein component, collecting the reaction supernatant, and then reacting the botulinum toxoid with the human antibody library that had not been absorbed in the nontoxic protein component.

At first, each 100 µl of botulinum toxoid and nontoxic protein component which had been prepared to have a concentration of 10 µg/ml with PBS was subdivided into 6-wells of Microcup® (manufactured by Nunc, Maxisorp®), and reacted overnight at 4° C. for immobilization. After discarding the solution, 1% BSA/PBS was subdivided in 200 µl each and blocking was performed at 37° C. for one hour. The $1.0 \times 10^{13}$ clone equivalent of the human antibody library was first subdivided into the Microcup® (130 µl/well) immobilized with the nontoxic protein component, and allowed to react at 37° C. for two hours. Thereafter, the reaction supernatant was collected, subdivided again into the Microcup®immobilized with the nontoxic protein component, and reacted at 37° C. for two hours. After completion of the reaction, the reaction solution was discarded and washed five times with PBS. 0.1M HCl (prepared to pH 2.2 by dissolving glycine) was subdivided into 100 µl/well, reacted at room temperature for 15 minutes, and a phage antibody that had been bound to the antigen was collected.

This antibody was infected with 20 ml of *E. coli* DH12S™ (Invitrogen™) having an OD of 0.25 for one hour, added to 60 ml of an SBGA medium (prepared by adding 125 µg/ml (final concentration) of ampicillin sulfate and 0.5% (final concentration) of glucose to SB medium (prepared by dissolving MOPS 10 g, Tryptone 30 g and Yeast Extract 20 g to prepare the solution to pH 7 with 3N NaOH, and to make it up to a final volume of 1 liter)), cultured at 37° C. for two hours, added to 500 ml of an SBA medium, and further cultured at 37° C. for two hours. Subsequently, $1 \times 10^{12}$ helper phage K07 equivalent was added, cultured at 37° C. for two hours, and kanamycin was added to have a final concentration of 50 µg/ml and cultured at 30° C. for 18 hours. This was centrifuged at 8000 rpm for 10 minutes to collect the supernatant, to which was added 110 ml of the PEG solution (20% polyethylene glycol 6000, 2.5M NaCl). The mixture was well stirred, centrifuged at 8500 rpm for 15 minutes to precipitate the phage. The phage was suspended in 2.5 ml of PBS, and an aliquot was used to examine the *E. coli* infection count. Thus, the phage of the 1st screening (1st phage) was obtained.

The second screening was carried out under the same conditions as in the 1st screening except that 400 µl of the 1st phage was used and the washing times with PBS was 20 times. The 3rd screening was carried out under the same conditions as in the second screening except that 400 µl of the phage was used. After the 3rd screening, 46 clones were picked up.

(2) Determination of Base Sequence of Antibody Clone

*E. coli* obtained by the screening was diluted and seeded on a normal agar medium containing 100 mg/ml of ampicillin. The obtained colonies were picked up (corresponding to 46 clones described above (1)), cultured in 2xYTGA culture medium at 30° C. overnight. DNA was extracted by using PI-50 (Kurabo Industries Ltd.) and the base sequence was determined by a dideoxy method.

(3) Expression/Preparation of cp3 Fused Type Protein of Each Antibody Clone

*E. coli* obtained by the screening was diluted and seeded on a normal agar medium containing 100 mg/ml of ampicillin. The obtained colonies were picked up (corresponding to 46 clones described above (1)), cultured in 2xYTGA culture medium at 30° C. overnight. An aliquot (20 µl) was seeded to 2 ml of 0.05% glucose 2xYTA (2xYT, 100 µg/ml ampicillin sulfate, 0.05% glucose). After culturing at 30° C. for three hours, 1M of IPTG 20 µl was added thereto, and culturing was further continued for 20 hours. Then, the culture solution was treated with a microcentrifuge at 15000 rpm for 5 minutes to collect the supernatant. The supernatant contains cp3 fused type protein of each antibody clone. Using this supernatant, ELISA for toxoids and nontoxic components was carried out.

(4) ELISA Reaction with Botulinum Toxoids and Nontoxic Components

Binding ability of the antibody was determined by using ELISA with botulinum toxoids and nontoxic protein components.

An antibody in response to only botulinum toxoid becomes a target antibody for isolation (i.e., a neutralizing antibody).

At first, each 100 µl of botulinum toxoid and nontoxic protein component which had been prepared to have a concentration of 10 µg/ml with PBS was subdivided into Microcup® (manufactured by Nunc, Maxisorp®), and reacted overnight at 4° C. for immobilization. After removal of the solution, 1% BSA/PBS was subdivided in 200 µl each and blocking was performed at 37° C. for one hour. Each 100 µl of the supernatant (containing the cp3 fusion type protein of the antibody) obtained in above (3) was subdivided and reacted at 37° C. for one hour. After discarding the solution, washing with PBS was performed and a rabbit anti-cp3 antibody (MBL) that had been diluted with PBS to 2.5 10 µg/ml was reacted at 37° C. for one hour. After discarding the solution, washing with PBS was performed and an HRP-labeled goat anti-rabbit IgG antibody (MBL) that had been diluted 10000-fold with PBS was carried out at 37° C. for one hour. After removal of the solution, washing with PBS was performed and 100 µl of an OPD solution was reacted at room temperature for five minutes. The reaction was terminated by using 2N sulfuric acid, and the absorbance at 492 nm was measured using SpectraMax® 340PC (Molecular Devices).

As mentioned above, the result of examination on the binding ability of 46 clones collected in the above (1) showed that 40 clones (22 clones as being different in the amino acid sequence) was reactive to the botulinum toxoid. In addition, 19 kinds of clones reacted with the nontoxic protein component of the botulinum toxin.

(5) Preparation of Antibody Protein

Figure 2:
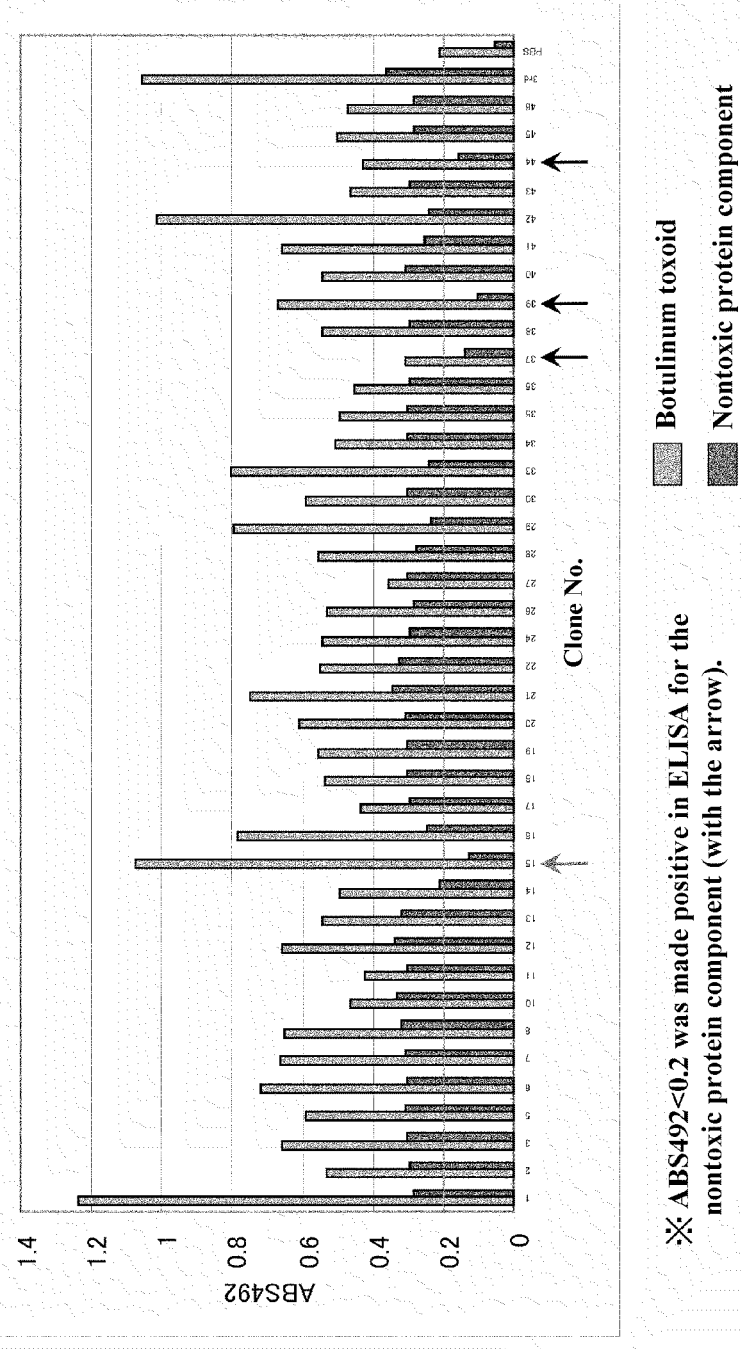
FIG. 2 shows a binding activity of the antibody obtained in screening experiment 1. A clone that showed ABS492<0.2 by ELISA against a nontoxic protein component was defined as a positive clone (shown with an arrow).

On the other hand, among the antibodies obtained by the screening using the above botulinum toxoid as an antigen, there were three antibodies that did not show the reactivity to the nontoxic protein component of the botulinum toxin, but reacted with the botulinum toxoid (FIG. 2). Note that ABS<0.2 was used as a criterion for the nontoxic protein component. BT-037 among BT-015, 37, 39, and 44 shown with an arrow, and BT-014 that is reactive with the nontoxic protein component are identical in the amino acid sequence.) After digestion of these phagemid DNAs with a restriction enzyme SalI, the digested product was converted into a Protein A fused antibody (Fab-pp type antibody) by self-recombining and then DH12S™ was transformed using this antibody. After the transformation, the transformant was cultured in 25 ml of 2xYTGA culture medium at 30° C. overnight. This culture solution 20 ml was mixed with 2 liters of 2xYTA culture medium, cultured for three hours, 2 ml of 1M IPTG was added and cultured at 30° C. for 20 hours. The culture solution was centrifuged at 8000 rpm for 10 minutes at 4° C. to collect the supernatant. After adding 1122 g of ammonium sulfate slowly to the collected supernatant, the mixture was stirred at room temperature for one hour, and centrifuged at 8500 rpm for 30 minutes at 4° C. The precipitate was suspended in 100 ml of PBS containing Complete (manufactured by Roche). Subsequently, the suspension was dialyzed against PBS at 4° C. overnight, and centrifuged at 10000 rpm for 10 minutes at 4° C. The supernatant was collected, added to a column that had been packed with 3 ml of IgG Sepharose (GE Healthcare Bioscience), and passed through the column by natural drop at room temperature. After washing the column with PBS of 300 ml, it was eluted with 6 ml of 0.2M glycine (pH 3), 3 ml of 0.2M glycine (pH 2.5) and 10 ml of 0.2M glycine (pH 3). The eluates were each adjusted to pH 7.0 with 2M Tris, placed 1 in a dialysis/concentration tube (manufactured by Millipore™, Amicon Ultra-15, 4° C., 5530 rpm rotation), and dialyzed against PBS for concentration. After that, SDS-PAGE was carried out to calculate the protein concentration.

(6) Evaluation of Antibody in Animal Test

The neutralizing ability of each antibody was evaluated by a semiquantitative test method that is to observe the symptom such as paralysis and the like in mice after mixing the isolated/prepared Fab-pp type antibody with the toxin and administering it subcutaneously to the mice. The test method was carried out according to the references (M. Takahashi et al., International Journal of Food Microbiology, 11, 271-278, 1990. Jpn. J. Med. Sci. Biol., 43, 163-170, 1990). The comparative control was prepared by diluting the botulinum toxin type-A antitoxin 10-fold (Japanese Standard: 10 units/ml) to make a stock solution and further diluting the antitoxin stock solution (1 unit/ml) with PBS by six serial 1:3 dilutions (hereinafter referred to as "standard dilution). On the other hand, the antibody solution obtained in (5) was diluted 5-fold each with PBS to make an antibody stock solution, and the stock solution was further subjected to four serial 1:5 dilutions to make a specimen (hereinafter referred to as "specimen dilution".

In addition, the botulinum neurotoxin ($3.8 \times 10^5$ LD50/ml) was diluted 400-fold to make a stock solution (950LD50/ml), and this was further diluted 500-fold to prepare a test toxin (1.9LD50/ml). The test toxin (0.25 ml) and standard dilution and specimen dilution (0.25 ml each) were accurately taken, mixed well, reacted at room temperature for one hour, and then subcutaneously inoculated into mice (one group: two mice) at a dose of 0.2 ml each, followed by three-day observation. The titer of the specimen was judged by clinical symptoms (complete remission, degree of paralysis) in the test group mice. As a result, BT-015 showed the neutralizing ability (FIG. 3).

2-2. Screening Experiment 2

Among the antibodies obtained in the screening experiment 1, a mixture of the antibody proteins of 19 clones which had been judged to be negative (antibodies that react to the nontoxic site) was prepared by the following method.

At first, DNAs of the 19 clones were mixed, digested with a restriction enzyme SalI, converted into an Fab-pp type antibody by self-recombining, and then DH12S was transformed using this antibody. After the transformation, the transformant was cultured in 100 ml of 2xYTGA culture medium at 30° C. overnight. This culture solution of 40 ml was mixed with 4 liters of 2xYTA culture medium and cultured for 3 hours, 2 ml of 1M IPTG was added and cultured at 30° C. for 20 hours. The culture solution was centrifuged at 8000 rpm for 10 minutes at 4° C. to collect a supernatant. After adding 2244 g of ammonium sulfate slowly to the collected supernatant, the mixture was stirred at room temperature for one hour, and centrifuged at 8500 rpm for 30 minutes at 4° C. The precipitate was suspended in 200 ml of PBS containing Complete (manufactured by Roche). Subsequently, the suspension was dialyzed against PBS at 4° C. overnight and centrifuged at 10000 rpm for 10 minutes at 4° C. The supernatant was collected, added to a column that had been packed with 3 ml of IgG Sepharose (GE Healthcare Bioscience), and passed through the column by natural drop at room temperature. After washing the column with 500 ml of PBS, it was eluted with 6 ml of 0.2M glycine (pH 3), 3 ml of 0.2M glycine (pH 2.5) and 10 ml of 0.2M glycine (pH 3). The eluates were each adjusted to pH 7.0 with 2M Tris, placed in a dialysis/concentration tube (manufactured by Millipore™, Amicon Ultra-15, 4° C., 5530 rpm rotation), and dialyzed against PBS for concentration. After that, SDS-PAGE was carried out to calculate the protein concentration.

Figure 4:
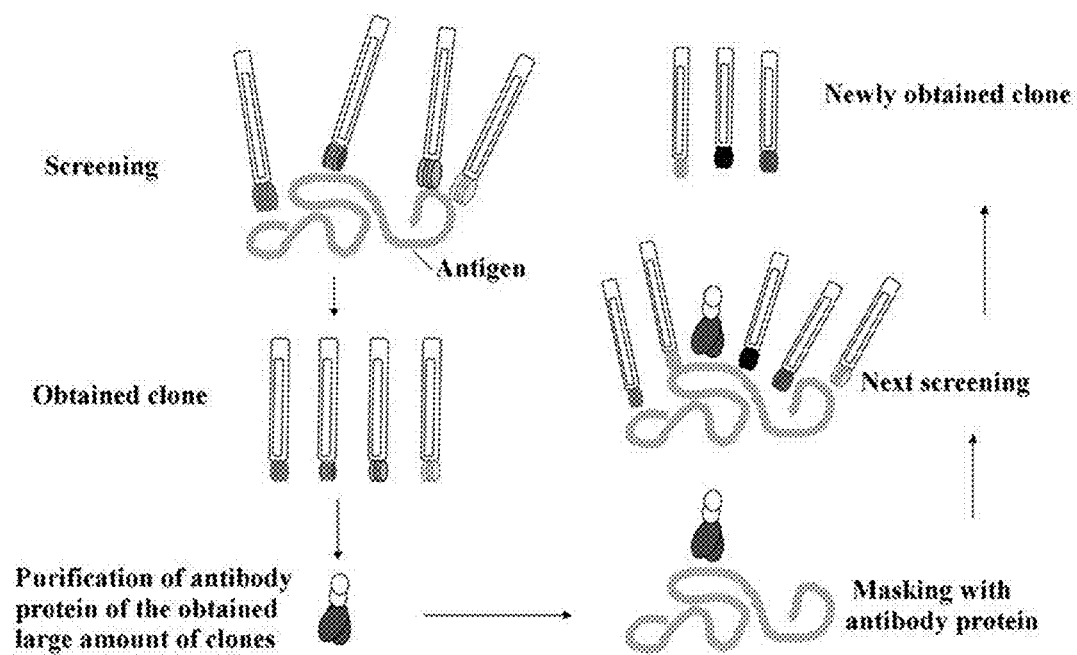
FIG. 4 shows the summary of the epitope-masking method adopted in screening experiment 2.
Figure 5:
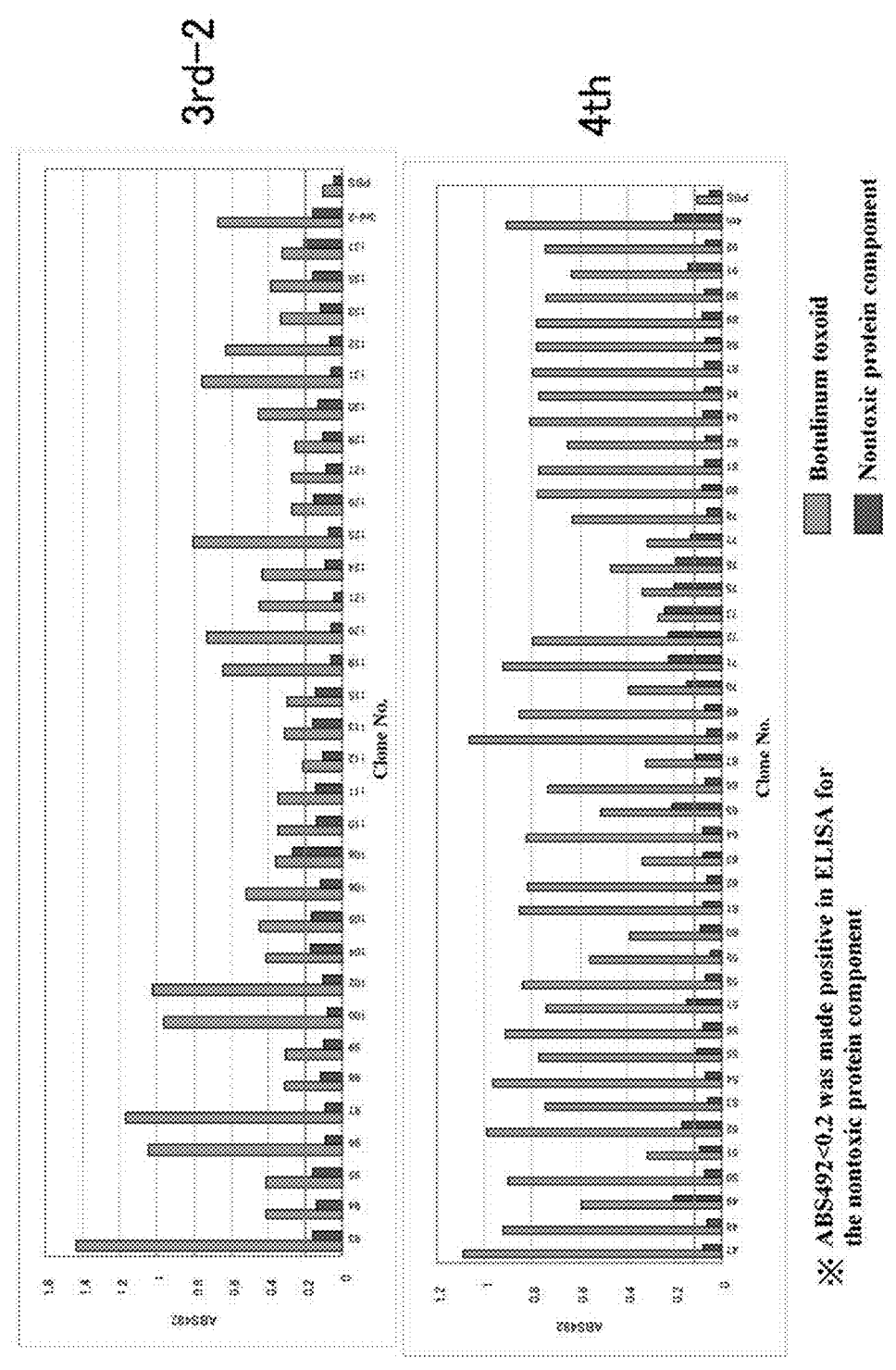

The mixed antibody proteins prepared by the above method were added in 230 µg/ml to mask the antigen (see FIG. 4), and a screening was carried out by a method similar to the screening experiment 1. As a result, 46 clones were collected. As a result of having analyzed each antibody clone by ELISA, it was revealed that 27 new antibody clones that specifically react with the toxoid were included. In this way, by masking the antigen, the antibodies that react with the nontoxic site were largely decreased (2/46) and the screening efficiency was increased (lower panel (4th) of FIG. 5).

2-3. Screening Experiment 3

It was thought that, because there were a lot of clones judged to be negative by the 3rd screening in the screening experiment 1, a bias had already been occurred at this stage and the existence ratio of the neutralizing antibodies had lowered. Therefore a screening (3rd-2) was carried out using a phage antibody (2nd phage) after the 2nd screening that was a stage in the middle of screening. At first, 100 µl each of botulinum toxoid which had been prepared to a concentration of 10 µg/ml with PBS was subdivided into 6-wells of Microcup® (manufactured by Nunc, Maxisorp®), and reacted overnight at 4° C. for immobilization. After discarding the solution, 1% BSA/PBS was subdivided in 200 µl each and blocking was performed at 37° C. for one hour. After the blocking solution was discarded, the mixed antibody protein prepared in 2-2 was subdivided in 30 µg/well, followed by reaction at 37° C. for one hour, thereby to mask the antigen. After removal of the antibody protein solution, the 2nd phage ($3.6 \times 10^{13}$ equivalents) and the mixed antibody protein prepared in 2-2 (180 µg) were mixed to be subdivided into Microcup®, and allowed to react at 37° C. for two hours. The subsequent procedure was carried out in the same manner with the above screening experiment 1.

Finally, 46 clones were picked up and the binding ability thereof was confirmed by ELISA. As a result, there were 20 novel clones that specifically reacted with the toxoid. By masking the antigen, the antibodies that react with the nontoxic site were largely decreased (1/46) and the screening efficiency was increased (upper panel of FIG. 5, third-2).

Figure 6:
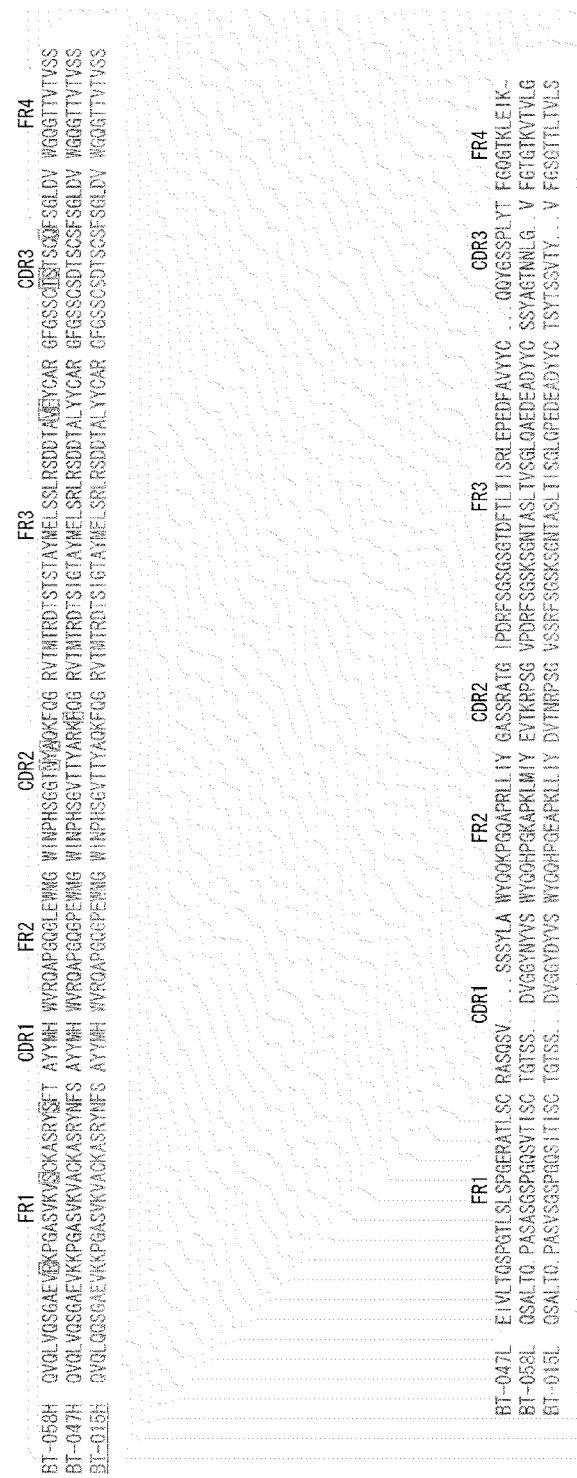
FIG. 6 shows the comparison of an amino acid sequence of the antibody obtained in screening experiment 3. From top in order.

An antibody protein was prepared from each antibody clone and a neutralization test of the toxin was performed. As a result, two clones (BT-058, BT-047) showed a neutralizing activity, but the amino acid sequence of those H-chains was almost identical as that of the clone BT-015 obtained in the screening experiment 1 (FIG. 6). Therefore, it is expected that the epitopes of these three clones are all identical.

2-4. Screening Experiment 4 (Simultaneous Performance of Collective Exclusion by Coexistence of Antibody Populations and Exclusion of Identical Clone by Antibody Coexistence)

Although an improvement was made such that a toxoid specific antibody clone has been obtained effectively by the coexistence in the screening system of the antibody which was judged to be negative, only an antibody clone that was identical to or similar to the antibody clone BT-015 obtained in the screening experiment 1 was obtained. Therefore, in order to obtain novel antibody clones, a strategy was undertaken, which is to make an antibody protein of the antibody clone BT-015 coexist in addition to the antibody proteins of 19 antibody clones which were judged to be negative so that the epitopes of these antibody clones are masked (4th-2 screening).

At first, 100 µl each of botulinum toxoid which had been prepared to a concentration of 10 µg/ml with PBS was subdivided into 6-wells of Microcup® (manufactured by Nunc, Maxisorp®), and reacted overnight at 4° C. for immobilization. After discarding the solution, 1% BSA/PBS was subdivided in 200 µl each and blocking was performed at 37° C. for one hour. After the blocking solution was discarded, the mixed antibody protein prepared in 2-2 and the antibody protein prepared from the antibody clone BT-015 were subdivided (30 µg/well each), and reacted at 37° C. for one hour, thereby to mask the antigen. After removal of the antibody protein solution, the phage (third-2 phage) of $7.2 \times 10^{12}$ equivalents obtained in the screening experiment 3, the mixed antibody protein of 180 µg prepared in 2-2, and the antibody protein of 180 µg prepared from the antibody clone BT-015 were mixed to be subdivided into Microcup®, and reacted at 37° C. for two hours. The subsequent procedure was carried out in the same manner with the above screening experiment 1.

Figure 7:
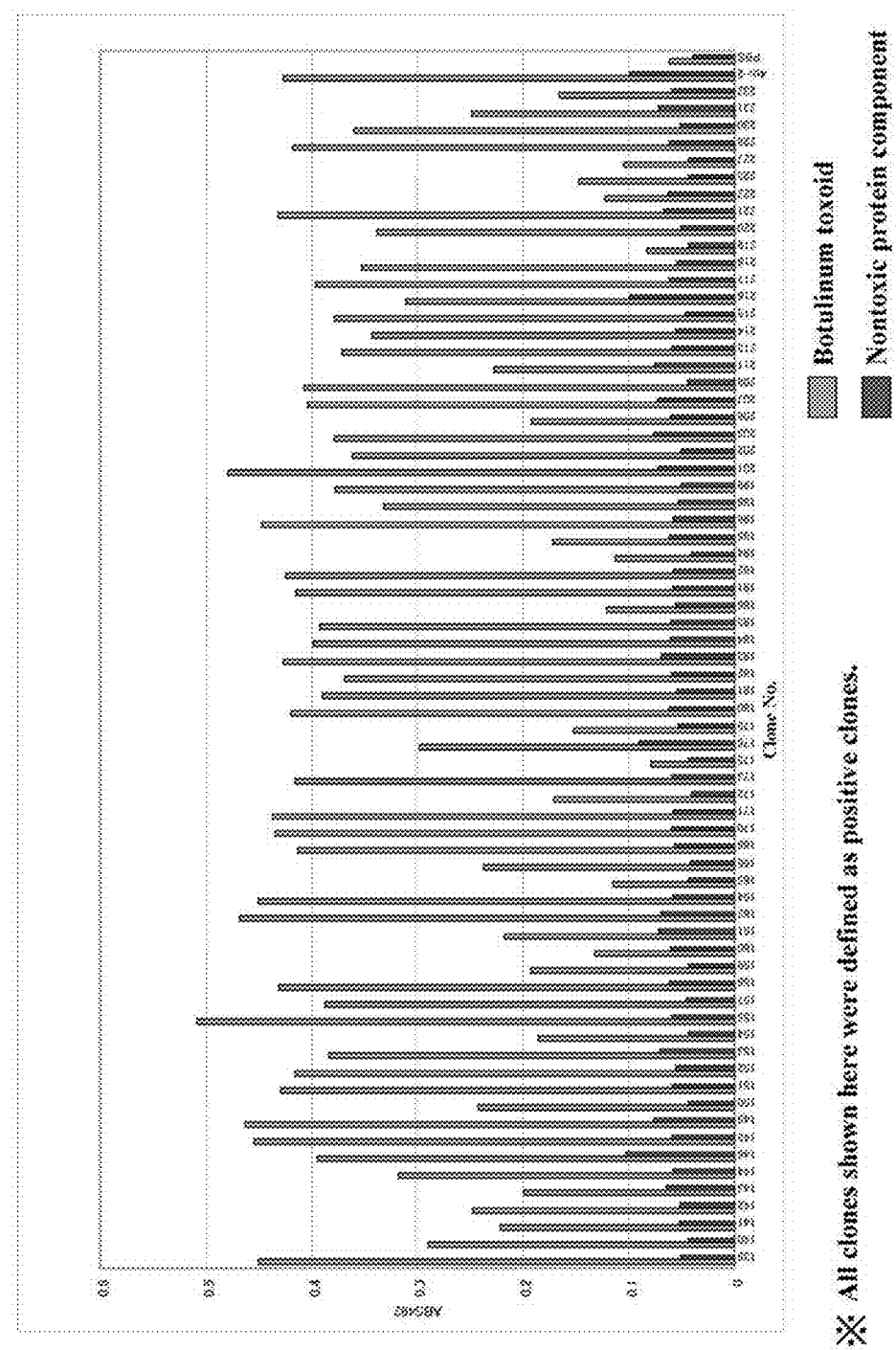
FIG. 7 shows a binding activity of the antibody obtained in screening experiment 4. All the antibody clones shown here were defined as a positive clone.

94 clones were picked up, and the binding ability thereof was confirmed by ELISA. It revealed that all of the clones reacted specifically with the toxoid (FIG. 7). Among these clones, there were 26 kinds of clones, each having a new amino acid sequence. In addition, antibodies that are identical or similar to the antibody clone BT-015 were not included. Further, the above-mentioned screening process is shown in FIG. 9.

Subsequently, the neutralizing ability of each antibody clone was evaluated by a simple test method in which symptoms such as life and death/paralysis in mice occurred when the antibody was mixed with the toxin and subcutaneously administered. Concrete test method was performed according to the reference (Japanese Minimum Requirements for Biological Products: Ministry of Health, Labour and Welfare). Fab-pp type antibodies prepared from each antibody clone were used in the test. The comparative control was prepared by diluting 10-fold the botulinum toxin type-A antitoxin (Japanese Standard: 10 units/ml) to make a stock solution as an antitoxin stock solution of 1 unit/ml, which was then diluted with PBS to 0.1 unit/ml, and is also prepared by further subjecting the stock solution to five serial 1:2 dilutions. (hereinafter referred to as "standard dilution). The prepared stock solution as it is was used as a specimen.

The botulinum neurotoxin was diluted 400-fold to make a stock solution (950LD50/ml), and this was further diluted 10-fold to prepare a test toxin (95LD50/ml). The test toxin (0.25 ml), each standard dilution, and a specimen (0.25 ml) were accurately taken, mixed well, reacted at room temperature for one hour, and then subcutaneously inoculated into the mice (one group: two mice) at a dose of 0.2 ml each, followed by four-day observation. The titer of the specimen was judged by clinical symptoms (complete remission, degree of paralysis) in the test group mice. As a result, antibody clone BT-175 showed a neutralizing ability (FIG. 8).

2-5. Screening Experiment 5 (Screening with the Use of Botulinum Neurotoxin Type-A)

Botulinum toxin was purified from *Clostridium botulinum* strain 627A from which nontoxic protein components were discarded to yield a purified neurotoxin (active center of the toxin: 150 kDa) according to the literature (INFECTION AND IMMUNITY, Vol. 12, No. 6. December 1975, p. 1262-1270). A screening using this neurotoxin as an antigen was carried out to obtain a neutralizing antibody that recognizes an epitope different from those of the antibody clones BT-015 and BT-175.

At first, 100 µl each of botulinum neurotoxin which had been prepared to a concentration of 10 µg/ml with PBS was subdivided into 6-wells of Microcup, and reacted overnight at 4° C. for immobilization. After discarding the solution, 1% BSA/PBS was subdivided in 200 µl each and blocking was performed at 37° C. for one hour. After the blocking solution was discarded, a human antibody library of $1.0 \times 10^{13}$ were subdivided (130 µl/well) and reacted at 37° C. for two hours. The subsequent procedure was the same with the above screening experiment 1 (screening was performed until the 4th screening. In the 4th screening, 400 µl of the 3rd phage was used).

Figure 10:
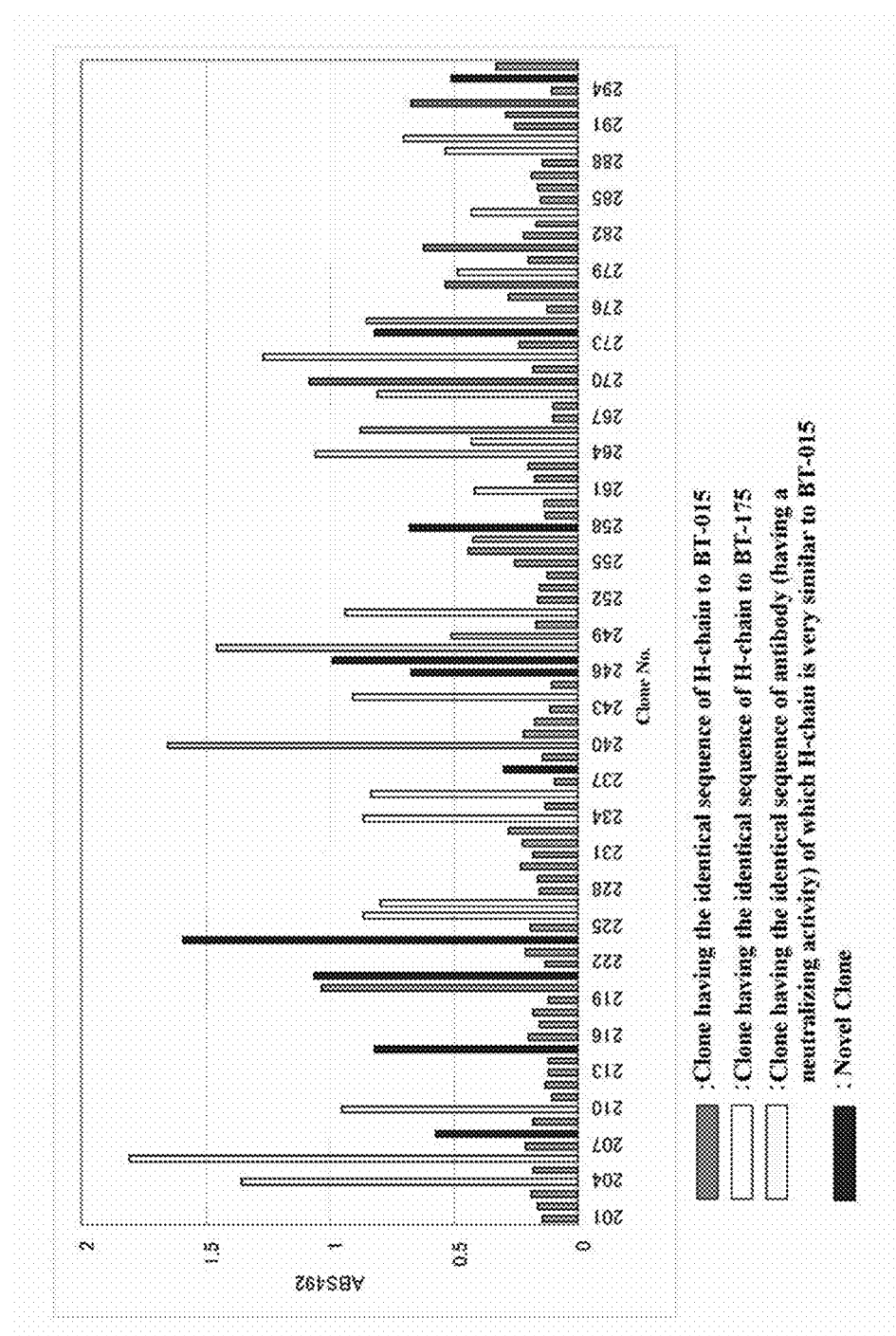
FIG. 10 shows a binding activity of the antibody obtained in screening experiment 5.
Figure 11:
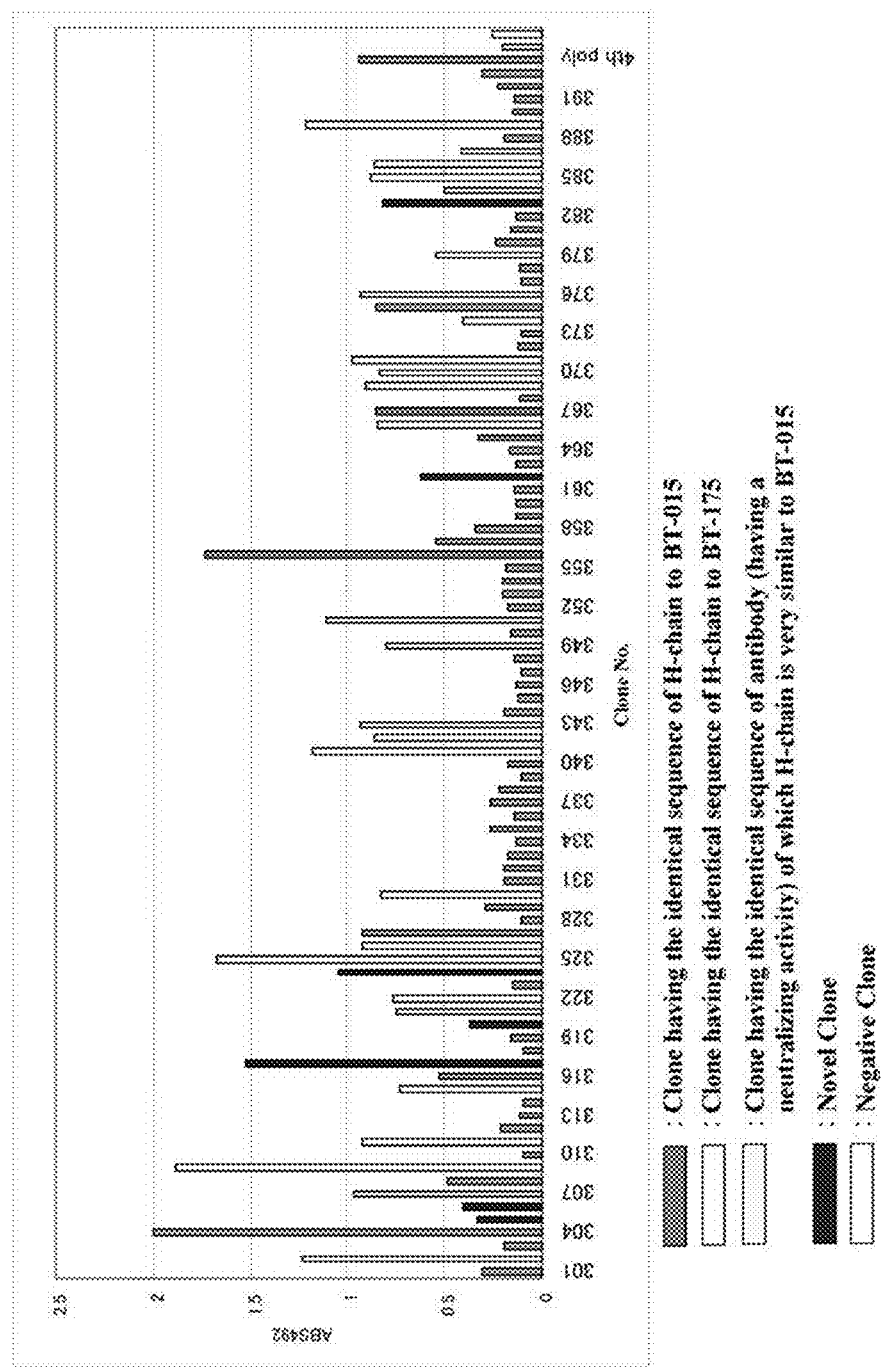
FIG. 11 shows a binding activity of the antibody obtained in screening experiment 5.

After the 4th screening was performed, 188 clones were picked up, and the binding ability thereof was confirmed by ELISA. As a result, there were six kinds of clones that reacted specifically with the toxoid (FIGS. 10 and 11). Among them, a lot of clones that are identical or similar to two kinds of antibody clones (BT-015, BT-0175) which had been obtained so far (6 clones for BT-015 and 5 clones for BT-175) were included.

2-6. Screening Experiment 6 (Exclusion of Identical Clone by Coexistence of BT-015 and BT-175 Antibodies)

A screening experiment was further carried out for the purpose of excluding a lot of antibody clones (clones that are identical or similar to BT-015 or BT-175) obtained even in the screening (2-5) using neurotoxin as an antigen.

Figure 12:
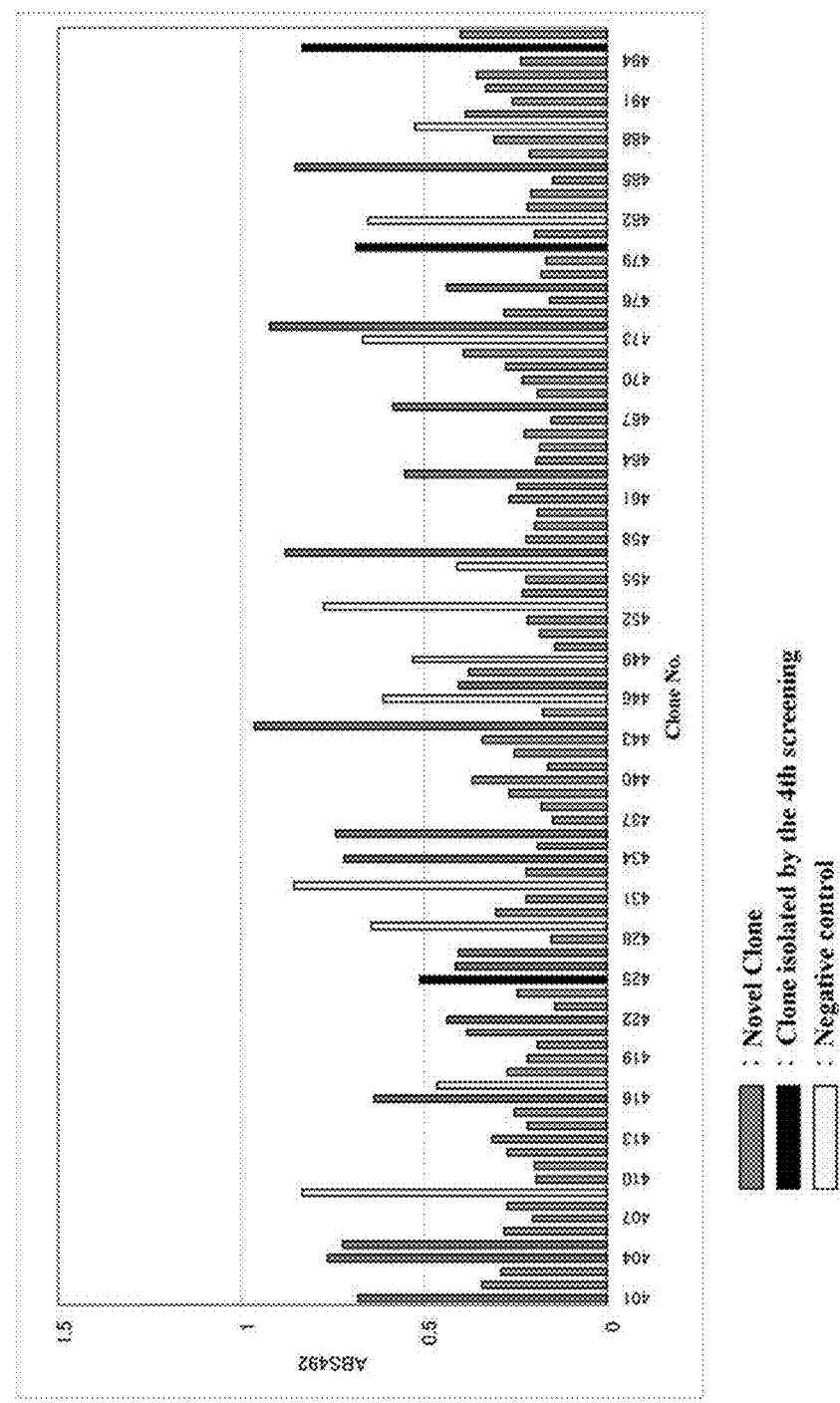
FIG. 12 shows a binding activity of the antibody obtained in screening experiment 6.
Figure 13:
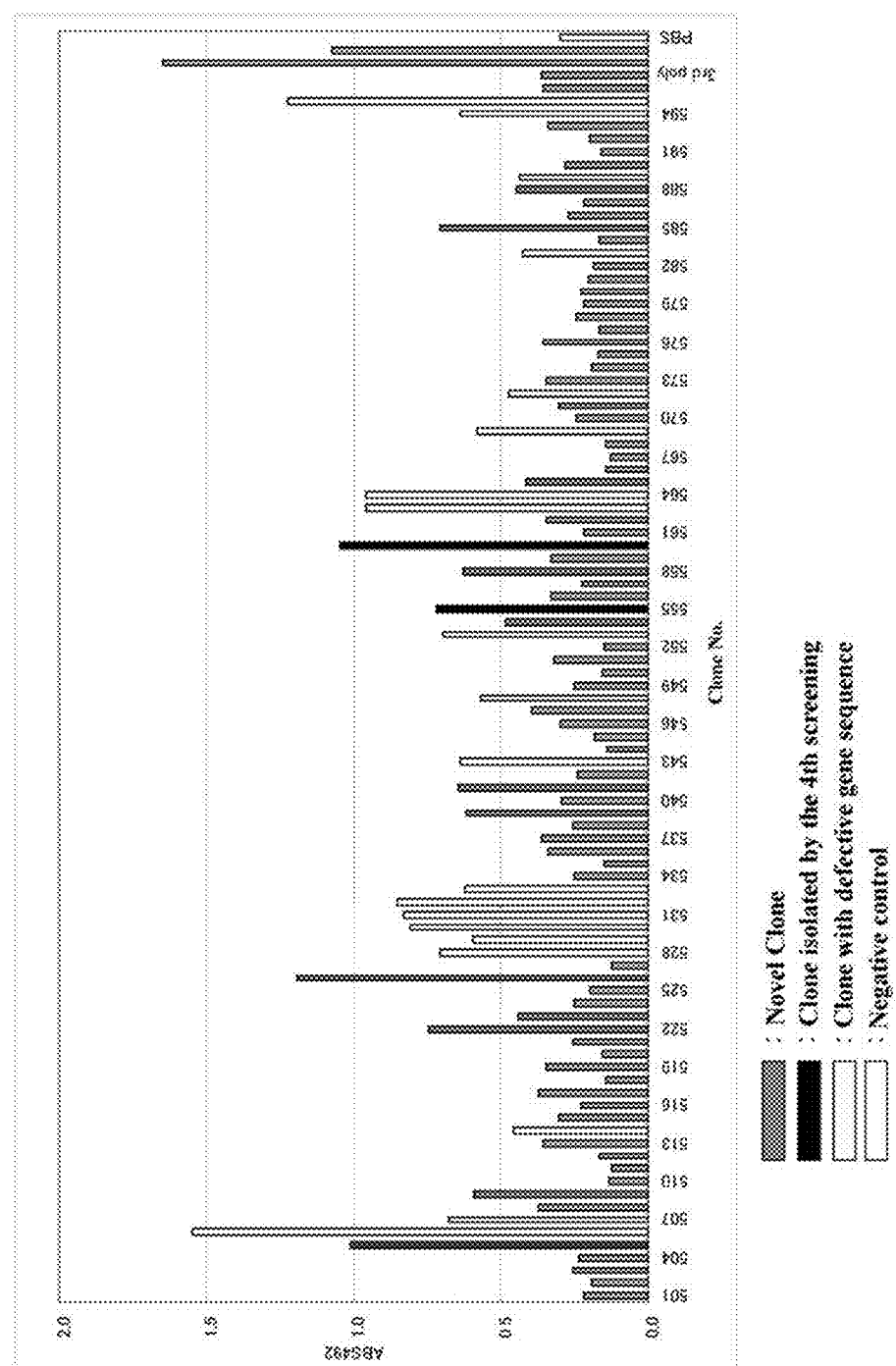
FIG. 13 shows a binding activity of the antibody obtained in screening experiment 6.

At first, 100 µl each of neurotoxin which had been prepared to a concentration of 10 µg/ml with PBS was subdivided into 8-wells of Microcup® and reacted overnight at 4° C. for immobilization. After discarding the solution, 1% BSA/PBS was subdivided in 200 µl each and blocking was performed at 37° C. for one hour. After discarding the blocking solution, an antibody protein prepared from the antibody clones BT-015 and BT-175 were subdivided (30 µg/well each) and reacted at 37° C. for one hour, thereby to mask the antigen. After removal of the antibody protein solution, the phage (3rd phage) of $2.0 \times 10^{13}$ obtained in the 3rd screening of the screening experiment 5, and the antibody protein prepared from the antibody clones BT-015 and BT-175 were mixed (180 µg each), subdivided into Microcup®, and allowed to react at 37° C. for two hours. 188 clones were picked up, and the binding ability thereof was confirmed by ELISA. It revealed that there were 24 kinds of clones that reacted specifically with neurotoxin (FIGS. 12 and 13). Further, the above screening process is shown in FIG. 15.

2-7. Evaluation of Antibodies by Animal Test

Fab-pp type antibodies were prepared from 30 kinds of antibody clones obtained in the screening (screening experiments 5 and 6) using neurotoxin as an antigen. The neutralizing ability of each Fab-pp type antibodies was evaluated by a test method in which symptoms such as life and death/paralysis in mice occurred when the antibody was mixed with the toxin and subcutaneously administered were observed. The test method was carried out according to the reference (Japanese Minimum Requirements for Biological Products: Ministry of Health, Labour and Welfare, The Japanese Pharmacopoeia), and the titer of the specimen was determined as a relative value to Japanese Standard. The botulinum toxin type-A antitoxin (Japanese Standard: 10 units/ml) was diluted 10-fold to make a stock solution that is an antitoxin stock solution (1 unit/ml), which was diluted with PBS to prepare a dilution of 0.1 unit/ml, and further five serial 1:2 dilutions were also prepared (hereinafter referred to as "standard dilution). The prepared stock solution as it is was used as a specimen.

Figure 14:
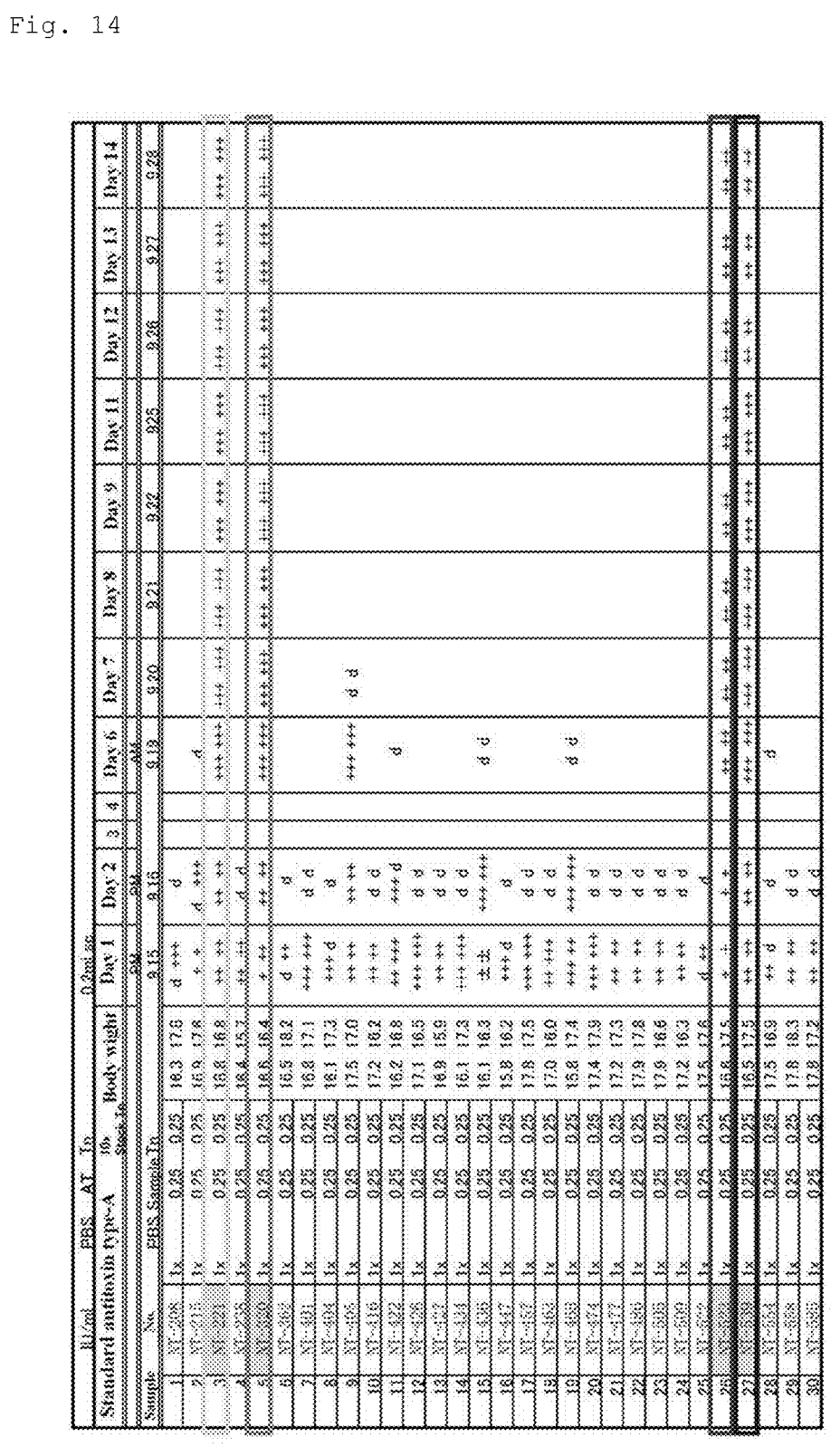

In addition, the botulinum neurotoxin was diluted 400-fold to make a stock solution (950LD50/ml), and this was further diluted 10-fold to prepare a test toxin (95LD50/ml). The test toxin (0.25 ml), each standard dilutions, and a specimen (0.25 ml) were accurately taken, mixed well, reacted at room temperature for one hour, and then subcutaneously inoculated into the mice (one group: two mice) at a dose of 0.2 ml each, followed by 40-day observation. The titer of the specimen was judged by clinical symptoms (complete remission, degree of paralysis) in the test group mice. As a result, four kinds of antibody clones (NT-221, NT-320, NT-523, NT-539) showed a neutralizing ability (FIG. 14).

3. Comparison of Antibody Sequences

The sequence information of the antibodies obtained in the above screenings (screening experiments 1 to 6) are shown below. In FIG. 16, the amino acid sequences of these antibodies (with the proviso that BT-047 and BT-058 which are each a similar clone of BT-015 were excluded) were compared and their homologies to Germline were shown.

(1) BT-015
(Amino acid sequence)

| | |
|---|---|
| VH CDR1: | SEQ ID NO: 1 |
| VH CDR2: | SEQ ID NO: 2 |
| VH CDR3: | SEQ ID NO: 3 |
| VH: | SEQ ID NO: 4 |
| VL CDR1: | SEQ ID NO: 5 |
| VL CDR2: | SEQ ID NO: 6 |
| VL CDR3: | SEQ ID NO: 7 |
| VL: | SEQ ID NO: 8 |

(Base sequence)

| | |
|---|---|
| VH: | SEQ ID NO: 65 |

-continued

| | |
|---|---|
| VL: | SEQ ID NO: 66 |
| (2) BT-047 | |
| (Amino acid sequence) | |
| VH CDR1: | SEQ ID NO: 9 |
| VH CDR2: | SEQ ID NO: 10 |
| VH CDR3: | SEQ ID NO: 11 |
| VH: | SEQ ID NO: 12 |
| VL CDR1: | SEQ ID NO: 13 |
| VL CDR2: | SEQ ID NO: 14 |
| VL CDR3: | SEQ ID NO: 15 |
| VL: | SEQ ID NO: 16 |
| (Nucleotide sequence) | |
| VH: | SEQ ID NO: 67 |
| VL: | SEQ ID NO: 68 |
| (3) BT-058 | |
| (Amino acid sequence) | |
| VH CDR1: | SEQ ID NO: 17 |
| VH CDR2: | SEQ ID NO: 18 |
| VH CDR3: | SEQ ID NO: 19 |
| VH: | SEQ ID NO: 20 |
| VL CDR1: | SEQ ID NO: 21 |
| VL CDR2: | SEQ ID NO: 22 |
| VL CDR3: | SEQ ID NO: 23 |
| VL: | SEQ ID NO: 24 |
| (Nucleotide sequence) | |
| VH: | SEQ ID NO: 69 |
| VL: | SEQ ID NO: 70 |
| (4) NT-221 | |
| (Amino acid sequence) | |
| VH CDR1: | SEQ ID NO: 25 |
| VH CDR2: | SEQ ID NO: 26 |
| VH CDR3: | SEQ ID NO: 27 |
| VH: | SEQ ID NO: 28 |
| VL CDR1: | SEQ ID NO: 29 |
| VL CDR2: | SEQ ID NO: 30 |
| VL CDR3: | SEQ ID NO: 31 |
| VL: | SEQ ID NO: 32 |
| (Nucleotide sequence) | |
| VH: | SEQ ID NO: 71 |
| VL: | SEQ ID NO: 72 |
| (5) BT-175 | |
| (Amino acid sequence) | |
| VH CDR1: | SEQ ID NO: 33 |
| VH CDR2: | SEQ ID NO: 34 |
| VH CDR3: | SEQ ID NO: 35 |

-continued

| | |
|---|---|
| VH: | SEQ ID NO: 36 |
| VL CDR1: | SEQ ID NO: 37 |
| VL CDR2: | SEQ ID NO: 38 |
| VL CDR3: | SEQ ID NO: 39 |
| VL: | SEQ ID NO: 40 |
| (Nucleotide sequence) | |
| VH: | SEQ ID NO: 73 |
| VL: | SEQ ID NO: 74 |
| (6) NT-320 | |
| (Amino acid sequence) | |
| VH CDR1: | SEQ ID NO: 41 |
| VH CDR2: | SEQ ID NO: 42 |
| VH CDR3: | SEQ ID NO: 43 |
| VH: | SEQ ID NO: 44 |
| VL CDR1: | SEQ ID NO: 45 |
| VL CDR2: | SEQ ID NO: 46 |
| VL CDR3: | SEQ ID NO: 47 |
| VL: | SEQ ID NO: 48 |
| (Nucleotide sequence) | |
| VH: | SEQ ID NO: 75 |
| VL: | SEQ ID NO: 76 |
| (7) NT-523 | |
| (Amino acid sequence) | |
| VH CDR1: | SEQ ID NO: 49 |
| VH CDR2: | SEQ ID NO: 50 |
| VH CDR3: | SEQ ID NO: 51 |
| VH: | SEQ ID NO: 52 |
| VL CDR1: | SEQ ID NO: 53 |
| VL CDR2: | SEQ ID NO: 54 |
| VL CDR3: | SEQ ID NO: 55 |
| VL: | SEQ ID NO: 56 |
| (Nucleotide sequence) | |
| VH: | SEQ ID NO: 77 |
| VL: | SEQ ID NO: 78 |
| (8) NT-539 | |
| (Amino acid sequence) | |
| VH CDR1: | SEQ ID NO: 57 |
| VH CDR2: | SEQ ID NO: 58 |
| VH CDR3: | SEQ ID NO: 59 |
| VH: | SEQ ID NO: 60 |
| VL CDR1: | SEQ ID NO: 61 |
| VL CDR2: | SEQ ID NO: 62 |
| VL CDR3: | SEQ ID NO: 63 |
| VL: | SEQ ID NO: 64 |

-continued (Nucleotide sequence)
VH:                        SEQ ID NO: 79

VL:                        SEQ ID NO: 80

4. Analysis of Antibody 4-1. Preparation of IgG Antibody

IgG antibodies were prepared from antibody clones (BT-015, BT-175, NT-221, NT-320, NT-523) wherein a neutralizing activity was observed in the Fab-pp type antibody. At first, as for each antibody clone, a gene fragment encoding VH is ligated to a human γ1 chain constant region DNA and integrated into an expression vector "BCMGS Neo vector" (Hajime Karasuyama, "Bovine Papillomavirus Vector", Edited by Masami Muramatsu and Hiroto Okayama, Jikken Igaku (Experimental Medicine), Suppl. Gene Engineering Handbook, Published by Yodosha Co., Ltd., pp. 297-299 (1991)) to make an H-chain vector with the constant region. Similarly, a full L-chain gene of each antibody clone is integrated into a vector to make an antibody expression vector for L-chain expression.

The antibody expression vectors were transfected into a Chinese hamster cell strain CHO-K1 using the Lipofectin method, and the cells were cultured at 37° C. for a given time, and transplanted in a 96-well plate to select a high expression cell. Each cell selected was cultured for two weeks in a large scale culture flask (CELLine™ 1000 Flask, manufactured by Becton Dickinson) using a serum-free culture medium (CHO-S-SFM II: manufactured by Invitrogen™, 1% (v/v) Penicillin-Streptomycin Solution: manufactured by Sigma-Aldrich®, 700 µg/ml G418: manufactured by Sigma-Aldrich®). The culture supernatant was collected, and supplied to a protein G binding affinity column. The column was washed with PBS, eluted with a glycine hydrochloric acid buffer solution (pH 2.7), and neutralized with a Tris-HCl buffer solution (pH 8.9). Then, the eluate was placed in a dialysis/concentration tube (Amicon Ultra-15, manufactured by Millipore™), and dialyzed against PBS for concentration. The thus obtained IgG type antibody was used in the subsequent experiment.

4-2. Binding Constant Analysis by Biacore

Figure 17:
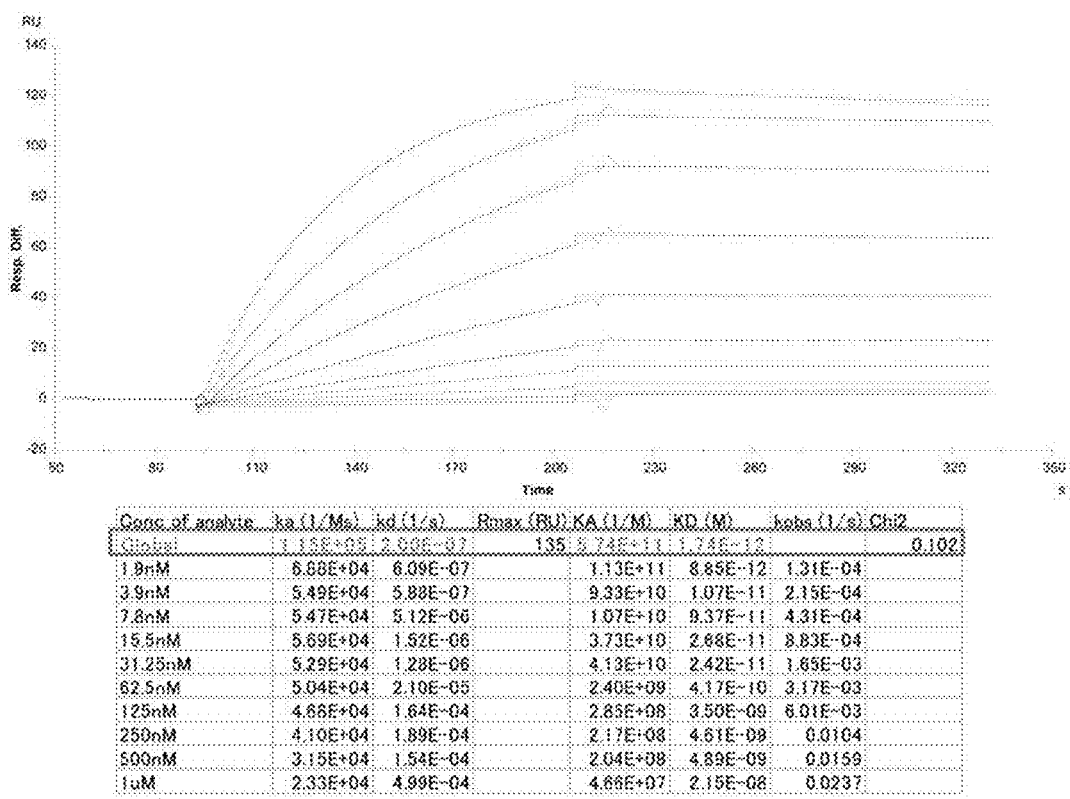
FIG. 17 shows the result of binding constant analysis by Biacore (the sample is an Fab-PP type antibody of BT-015).
Figure 18:
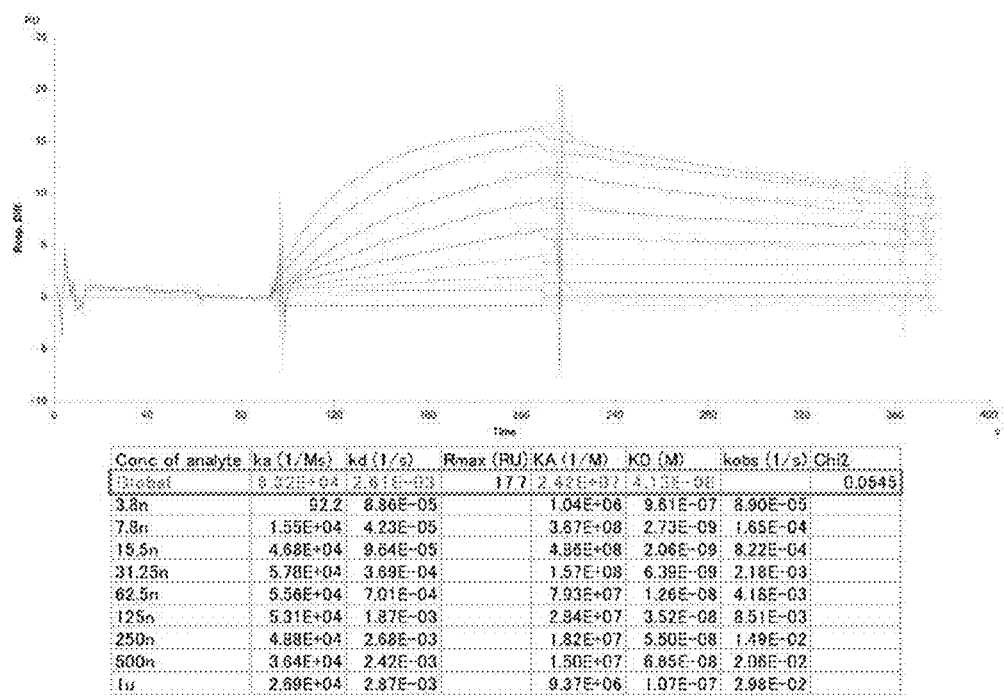
FIG. 18 shows the result of binding constant analysis by Biacore (the sample is an IgG type-antibody of BT-015).
Figure 19:
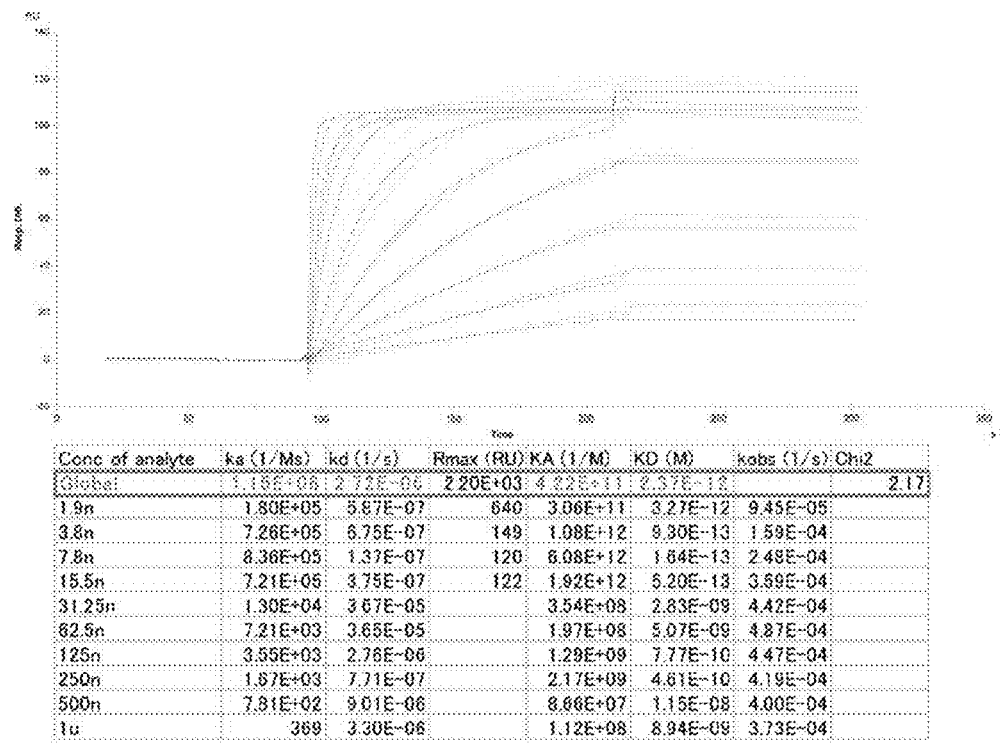
FIG. 19 shows the result of binding constant analysis by Biacore (the sample is an Fab-PP type-antibody of BT-175).
Figure 20:
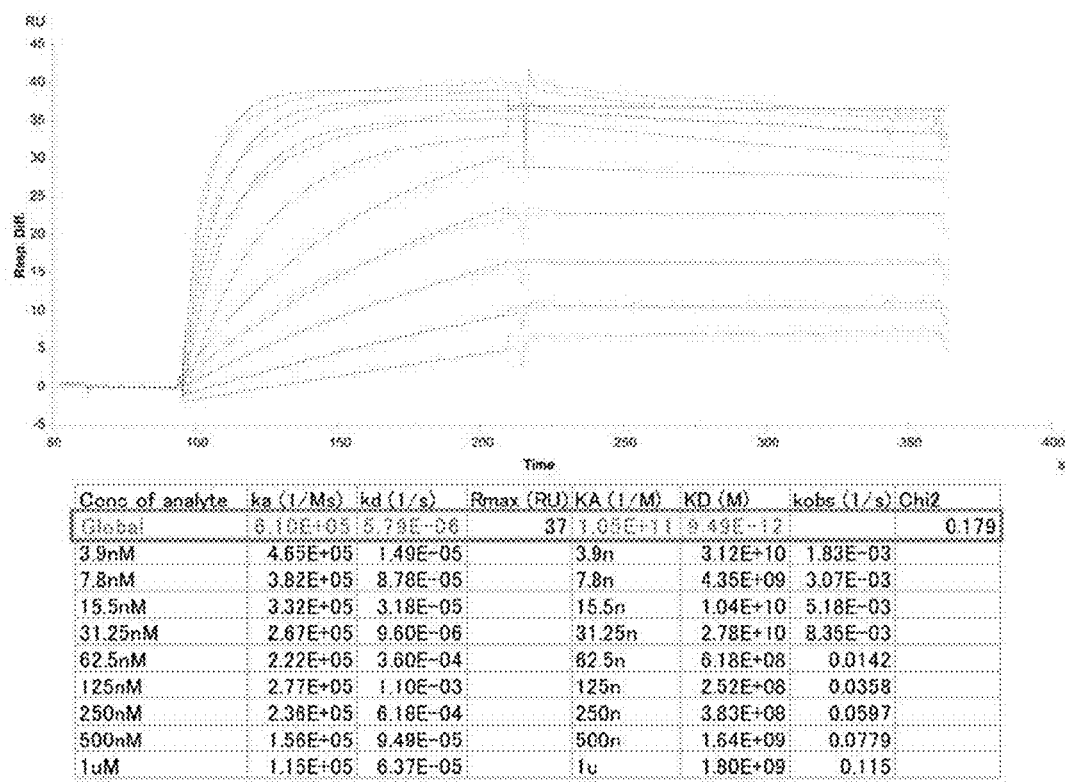
FIG. 20 shows the result of binding constant analysis by Biacore (the sample is an IgG type-antibody of BT-175).
Figure 21:
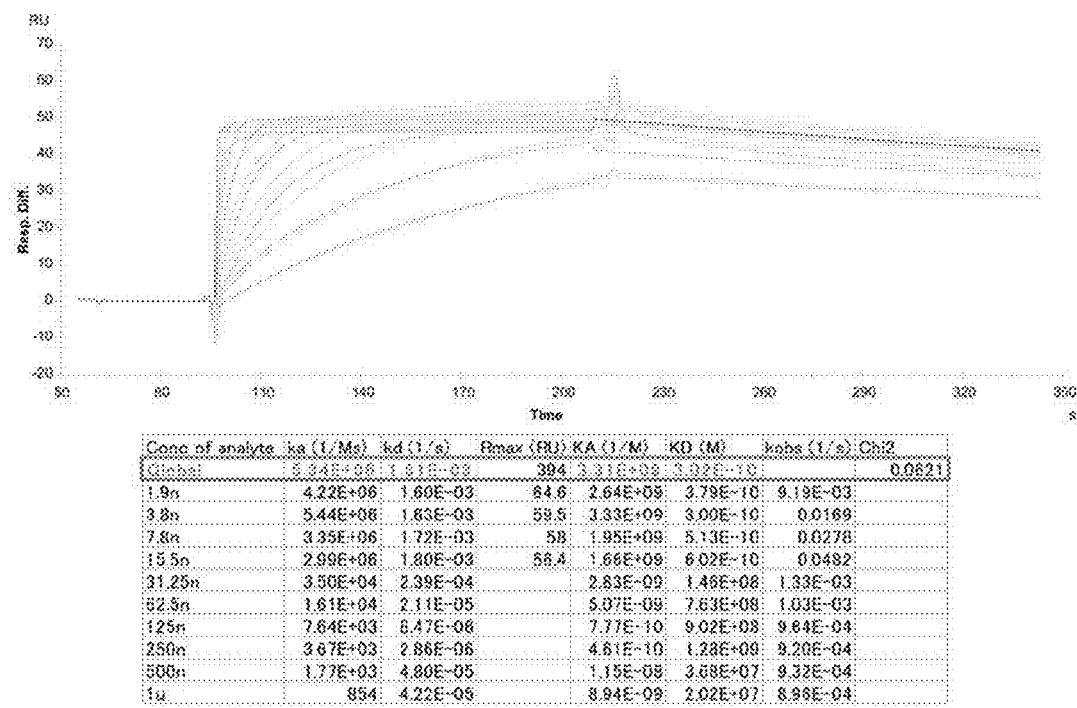
FIG. 21 shows the result of binding constant analysis by Biacore (the sample is a Fab-PP type-antibody of NT-221).
Figure 22:
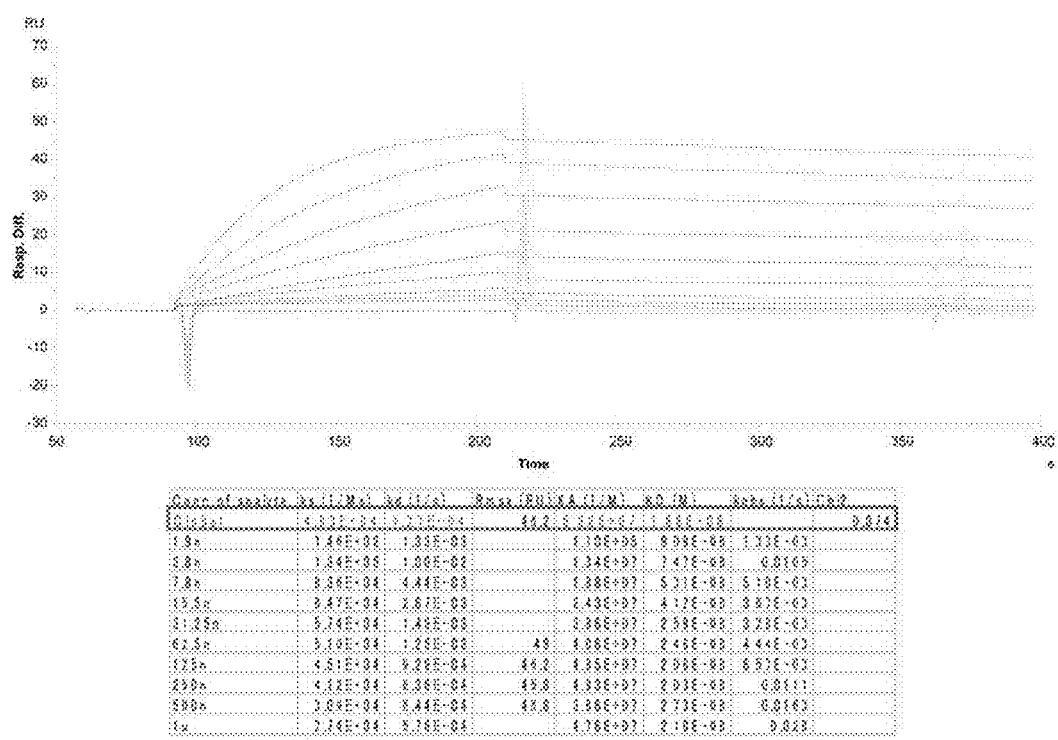
FIG. 22 shows the result of binding constant analysis by Biacore (the sample is a Fab-PP type-antibody of NT-320).

A biosensor device Biacore3000 was used for analysis. At first neurotoxin 880RU was immobilized to a sensor chip (CM5) and Fab-PP type or IgG type antibody with a sequentially varying concentration (1.9 nM to 1 µM) was injected (40 µl, two minutes). The analysis results are shown in FIG. 17 (Fab-PP type antibody of BT-015), FIG. 18 (IgG type antibody of BT-015), FIG. 19 (Fab-PP type antibody of BT-175), FIG. 20 (IgG type antibody of BT-175), FIG. 21 (Fab-PP type antibody of NT-221), and FIG. 22 (Fab-PP type antibody of NT-320). As a result of analysis, all the antibodies were found to have the excellent binding strength.

4-3. Epitope Analysis by Biacore

Fab-PP type antibodies of six kinds of antibody clones (BT-015, BT-175, NT-221, NT-320, NT-523, NT-539) that showed a neutralizing activity against botulinum toxin type-A were prepared, and a competitive experiment was carried out by Biacore using these antibodies. Neurotoxin 800RU was immobilized to a sensor chip (CM5) and the antibodies were sequentially injected at the concentration shown below, to determine the presence or absence of the competition. The injection was flowed at a rate of 40 µl (two minutes). All analysis experiments were carried out at 25° C. in HBS-EP (Biacore) at an HBS-EP flow rate of 20 µl/min. The regeneration was performed with 20 µl (flow rate: 60 µl/min, 20 seconds) of 100 mM glycine-HCl (pH 2.0).

TABLE 1

Injection concentration of antibody (alone or combinatio; final concentration)

Figure 23:
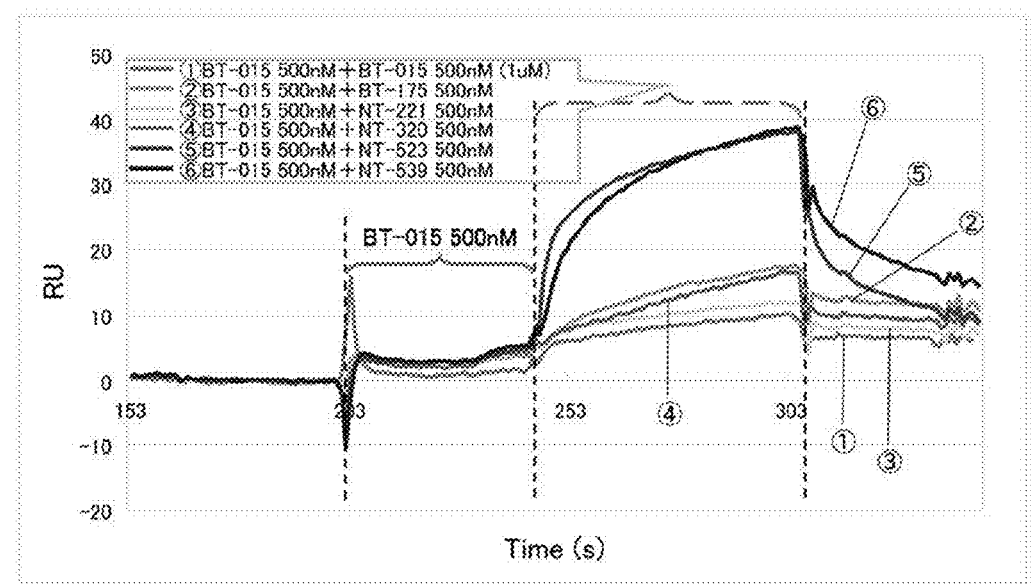
FIG. 23 shows the result of competitive experiment by Biacore (competition with BT-015). It was suggested that BT-015 competed with NT-221.
Figure 24:
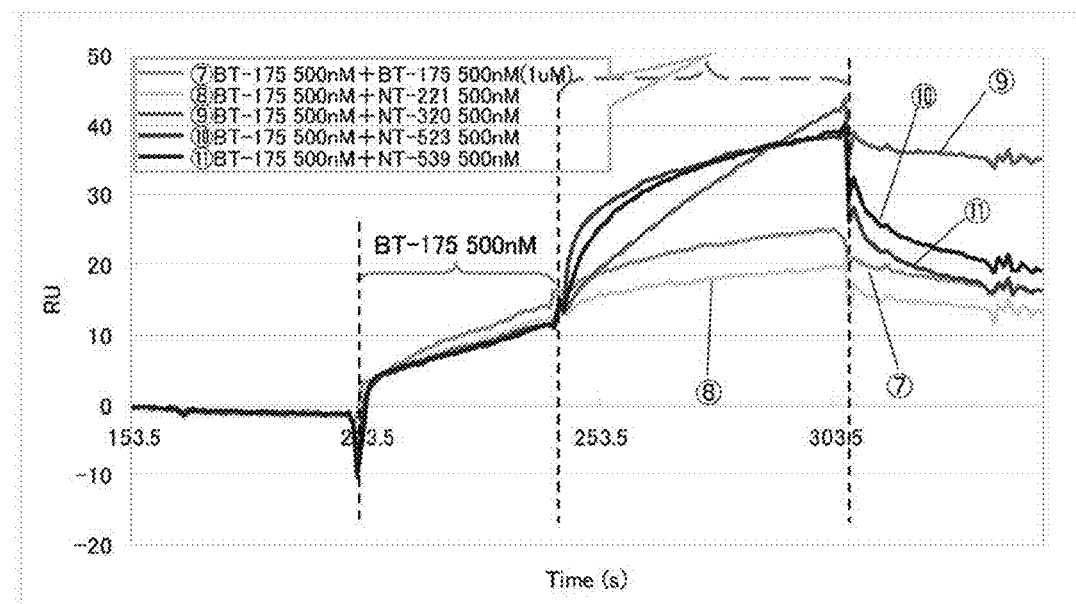
FIG. 24 shows the result of competitive experiment by Biacore (competition with BT-175). It was suggested that BT-175 competed with NT-221.
Figure 25:
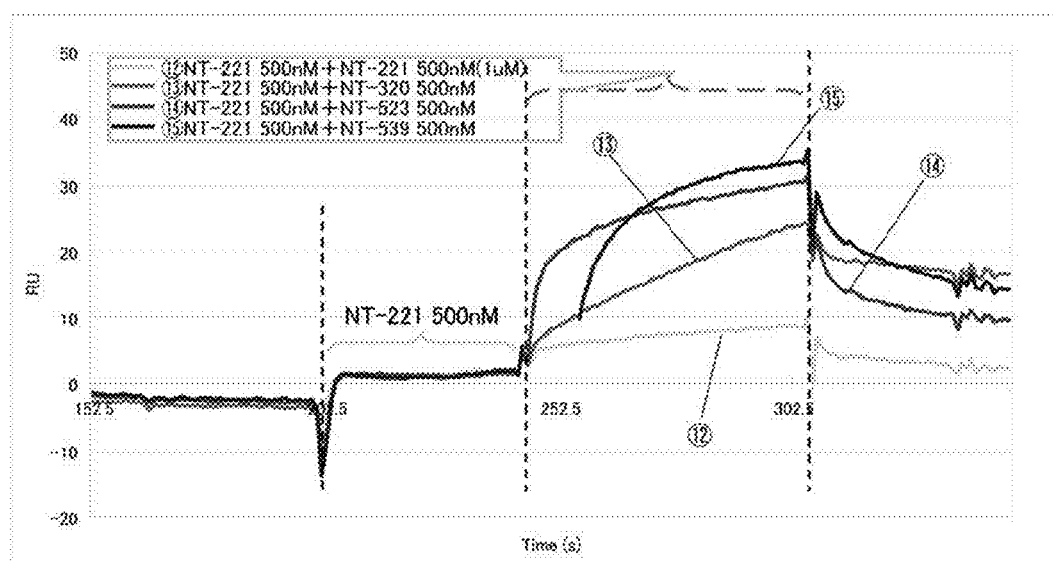
FIG. 25 shows the result of competitive experiment by Biacore (competition with NT-221). Because a strong noise was generated at about 250 sec in the case of NT-539, the region was deleted.
Figure 26:
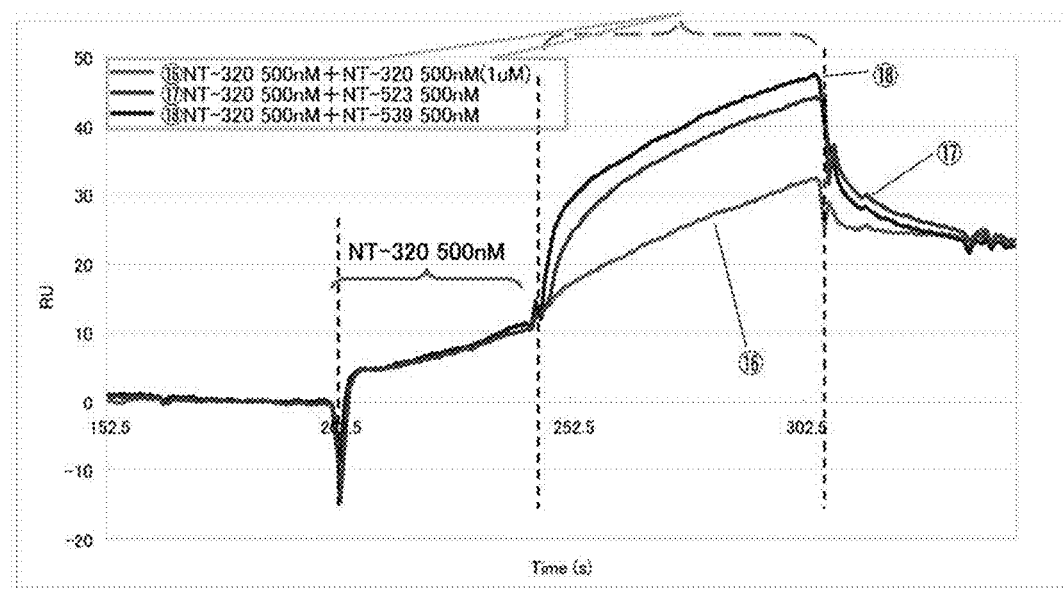
FIG. 26 shows the result of competitive experiment by Biacore (competition with NT-320).
Figure 27:
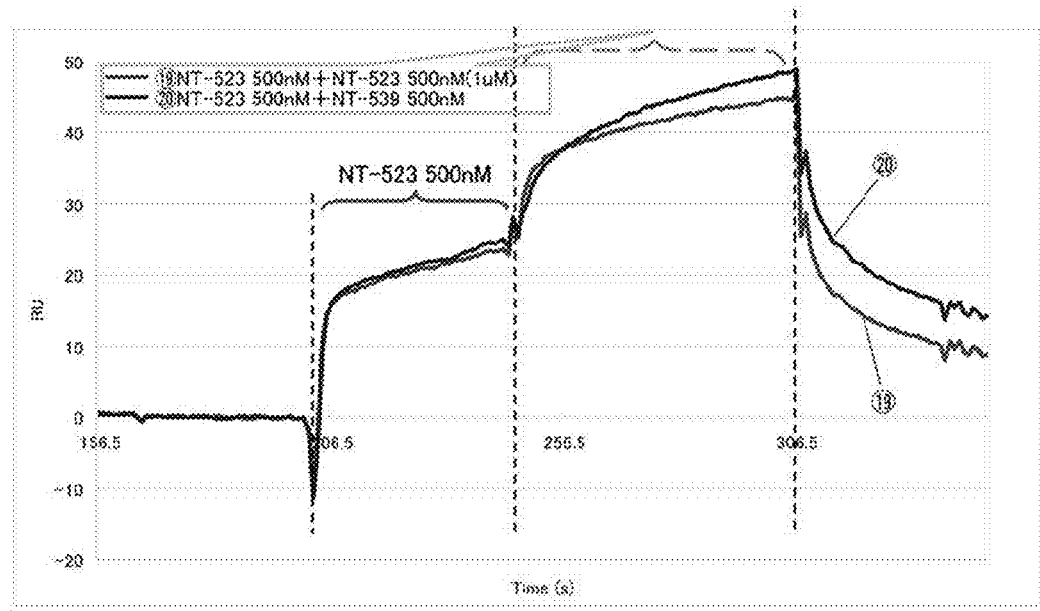
FIG. 27 shows the result of competitive experiment by Biacore (competition with NT-523). It was suggested that NT-523 competed with NT-539.

| Competitive Experiment 1 Competitive Reaction with BT-015 FIG. 23 | | Competitive Experiment 2 Competitive Reaction with BT-175 FIG. 24 | | Competitive Experiment 3 Competitive Reaction with NT-221 FIG. 25 | | Competitive Experiment 4 Competitive Reaction with NT-320 FIG. 26 | | Competitive Experiment 5 Competitive Reaction with NT-523 FIG. 27 | |
|---|---|---|---|---|---|---|---|---|---|
| Sample No. | Sample concentration | Sample No. | Sample concentration | Sample No. | Sample concentration | Sample No. | Sample concentration | Sample No. | Sample concentration |
| ① | BT-015 500 nM BT-015 1 µM | ⑦ | BT-175 500 nM BT-175 1 µM | ⑫ | NT-221 500 nM NT-221 1 µM | ⑯ | NT-320 500 nM NT-320 1 µM | ⑲ | NT-523 500 nM NT-523 1 µM |
| ② | BT-015 500 nM BT-015 500 nM + BT-175 500 nM | ⑧ | BT-175 500 nM BT-175 500 nM + NT-221 500 nM | ⑬ | NT-221 500 nM NT-221 500 nM + NT-320 500 nM | ⑰ | NT-320 500 nM NT-320 500 nM + NT-523 500 nM | ⑳ | NT-523 500 nM NT-523 500 nM + NT-539 500 nM |
| ③ | BT-015 500 nM BT-015 500 nM + NT-221 500 nM | ⑨ | BT-175 500 nM BT-175 500 nM + NT-320 500 nM | ⑭ | NT-221 500 nM NT-221 500 nM + NT-523 500 nM | ⑱ | NT-320 500 nM NT-320 300 nM + NT-539 500 nM | | |
| ④ | BT-015 500 nM BT-015 500 nM + NT-320 500 nM | ⑩ | BT-175 500 nM BT-175 500 nM + NT-523 500 nM | ⑮ | NT-221 500 nM NT-221 500 nM + NT-539 500 nM | | | | |
| ⑤ | BT-015 500 nM BT-015 500 nM + NT-523 500 nM | ⑪ | BT-175 500 nM BT-175 500 nM + NT-539 500 nM | | | | | | |
| ⑥ | BT-015 500 nM BT-015 500 nM + NT-539 500 nM | | | | | | | | |

The results of the competitive experiments by Biacore were shown in FIGS. 23 to 27. On the other hand, the presence or absence of the competition between the antibodies was confirmed by ELISA. From the results of ELISA, it was confirmed that BT-015 and NT-221 were not competitive, but BT-175 and NT-221 were competitive. As a result of having judged the results of Biacore and ELISA comprehensively, six kinds of antibodies were classified into four categories by the difference of epitopes. In addition, the H-chain amino acid sequence of each of BT-047 and BT-058 is almost identical to that of the clone BT-015 and it is expected that the epitopes of these three clones are identical from each other.

TABLE 2

Clasification of epitopes

| BT-015 | BT-175, NT-221 (Identical or Neighbouring Epitope) | NT-320 | NT-523, NT-539 (Identical or Neighbouring Epitope) |

4-4. Neutralization Test (Neutralization Test with IgG Antibody. L+/20 Level)

By using IgG type antibodies prepared from each antibody clone, a neutralization test was carried out according to Minimum Requirements for Biological Products.

At first, a botulinum type-A Japanese standard was diluted to prepare five serial dilutions (hereinafter referred to as "Standard Dilution") containing a suitable interval concentration unit in consideration of test accuracy mainly on 0.050 units in 0.25 ml. In addition, the same dilutions (hereinafter referred to as "Specimen Dilution") were prepared by diluting an IgG type antibody. Furthermore, a test toxin type-A was diluted to prepare a solution containing one test toxin amount in 0.25 mL (hereinafter referred to as "Toxin Dilution"). Each standard dilution and specimen dilution, and each toxin dilution were taken accurately in an equal amount, and they were mixed well and allowed to stand for one hour. Four mice of 23-29 days age were used as one group, and the dose 0.5 ml of the mixed solution per one mouse was intraperitoneally injected, using one group for each mixed solution. After that, observation was continued for three days to calculate the relative value to the standard product.

Among six kinds of antibody clones, a complete neutralization was not recognized in five kinds of the antibody clones (BT-015, BT-175, NT-221, NT-320, NT-523) that showed good expression of the IgG type antibodies and easily prepared, when the IgG type antibody was administered alone. Therefore an antitoxin preparation evaluation test was carried out in order to find a combination of the antibodies that can completely neutralize botulinum toxin type-A. In other words, various combinations (specimens) were prepared based on BT-015 and BT-017 that has a more synergistic effect in being administered in combination than being administered alone, and has apparently different epitopes from each other (Table 3), to compare neutralization activities thereof.

The antibodies prepared to 1 mg/ml each were mixed in an equal amount to prepare an antibody solution that is served as a specimen stock solution. The specimen stock solution was subjected to a 3-fold serial dilution to 81-fold dilution, thereby to make a specimen diluted solution. After addition of 0.38 ml of PBS to 0.25 ml of the specimen dilution to make a volume of 0.63 ml, the mixture was well mixed with a test toxin of 0.63 ml, allowed to react at room temperature for one hour, and inoculated intraperitoneally to the mice (one group: 2 mice), followed by 40-day observation.

Botulinum antitoxin type-A Japanese standard (10 units/ml) was used as a comparative control, and it was diluted with PBS to prepare a five serial dilution containing a suitable interval concentration unit (hereinafter referred to as "Standard Dilution"; Table 4) in consideration of test accuracy mainly on 0.50 unit/ml. Botulinum neurotoxin corresponding to each antitoxin was diluted to prepare a test toxin (214ipLD50/ml). The test toxin (0.63 ml) and 0.63 ml each of the standard dilution and the specimen dilution were taken accurately, mixed well, allowed to react at room temperature for one hour, inoculated to the mice (one group: two mice) intraperitoneally at a dose of 0.5 ml each, and observed for 40 days. The titer of the specimens was determined as a relative value to Japanese Standard.

TABLE 4

Standard dilution

| Japanese Standard Antitoxin 0.5 unit/ml | PBS |
| --- | --- |
| 0.30 ml | 0.33 ml |
| 0.28 ml | 0.35 ml |
| 0.25 ml | 0.38 ml |
| 0.23 ml | 0.40 ml |
| 0.21 ml | 0.42 ml |

The results of the neutralization test (Table 4) revealed that the following three kinds of antibodies, namely BT-015, BT-175 and NT-320 were successfully neutralized completely by mixing them together (sample 6), and the strongest activity was recognized when the following four kinds of antibodies, namely BT-015, BT-175, NT-320 and NT-523 were mixed together (sample 4). The activity when four kinds of antibodies were used together was 12 units/mg (=12 units/ml). On the other hand, a high neutralizing activity was also shown even when BT-015, BT-175 and NT-523 were mixed together (sample 7). In addition, it was suggested that the neutralizing activity was improved when NT-221 was mixed with these three kinds of antibodies (sample 3).

TABLE 3

| Sample 1 Mix of Five Kinds | Sample 2 Mix of Four Kinds | Sample 3 Mix of Four Kinds | Sample 4 Mix of Four Kinds | Sample 5 Mix of three Kinds | Sample 6 Mix of three Kinds | Sample 7 Mix of three Kinds |
| --- | --- | --- | --- | --- | --- | --- |
| BT-015 | BT-015 | BT-015 | BT-015 | BT-015 | BT-015 | BT-015 |
| BT-175 | BT-175 | BT-175 | BT-175 | BT-175 | BT-175 | BT-175 |
| NT-221 | NT-221 | NT-221 | NT-320 | NT-221 | NT-320 | NT-523 |
| NT-320 | NT-320 | NT-523 | NT-523 | | | |
| NT-523 | | | | | | |

Note that because an antitoxin antibody type-A is contained in 10000 units/vial in a current therapeutic freeze-dried equine botulinum antitoxin type-A (a mixture of four kinds of A, B, E, and F), an equal activity will be obtained by mixing each antibody (about 210 mg each) together in the alternative case with use of four kinds of antibodies.

4-5. Antibody Epitope Analysis by ELISA and Reactivity to Toxin Subtype-A2

In order to analyze epitopes of six kinds of neutralizing antibodies (BT-015, BT-175, NT-221, NT-320, NT-523, NT-539) in more detail, as well as to confirm the reactivity of a subtype A2 thereof, neurotoxin (CHIBA-H) at the same time, ELISA was carried out using each antigen shown below.

Toxin type-A 62A neurotoxin (NT) (BoNT/A1)
Neurotoxin heavy chain (H-chain)
Neurotoxin light chain (L-chain)
Toxin subtype-A2 neurotoxin CHIBA-H (BoNT/A2)

Operation procedures are as follows. Each antigen was diluted with PBS (NT: 10 μg/ml, H-chain: 7 μg/m, L-chain: 3.5 μg/ml), and subdivided in 100 μl/well onto a microplate. After reaction at 37° C. for two hours, the solution was discarded. Subsequently, blocking was carried out overnight by the reaction with BSA that had been diluted to 0.5% with PBS. After discarding the solution, six kinds of IgG type neutralizing antibodies that had been subjected to a serial dilution to a concentration shown below were subdivided in 100 μl/well each, and allowed to react for two hours. Further, as shown below, optimum dilution concentration for each antibody was set by a preliminary experiment.

BT-015, BT-175, NT-221: 1 μg/ml, 0.5 μg/ml, 0.25 μg/ml, 0.125 μg/ml

NT-320, NT-523, NT-539: 10 μg/ml, 5 μg/ml, 2.5 μg/ml, 1.25 μg/ml

Then, after washing with PBS, an HRP labeled goat anti-human IgG antibody (BIO-RAD®) that had been diluted 20000-fold with PBS was allowed to react at 37° C. for two hours. The solution was discarded, washed with PBS, and 150 μl of an OPD solution (o-phenylenediamine 0.4 mg/ml) was allowed to react at 37° C. for 30 minutes. The reaction was stopped by adding 50 μl of 5N sulfuric acid, and absorbance at 492 nm was measured. The measurement results are shown in the table of FIG. 29. Further, the value obtained by subtracting the OD value of the human IgG antibody (each concentration) as the negative control (non-relevant antibody) from the average value of two wells was shown. Note that the case where the OD value was 3.5 or more was not measurable, and it was listed as ">3.500" in the table. ND represents "not determined".

The results shown in FIG. 29 were interpreted as follows.

The epitope of NT-320 exists on the H-chain because NT-320 recognizes the H-chain.

NT-523 reacted with both of the H-chain and L-chain.

Four other kinds did not react with any one of the H-chain and L-chain.

BT-015, BT-175, and NT-539 have each the same level of reactivity to BoNT/A1 and BoNT/A2.

NT-221, NT-320, and NT-523 have each a decreased reactivity to BoNT/A2 compared to BoNT/A1.

Considering the above-mentioned interpretations together, it was suggested that NT-539 was superior to NT-523 in the possibility for neutralization of toxin type-A2.

4-6. Epitope Analysis by Immunoblotting

Figure 30:
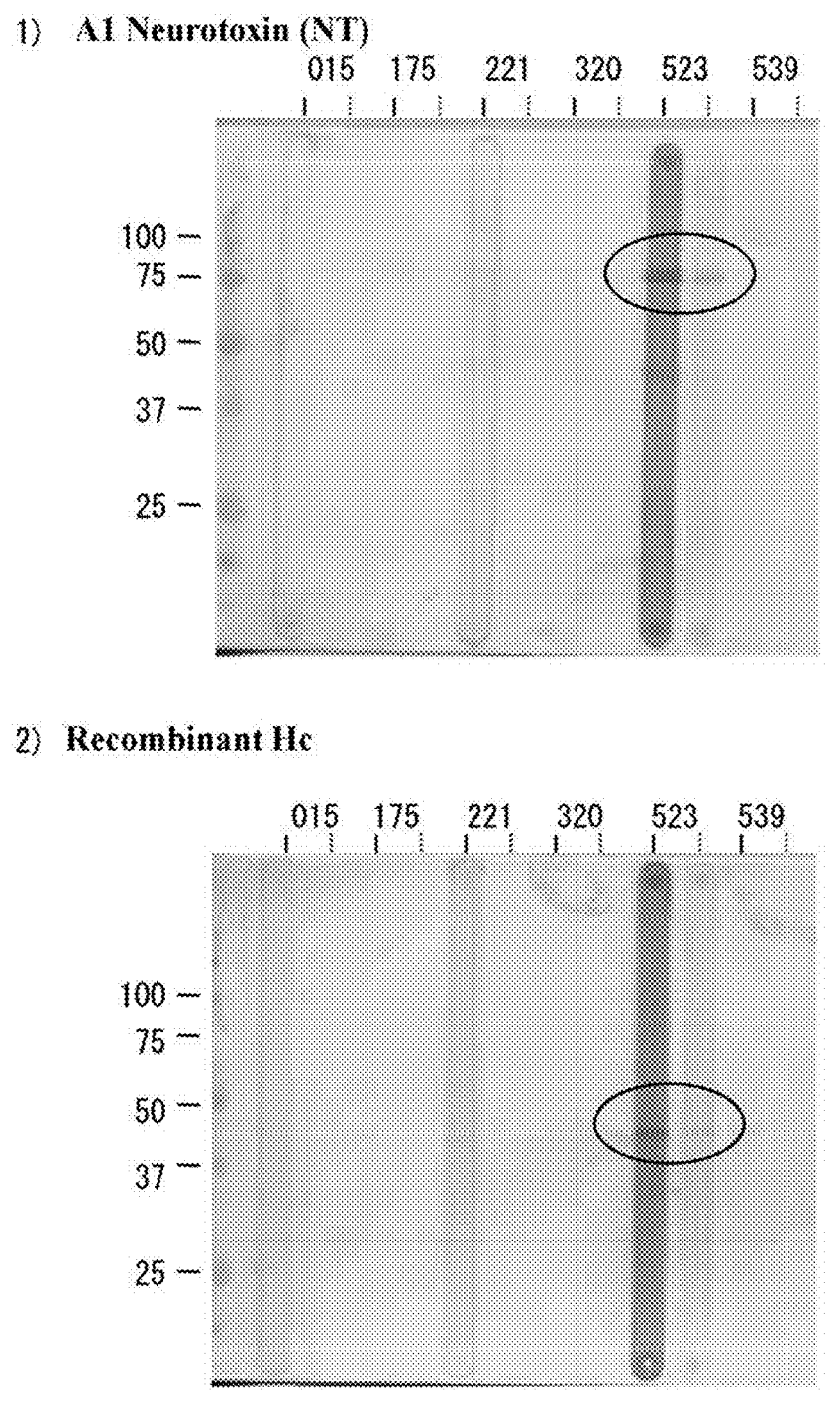

Subsequently, an epitope analysis was performed by immunoblotting for the neurotoxin (NT) and the neuron-binding domain of the heavy chain C-terminal end (Hc, *E. coli* recombinant protein). SDS-PAGE (neurotoxin: 1.5 μg/lane, Hc: 0.5 μg/lane) was performed using acrylamide gel of 10% concentration, transcribed/blocked to a membrane, diluted to two kinds of concentration including 50 μg/ml (solid line lane) and 5 μg/ml (dashed line lane), and allowed to react with 200 μg each of six kinds of IgG type neutralizing antibodies. The product was washed with PBS and reacted with an HRP labeled goat anti-human IgG antibody that had been diluted 20000-fold with PBS. The product was washed with PBS and detected using DAB as a chromogenic substrate (FIG. 30).

The results of the reactivity to the neuron-binding domain at the heavy chain C-terminal end (Hc) were interpreted as follows.

NT-523 recognized the primary structure of the Hc domain.

Other antibodies are considered to be an antibody recognizing the higher order structure of the toxin because no band was detected.

4-7. Epitope Analysis by Immunoprecipitation

Figure 31:
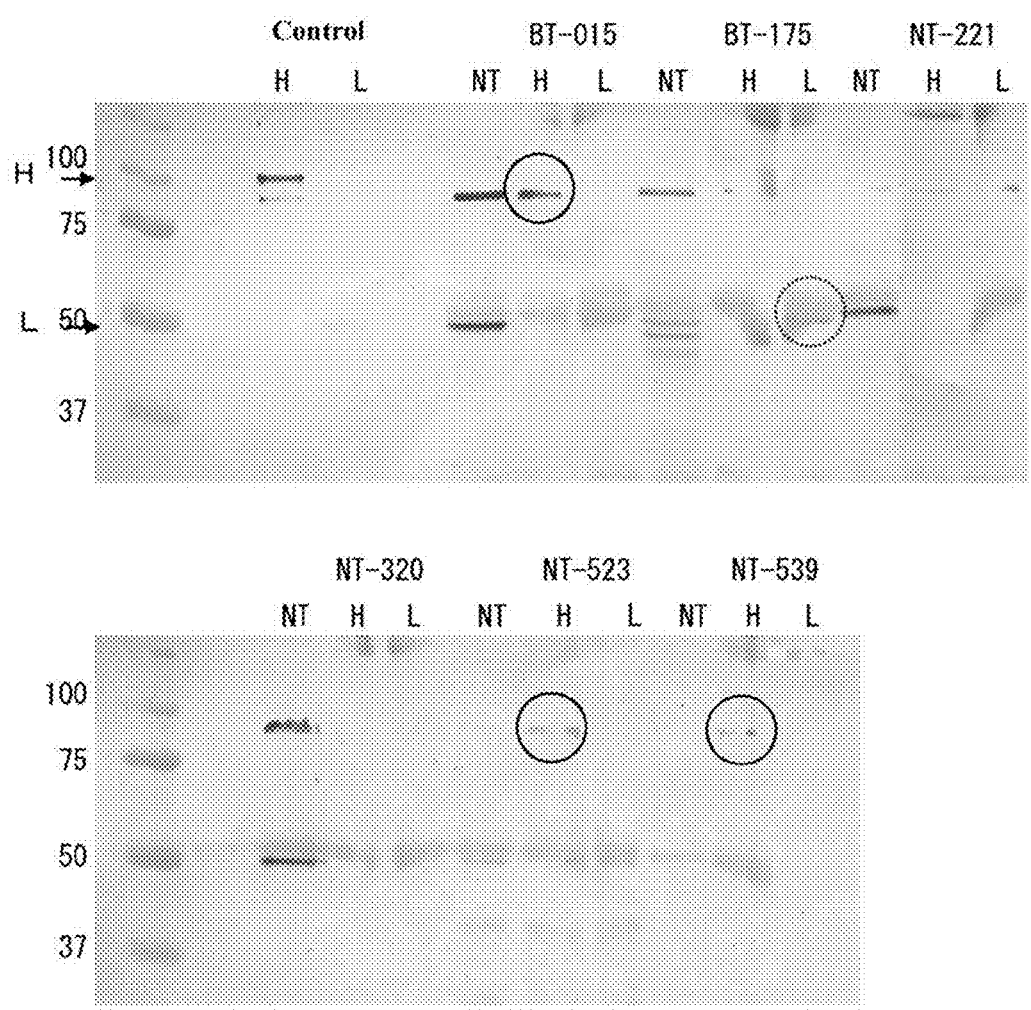
FIG. 31 shows an epitope analysis by immunoprecipitation. It represents the result of the epitope analysis carried out by the immunoprecipitation for each clone using three kinds of antigens (neurotoxin, H-chain, L-chain). The control is subjected to an electrophoresis of the upper layer of the H-chain and L-chain as they are and allowed to react with a rabbit botulinum neurotoxin type-A antibody (diluted 1,000-fold) purified by affinity purification. The possibility of recognizing H-chain is high in the case of BT-015, NT-523, and NT-539 (solid line circle), and the possibility of recognizing L-chain is high in the case of BT-175 (dashed line circle). However, from this experiment, it was not able to determine which of the H-chain and L-chain is recognized by NT-221 and NT-320.

An epitope analysis was carried out by immunoprecipitation using further three kinds of antigens (neurotoxin, heavy chain, light chain). IgG type neutralizing antibodies (5 μg each) were reacted with protein G Sepharose (100 μl) to prepare six kinds of antibody beads. An antigen (neurotoxin: 0.6 μg/100 μl, H-chain: 0.4 μg/100 μL-chain: 0.4 μg/100 μl) was reacted with the antibody beads at 4° C. overnight. After washing, SDS-PAGE was performed using acrylamide gel of 10% concentration, transcribed/blocked to a membrane, and allowed to react with a rabbit anti-botulinum neurotoxin antibody type-A (diluted 1000-fold) that had been purified through affinity purification. After washing the product with PBS, this was reacted with an HRP labeled goat anti-rabbit IgG type-antibody (BIO-RAD®) at 37° C. After washing with PBS, the product was detected using a chromogenic substrate (FIG. 31).

The results of FIG. 31 were interpreted as follows.

BT-015, NT-523, and NT-539 recognize the H-chain (solid line circle).

BT-175 has a high possibility of recognizing the L-chain (dashed line circle).

It is impossible to decide which of the H-chain or the L-chain is recognized by NT-221 and NT-320.

Considering the results of the epitope analysis described in 4-5 to 4-7 together, the epitope classification of six kinds of antibodies are as shown in FIG. 32. Further, as for binding ability of each clone (epitope candidate), NT shows the case where there is a binding activity to the neurotoxin; H shows the case where there is a binding activity to the H-chain; Hc shows the case where there is a binding activity to the neuron-binding domain of the H-chain C-terminal end; and L shows the case where there is a binding activity to the L-chain. The symbol (-) indicates "not evaluable".

INDUSTRIAL APPLICABILITY

The composition for neutralizing botulinum toxin type-A of the present invention contains a plurality of antibodies whose epitopes are different from each other and exhibits a high neutralizing activity. The active ingredient of the present invention is an antibody having a fully human variable region. This feature can solve the problems faced in the conventional preparation (equine antitoxin preparation or neutralizing chimeric antibody), such as much time for the production, difficulty in stable supply, and further contamination of unknown virus, can be solved by this feature. The present invention enables the practical use of a stable and economical anti-botulinum toxin type-A preparation and greatly contributes to treatment and prevention of a botulism patient.

On the other hand, the present invention provides a composition for neutralizing botulinum toxin type-A, which is conformed to the international standard of toxin neutralization test. Therefore, the present invention is extremely useful as internationally usable means for treating and preventing the poisoning in the developing countries where the storage system is not yet in order, particularly sudden and great outbreaking poisoning, and bioterrorism, etc.

The present invention is not limited by the descriptions of Embodiments and Examples of the above-described invention at all. The present invention also includes a variety of modified aspects within the scope where those skilled in the art can easily conceive without departing from the scope of the claims.

The contents of the theses, publications of patent applications, and patent publications specified in this description are herein incorporated by reference in their entireties.

The invention claimed is:

1. A composition for neutralizing botulinum toxin type-A comprising:
a first human anti-botulinum toxin type-A antibody that recognizes an epitope which is recognized by an antibody having a heavy chain variable region (VH) comprising the amino acid sequence of SEQ ID NO: 4 and a light chain variable region (VL) comprising the amino acid sequence of SEQ ID NO: 8;
a second human anti-botulinum toxin type-A antibody that recognizes an epitope which is recognized by an antibody having a VH comprising the amino acid sequence of SEQ ID NO: 36 and a VL comprising the amino acid sequence of SEQ ID NO: 40; and
a third human anti-botulinum toxin type-A antibody that recognizes an epitope which is recognized by an antibody having a VH comprising the amino acid sequence of SEQ ID NO: 44 and a VL comprising the amino acid sequence of SEQ ID NO: 48, or that recognizes an epitope which is recognized by an antibody having a VH comprising the amino acid sequence of SEQ ID NO: 52 and a VL comprising the amino acid sequence of SEQ ID NO: 56.

2. The composition for neutralizing botulinum toxin type-A according to claim 1, wherein:
the first human anti-botulinum toxin type-A antibody is any one of antibodies selected from the group consisting of the following (1) to (3);
the second human anti-botulinum toxin type-A antibody is an antibody of the following (4) or (5); and
the third human anti-botulinum toxin type-A antibody is any one of antibodies selected from the group consisting of the following (6) to (8):
(1) an antibody having a heavy chain complementarity-determining region (CDR) 1 comprising the amino acid sequence of SEQ ID NO: 1, a heavy chain CDR2 comprising the amino acid sequence of SEQ ID NO: 2, a heavy chain CDR3 comprising the amino acid sequence of SEQ ID NO: 3, a light chain CDR1 comprising the amino acid sequence of SEQ ID NO: 5, a light chain CDR2 comprising the amino acid sequence of SEQ ID NO: 6, and a light chain CDR3 comprising the amino acid sequence of SEQ ID NO: 7;

(2) an antibody having a heavy chain CDR1 comprising the amino acid sequence of SEQ ID NO: 9, a heavy chain CDR2 comprising the amino acid sequence of SEQ ID NO: 10, a heavy chain CDR3 comprising the amino acid sequence of SEQ ID NO: 11, a light chain CDR1 comprising the amino acid sequence of SEQ ID NO: 13, a light chain CDR2 comprising the amino acid sequence of SEQ ID NO: 14, and a light chain CDR3 comprising the amino acid sequence of SEQ ID NO: 15;

(3) an antibody having a heavy chain CDR1 comprising the amino acid sequence of SEQ ID NO: 17, a heavy chain CDR2 comprising the amino acid sequence of SEQ ID NO: 18, a heavy chain CDR3 comprising the amino acid sequence of SEQ ID NO: 19, a light chain CDR1 comprising the amino acid sequence of SEQ ID NO: 21, a light chain CDR2 comprising the amino acid sequence of SEQ ID NO: 22, and a light chain CDR3 comprising the amino acid sequence of SEQ ID NO: 23;

(4) an antibody having a heavy chain CDR1 comprising the amino acid sequence of SEQ ID NO: 25, a heavy chain CDR2 comprising the amino acid sequence of SEQ ID NO: 26, a heavy chain CDR3 comprising the amino acid sequence of SEQ ID NO: 27, a light chain CDR1 comprising the amino acid sequence of SEQ ID NO: 29, a light chain CDR2 comprising the amino acid sequence of SEQ ID NO: 30, and a light chain CDR3 comprising the amino acid sequence of SEQ ID NO: 31;

(5) an antibody having a heavy chain CDR1 comprising the amino acid sequence of SEQ ID NO: 33, a heavy chain CDR2 comprising the amino acid sequence of SEQ ID NO: 34, a heavy chain CDR3 comprising the amino acid sequence of SEQ ID NO: 35, a light chain CDR1 comprising the amino acid sequence of SEQ ID NO: 37, a light chain CDR2 comprising the amino acid sequence of SEQ ID NO: 38, and a light chain CDR3 comprising the amino acid sequence of SEQ ID NO: 39;

(6) an antibody having a heavy chain CDR1 comprising the amino acid sequence of SEQ ID NO: 41, a heavy chain CDR2 comprising the amino acid sequence of SEQ ID NO: 42, a heavy chain CDR3 comprising the amino acid sequence of SEQ ID NO: 43, a light chain CDR1 comprising the amino acid sequence of SEQ ID NO: 45, a light chain CDR2 comprising the amino acid sequence of SEQ ID NO: 46, and a light chain CDR3 comprising the amino acid sequence of SEQ ID NO: 47;

(7) an antibody having a heavy chain CDR1 comprising the amino acid sequence of SEQ ID NO: 49, a heavy chain CDR2 comprising the amino acid sequence of SEQ ID NO: 50, a heavy chain CDR3 comprising the amino acid sequence of SEQ ID NO: 51, a light chain CDR1 comprising the amino acid sequence of SEQ ID NO: 53, a light chain CDR2 comprising the amino acid sequence of SEQ ID NO: 54, and a light chain CDR3 comprising the amino acid sequence of SEQ ID NO: 55; and (8) an antibody having a heavy chain CDR1 comprising the amino acid sequence of SEQ ID NO: 57, a heavy chain CDR2 comprising the amino acid sequence of SEQ ID NO: 58, a heavy chain CDR3 comprising the amino acid sequence of SEQ ID NO: 59; a light chain CDR1 comprising the amino acid sequence of SEQ ID NO: 61, a light chain CDR2 comprising the amino acid sequence of SEQ ID NO: 62, and a light chain CDR3 comprising the amino acid sequence of SEQ ID NO: 63.

3. The composition for neutralizing botulinum toxin type-A according to claim 2, wherein:
the first human anti-botulinum toxin type-A antibody is any one of antibodies selected from the group consisting of the above-mentioned (1) to (3);
the second human anti-botulinum toxin type-A antibody is the above-mentioned antibody (4) or (5);
the third human anti-botulinum toxin type-A antibody is the above-mentioned antibody (6); and
the above-mentioned antibody (7) or (8) is further comprised as a fourth human anti-botulinum toxin type-A antibody.

4. The composition for neutralizing botulinum toxin type-A according to claim 2, wherein:
the first human anti-botulinum toxin type-A antibody is the above-mentioned antibody (1);
the second human anti-botulinum toxin type-A antibody is the above-mentioned antibody (5); and
the third human anti-botulinum toxin type-A antibody is the above-mentioned antibody (6).

5. The composition for neutralizing botulinum toxin type-A according to claim 4, wherein the above-mentioned antibody (7) is further comprised as a fourth human anti-botulinum toxin type-A antibody.

6. The composition for neutralizing botulinum toxin type-A according to claim 2, wherein:
the first human anti-botulinum toxin type-A antibody is the above-mentioned antibody (1);
the second human anti-botulinum toxin type-A antibody is the above-mentioned antibody (5); and
the third human anti-botulinum toxin type-A antibody is the above-mentioned antibody (7).

7. The composition for neutralizing botulinum toxin type-A according to claim 6, wherein the above-mentioned antibody (4) is further comprised as a fourth human anti-botulinum toxin type-A antibody.

8. The composition for neutralizing botulinum toxin type-A according to claim 2, wherein:
the above-mentioned antibody (1) has a VH comprising the amino acid sequence of SEQ ID NO: 4 and a VL comprising the amino acid sequence of SEQ ID NO: 8;
the above-mentioned antibody (2) has a VH comprising the amino acid sequence of SEQ ID NO: 12 and a VL comprising the amino acid sequence of SEQ ID NO: 16;
the above-mentioned antibody (3) has a VH comprising the amino acid sequence of SEQ ID NO: 20 and a VL comprising the amino acid sequence of SEQ ID NO: 24;
the above-mentioned antibody (4) has a VH comprising the amino acid sequence of SEQ ID NO: 28 and a VL comprising the amino acid sequence of SEQ ID NO: 32;
the above-mentioned antibody (5) has a VH comprising the amino acid sequence of SEQ ID NO: 36 and a VL comprising the amino acid sequence of SEQ ID NO: 40;
the above-mentioned antibody (6) has a VH comprising the amino acid sequence of SEQ ID NO: 44 and a VL comprising the amino acid sequence of SEQ ID NO: 48;
the above-mentioned antibody (7) has a VH comprising the amino acid sequence of SEQ ID NO: 52 and a VL comprising the amino acid sequence of SEQ ID NO: 56; and
the above-mentioned antibody (8) has a VH comprising the amino acid sequence of SEQ ID NO: 60 and a VL comprising the amino acid sequence of SEQ ID NO: 64.

9. The composition for neutralizing botulinum toxin type-A according to claim 3, wherein:
the above-mentioned antibody (1) has a VH comprising the amino acid sequence of SEQ ID NO: 4 and a VL comprising the amino acid sequence of SEQ ID NO: 8;
the above-mentioned antibody (2) has a VH comprising the amino acid sequence of SEQ ID NO: 12 and a VL comprising the amino acid sequence of SEQ ID NO: 16;
the above-mentioned antibody (3) has a VH comprising the amino acid sequence of SEQ ID NO: 20 and a VL comprising the amino acid sequence of SEQ ID NO: 24;
the above-mentioned antibody (4) has a VH comprising the amino acid sequence of SEQ ID NO: 28 and a VL comprising the amino acid sequence of SEQ ID NO: 32;
the above-mentioned antibody (5) has a VH comprising the amino acid sequence of SEQ ID NO: 36 and a VL comprising the amino acid sequence of SEQ ID NO: 40;
the above-mentioned antibody (6) has a VH comprising the amino acid sequence of SEQ ID NO: 44 and a VL comprising the amino acid sequence of SEQ ID NO: 48;
the above-mentioned antibody (7) has a VH comprising the amino acid sequence of SEQ ID NO: 52 and a VL comprising the amino acid sequence of SEQ ID NO: 56; and
the above-mentioned antibody (8) has a VH comprising the amino acid sequence of SEQ ID NO: 60 and a VL comprising the amino acid sequence of SEQ ID NO: 64.

10. The composition for neutralizing botulinum toxin type-A according to claim 4, wherein:
the above-mentioned antibody (1) has a VH comprising the amino acid sequence of SEQ ID NO: 4 and a VL comprising the amino acid sequence of SEQ ID NO: 8;
the above-mentioned antibody (2) has a VH comprising the amino acid sequence of SEQ ID NO: 12 and a VL comprising the amino acid sequence of SEQ ID NO: 16;
the above-mentioned antibody (3) has a VH comprising the amino acid sequence of SEQ ID NO: 20 and a VL comprising the amino acid sequence of SEQ ID NO: 24;
the above-mentioned antibody (4) has a VH comprising the amino acid sequence of SEQ ID NO: 28 and a VL comprising the amino acid sequence of SEQ ID NO: 32;
the above-mentioned antibody (5) has a VH comprising the amino acid sequence of SEQ ID NO: 36 and a VL comprising the amino acid sequence of SEQ ID NO: 40;
the above-mentioned antibody (6) has a VH comprising the amino acid sequence of SEQ ID NO: 44 and a VL comprising the amino acid sequence of SEQ ID NO: 48;
the above-mentioned antibody (7) has a VH comprising the amino acid sequence of SEQ ID NO: 52 and a VL comprising the amino acid sequence of SEQ ID NO: 56; and
the above-mentioned antibody (8) has a VH comprising the amino acid sequence of SEQ ID NO: 60 and a VL comprising the amino acid sequence of SEQ ID NO: 64.

11. The composition for neutralizing botulinum toxin type-A according to claim 5, wherein:
the above-mentioned antibody (1) has a VH comprising the amino acid sequence of SEQ ID NO: 4 and a VL comprising the amino acid sequence of SEQ ID NO: 8;
the above-mentioned antibody (2) has a VH comprising the amino acid sequence of SEQ ID NO: 12 and a VL comprising the amino acid sequence of SEQ ID NO: 16;
the above-mentioned antibody (3) has a VH comprising the amino acid sequence of SEQ ID NO: 20 and a VL comprising the amino acid sequence of SEQ ID NO: 24;
the above-mentioned antibody (4) has a VH comprising the amino acid sequence of SEQ ID NO: 28 and a VL comprising the amino acid sequence of SEQ ID NO: 32;
the above-mentioned antibody (5) has a VH comprising the amino acid sequence of SEQ ID NO: 36 and a VL comprising the amino acid sequence of SEQ ID NO: 40;
the above-mentioned antibody (6) has a VH comprising the amino acid sequence of SEQ ID NO: 44 and a VL comprising the amino acid sequence of SEQ ID NO: 48;
the above-mentioned antibody (7) has a VH comprising the amino acid sequence of SEQ ID NO: 52 and a VL comprising the amino acid sequence of SEQ ID NO: 56; and
the above-mentioned antibody (8) has a VH comprising the amino acid sequence of SEQ ID NO: 60 and a VL comprising the amino acid sequence of SEQ ID NO: 64.

12. The composition for neutralizing botulinum toxin type-A according to claim 6, wherein:
the above-mentioned antibody (1) has a VH comprising the amino acid sequence of SEQ ID NO: 4 and a VL comprising the amino acid sequence of SEQ ID NO: 8;
the above-mentioned antibody (2) has a VH comprising the amino acid sequence of SEQ ID NO: 12 and a VL comprising the amino acid sequence of SEQ ID NO: 16;
the above-mentioned antibody (3) has a VH comprising the amino acid sequence of SEQ ID NO: 20 and a VL comprising the amino acid sequence of SEQ ID NO: 24;
the above-mentioned antibody (4) has a VH comprising the amino acid sequence of SEQ ID NO: 28 and a VL comprising the amino acid sequence of SEQ ID NO: 32;
the above-mentioned antibody (5) has a VH comprising the amino acid sequence of SEQ ID NO: 36 and a VL comprising the amino acid sequence of SEQ ID NO: 40;
the above-mentioned antibody (6) has a VH comprising the amino acid sequence of SEQ ID NO: 44 and a VL comprising the amino acid sequence of SEQ ID NO: 48;
the above-mentioned antibody (7) has a VH comprising the amino acid sequence of SEQ ID NO: 52 and a VL comprising the amino acid sequence of SEQ ID NO: 56; and
the above-mentioned antibody (8) has a VH comprising the amino acid sequence of SEQ ID NO: 60 and a VL comprising the amino acid sequence of SEQ ID NO: 64.

13. The composition for neutralizing botulinum toxin type-A according to claim 7, wherein:
the above-mentioned antibody (1) has a VH comprising the amino acid sequence of SEQ ID NO: 4 and a VL comprising the amino acid sequence of SEQ ID NO: 8;
the above-mentioned antibody (2) has a VH comprising the amino acid sequence of SEQ ID NO: 12 and a VL comprising the amino acid sequence of SEQ ID NO: 16;
the above-mentioned antibody (3) has a VH comprising the amino acid sequence of SEQ ID NO: 20 and a VL comprising the amino acid sequence of SEQ ID NO: 24;
the above-mentioned antibody (4) has a VH comprising the amino acid sequence of SEQ ID NO: 28 and a VL comprising the amino acid sequence of SEQ ID NO: 32;
the above-mentioned antibody (5) has a VH comprising the amino acid sequence of SEQ ID NO: 36 and a VL comprising the amino acid sequence of SEQ ID NO: 40;
the above-mentioned antibody (6) has a VH comprising the amino acid sequence of SEQ ID NO: 44 and a VL comprising the amino acid sequence of SEQ ID NO: 48;
the above-mentioned antibody (7) has a VH comprising the amino acid sequence of SEQ ID NO: 52 and a VL comprising the amino acid sequence of SEQ ID NO: 56; and
the above-mentioned antibody (8) has a VH comprising the amino acid sequence of SEQ ID NO: 60 and a VL comprising the amino acid sequence of SEQ ID NO: 64.

* * * * *

SEQUENCE LISTING

```
<160> NUMBER OF SEQ ID NOS: 109

<210> SEQ ID NO 1
<211> LENGTH: 5
<212> TYPE: PRT
<213> ORGANISM: Homo sapiens

<400> SEQUENCE: 1

Ala Tyr Tyr Met His
1               5

<210> SEQ ID NO 2
<211> LENGTH: 17
<212> TYPE: PRT
<213> ORGANISM: Homo sapiens

<400> SEQUENCE: 2

Trp Ile Asn Pro His Ser Gly Val Thr Thr Tyr Ala Gln Lys Phe Gln
1               5                   10                  15

Gly

<210> SEQ ID NO 3
<211> LENGTH: 18
<212> TYPE: PRT
<213> ORGANISM: Homo sapiens

<400> SEQUENCE: 3

Gly Phe Gly Ser Ser Cys Ser Asp Thr Ser Cys Ser Phe Ser Gly Leu
1               5                   10                  15

Asp Val

<210> SEQ ID NO 4
<211> LENGTH: 127
<212> TYPE: PRT
<213> ORGANISM: Homo sapiens

<400> SEQUENCE: 4

Gln Val Gln Leu Gln Gln Ser Gly Ala Glu Val Lys Lys Pro Gly Ala
1               5                   10                  15

Ser Val Lys Val Ala Cys Lys Ala Ser Arg Tyr Asn Phe Ser Ala Tyr
                20                  25                  30

Tyr Met His Trp Val Arg Gln Ala Pro Gly Gln Gly Pro Glu Trp Met
        35                  40                  45

Gly Trp Ile Asn Pro His Ser Gly Val Thr Thr Tyr Ala Gln Lys Phe
    50                  55                  60

Gln Gly Arg Val Thr Met Thr Arg Asp Thr Ser Ile Gly Thr Ala Tyr
65                  70                  75                  80

Met Glu Leu Ser Arg Leu Arg Ser Asp Thr Ala Leu Tyr Tyr Cys
                85                  90                  95

Ala Arg Gly Phe Gly Ser Ser Cys Ser Asp Thr Ser Cys Ser Phe Ser
                100                 105                 110

Gly Leu Asp Val Trp Gly Gln Gly Thr Thr Val Thr Val Ser Ser
        115                 120                 125

<210> SEQ ID NO 5
```

```
<211> LENGTH: 14
<212> TYPE: PRT
<213> ORGANISM: Homo sapiens

<400> SEQUENCE: 5

Thr Gly Thr Ser Ser Asp Val Gly Gly Tyr Asp Tyr Val Ser
1               5                   10

<210> SEQ ID NO 6
<211> LENGTH: 8
<212> TYPE: PRT
<213> ORGANISM: Homo sapiens

<400> SEQUENCE: 6

Asp Val Thr Asn Arg Pro Ser Gly
1               5

<210> SEQ ID NO 7
<211> LENGTH: 10
<212> TYPE: PRT
<213> ORGANISM: Homo sapiens

<400> SEQUENCE: 7

Thr Ser Tyr Thr Ser Ser Val Thr Tyr Val
1               5                   10

<210> SEQ ID NO 8
<211> LENGTH: 111
<212> TYPE: PRT
<213> ORGANISM: Homo sapiens

<400> SEQUENCE: 8

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asp Tyr Val Ser Trp Tyr Gln Gln His Pro Gly Glu Ala Pro Lys Leu
        35                  40                  45

Leu Ile Tyr Asp Val Thr Asn Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Pro Glu Asp Glu Ala Asp Tyr Tyr Cys Thr Ser Tyr Thr Ser Ser
                85                  90                  95

Val Thr Tyr Val Phe Gly Ser Gly Thr Thr Leu Thr Val Leu Ser
            100                 105                 110

<210> SEQ ID NO 9
<211> LENGTH: 5
<212> TYPE: PRT
<213> ORGANISM: Homo sapiens

<400> SEQUENCE: 9

Ala Tyr Tyr Met His
1               5

<210> SEQ ID NO 10
<211> LENGTH: 17
<212> TYPE: PRT
<213> ORGANISM: Homo sapiens

<400> SEQUENCE: 10

Trp Ile Asn Pro His Ser Gly Val Thr Thr Tyr Ala Arg Lys Phe Gln
```

-continued

```
                  1               5                  10                 15
Gly

<210> SEQ ID NO 11
<211> LENGTH: 18
<212> TYPE: PRT
<213> ORGANISM: Homo sapiens

<400> SEQUENCE: 11

Gly Phe Gly Ser Ser Cys Ser Asp Thr Ser Cys Ser Phe Ser Gly Leu
1               5                   10                  15

Asp Val

<210> SEQ ID NO 12
<211> LENGTH: 127
<212> TYPE: PRT
<213> ORGANISM: Homo sapiens

<400> SEQUENCE: 12

Gln Val Gln Leu Val Gln Ser Gly Ala Glu Val Lys Lys Pro Gly Ala
1               5                   10                  15

Ser Val Lys Val Ala Cys Lys Ala Ser Arg Tyr Asn Phe Ser Ala Tyr
            20                  25                  30

Tyr Met His Trp Val Arg Gln Ala Pro Gly Gln Gly Pro Glu Trp Met
        35                  40                  45

Gly Trp Ile Asn Pro His Ser Gly Val Thr Thr Tyr Ala Arg Lys Phe
    50                  55                  60

Gln Gly Arg Val Thr Met Thr Arg Asp Thr Ser Ile Gly Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Phe Gly Ser Ser Cys Ser Asp Thr Ser Cys Ser Phe Ser
            100                 105                 110

Gly Leu Asp Val Trp Gly Gln Gly Thr Thr Val Thr Val Ser Ser
        115                 120                 125

<210> SEQ ID NO 13
<211> LENGTH: 12
<212> TYPE: PRT
<213> ORGANISM: Homo sapiens

<400> SEQUENCE: 13

Arg Ala Ser Gln Ser Val Ser Ser Ser Tyr Leu Ala
1               5                   10

<210> SEQ ID NO 14
<211> LENGTH: 8
<212> TYPE: PRT
<213> ORGANISM: Homo sapiens

<400> SEQUENCE: 14

Gly Ala Ser Ser Arg Ala Thr Gly
1               5

<210> SEQ ID NO 15
<211> LENGTH: 10
<212> TYPE: PRT
<213> ORGANISM: Homo sapiens

<400> SEQUENCE: 15

Gln Gln Tyr Gly Ser Ser Pro Leu Tyr Thr
```

<210> SEQ ID NO 16
<211> LENGTH: 109
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Tyr Thr Phe Gly Gln Gly Thr Lys Leu Glu Ile Lys
            100                 105

<210> SEQ ID NO 17
<211> LENGTH: 5
<212> TYPE: PRT
<213> ORGANISM: Homo sapiens

<400> SEQUENCE: 17

Ala Tyr Tyr Met His
1               5

<210> SEQ ID NO 18
<211> LENGTH: 17
<212> TYPE: PRT
<213> ORGANISM: Homo sapiens

<400> SEQUENCE: 18

Trp Ile Asn Pro His Ser Gly Gly Thr Asn Tyr Ala Gln Lys Phe Gln
1               5                   10                  15

Gly

<210> SEQ ID NO 19
<211> LENGTH: 18
<212> TYPE: PRT
<213> ORGANISM: Homo sapiens

<400> SEQUENCE: 19

Gly Phe Gly Ser Ser Cys Thr Ser Thr Ser Cys Gln Phe Ser Gly Leu
1               5                   10                  15

Asp Val

<210> SEQ ID NO 20
<211> LENGTH: 127
<212> TYPE: PRT
<213> ORGANISM: Homo sapiens

<400> SEQUENCE: 20

Gln Val Gln Leu Val Gln Ser Gly Ala Glu Val Arg Lys Pro Gly Ala
1               5                   10                  15

Ser Val Lys Val Ser Cys Lys Ala Ser Arg Tyr Ser Phe Thr Ala Tyr

```
            20                  25                  30
Tyr Met His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ser Thr Ala Tyr
65                  70                  75                  80

Met Glu Leu Ser Ser Leu Arg Ser Asp Asp Thr Ala Val Phe Tyr Cys
                85                  90                  95

Ala Arg Gly Phe Gly Ser Ser Cys Thr Ser Thr Ser Cys Gln Phe Ser
            100                 105                 110

Gly Leu Asp Val Trp Gly Gln Gly Thr Thr Val Thr Val Ser Ser
            115                 120                 125

<210> SEQ ID NO 21
<211> LENGTH: 14
<212> TYPE: PRT
<213> ORGANISM: Homo sapiens

<400> SEQUENCE: 21

Thr Gly Thr Ser Ser Asp Val Gly Gly Tyr Asn Tyr Val Ser
1               5                   10

<210> SEQ ID NO 22
<211> LENGTH: 8
<212> TYPE: PRT
<213> ORGANISM: Homo sapiens

<400> SEQUENCE: 22

Glu Val Thr Lys Arg Pro Ser Gly
1               5

<210> SEQ ID NO 23
<211> LENGTH: 11
<212> TYPE: PRT
<213> ORGANISM: Homo sapiens

<400> SEQUENCE: 23

Ser Ser Tyr Ala Gly Thr Asn Asn Leu Gly Val
1               5                   10

<210> SEQ ID NO 24
<211> LENGTH: 112
<212> TYPE: PRT
<213> ORGANISM: Homo sapiens

<400> SEQUENCE: 24

Gln Ser Ala Leu Thr Gln Pro Ala Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Ser Gly Leu
65                  70                  75                  80

Gln Ala Glu Asp Glu Ala Asp Tyr Tyr Cys Ser Ser Tyr Ala Gly Thr
                85                  90                  95

Asn Asn Leu Gly Val Phe Gly Thr Gly Thr Lys Val Thr Val Leu Gly
```

<210> SEQ ID NO 25
<211> LENGTH: 5
<212> TYPE: PRT
<213> ORGANISM: Homo sapiens

<400> SEQUENCE: 25

Gly Val Ala Val Gly
1               5

<210> SEQ ID NO 26
<211> LENGTH: 16
<212> TYPE: PRT
<213> ORGANISM: Homo sapiens

<400> SEQUENCE: 26

Leu Ile Tyr Trp Asp Asp Asp Lys Arg Tyr Ser Pro Ser Leu Lys Ser
1               5                   10                  15

<210> SEQ ID NO 27
<211> LENGTH: 14
<212> TYPE: PRT
<213> ORGANISM: Homo sapiens

<400> SEQUENCE: 27

Asn Thr Gly Thr Asp Leu Tyr Phe Asp Trp Ala Phe Asp Tyr
1               5                   10

<210> SEQ ID NO 28
<211> LENGTH: 124
<212> TYPE: PRT
<213> ORGANISM: Homo sapiens

<400> SEQUENCE: 28

Glu Val Gln Leu Val Glu Ser Gly Pro Thr Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Val Ala Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Asn Thr Gly Thr Asp Leu Tyr Phe Asp Trp Ala Phe Asp
            100                 105                 110

Tyr Trp Gly Gln Gly Thr Leu Val Thr Val Ser Ser
        115                 120

<210> SEQ ID NO 29
<211> LENGTH: 14
<212> TYPE: PRT
<213> ORGANISM: Homo sapiens

<400> SEQUENCE: 29

Thr Gly Ser Ser Ser Asn Ile Gly Ala Gly Tyr Asp Val His
1               5                   10

<210> SEQ ID NO 30

```
<211> LENGTH: 8
<212> TYPE: PRT
<213> ORGANISM: Homo sapiens

<400> SEQUENCE: 30

Gly Asn Ser Asn Arg Pro Ser Gly
1               5

<210> SEQ ID NO 31
<211> LENGTH: 11
<212> TYPE: PRT
<213> ORGANISM: Homo sapiens

<400> SEQUENCE: 31

Gln Ser Tyr Asp Ser Ser Leu Ser Gly Ser Val
1               5                   10

<210> SEQ ID NO 32
<211> LENGTH: 112
<212> TYPE: PRT
<213> ORGANISM: Homo sapiens

<400> SEQUENCE: 32

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Thr Lys Leu Thr Val Leu Gly
            100                 105                 110

<210> SEQ ID NO 33
<211> LENGTH: 5
<212> TYPE: PRT
<213> ORGANISM: Homo sapiens

<400> SEQUENCE: 33

Gly Val Gly Val Gly
1               5

<210> SEQ ID NO 34
<211> LENGTH: 16
<212> TYPE: PRT
<213> ORGANISM: Homo sapiens

<400> SEQUENCE: 34

Leu Ile Tyr Trp Asp Gly Asp Lys Arg Phe Ser Pro Ser Leu Lys Ser
1               5                   10                  15

<210> SEQ ID NO 35
<211> LENGTH: 14
<212> TYPE: PRT
<213> ORGANISM: Homo sapiens

<400> SEQUENCE: 35

Ser Phe Tyr His Gly Ser Gln Ser Pro Gly Trp Phe Asp Pro
```

<210> SEQ ID NO 36
<211> LENGTH: 124
<212> TYPE: PRT
<213> ORGANISM: Homo sapiens

<400> SEQUENCE: 36

```
Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Arg Thr Ser
            20                  25                  30
Gly Val Gly Val Gly Trp Ile Arg Gln Pro Pro Gly Lys Ala Pro Glu
        35                  40                  45
Trp Leu Ala Leu Ile Tyr Trp Asp Gly Asp Lys Arg Phe Ser Pro Ser
    50                  55                  60
Leu Lys Ser Arg Leu Thr Ile Asn Lys Asp Ile Ser Lys Asn Gln Val
65                  70                  75                  80
Val Leu Thr Leu Thr Asn Leu Asp Pro Val Asp Thr Gly Thr Tyr Tyr
                85                  90                  95
Cys Ala His Ser Phe Tyr His Gly Ser Gln Ser Pro Gly Trp Phe Asp
            100                 105                 110
Pro Trp Gly Gln Gly Thr Leu Val Thr Val Ser Ser
        115                 120
```

<210> SEQ ID NO 37
<211> LENGTH: 13
<212> TYPE: PRT
<213> ORGANISM: Homo sapiens

<400> SEQUENCE: 37

```
Ser Gly Ser Ser Ser Asn Ile Gly Asn Asn Tyr Val Ser
1               5                   10
```

<210> SEQ ID NO 38
<211> LENGTH: 8
<212> TYPE: PRT
<213> ORGANISM: Homo sapiens

<400> SEQUENCE: 38

```
Asp Asn Asn Lys Arg Pro Ser Gly
1               5
```

<210> SEQ ID NO 39
<211> LENGTH: 10
<212> TYPE: PRT
<213> ORGANISM: Homo sapiens

<400> SEQUENCE: 39

```
Gly Thr Trp Asp Ser Ser Leu Ser Ala Val
1               5                   10
```

<210> SEQ ID NO 40
<211> LENGTH: 110
<212> TYPE: PRT
<213> ORGANISM: Homo sapiens

<400> SEQUENCE: 40

```
Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asn
            20                  25                  30
```

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Phe Gly Gly Gly Thr Lys Leu Thr Val Leu Gly
            100                 105                 110

<210> SEQ ID NO 41
<211> LENGTH: 5
<212> TYPE: PRT
<213> ORGANISM: Homo sapiens

<400> SEQUENCE: 41

Ser Tyr Gly Met His
1               5

<210> SEQ ID NO 42
<211> LENGTH: 17
<212> TYPE: PRT
<213> ORGANISM: Homo sapiens

<400> SEQUENCE: 42

Val Ile Ser Tyr Pro Gly Thr Asn Glu Tyr Tyr Thr Asp Ser Val Lys
1               5                  10                  15

Gly

<210> SEQ ID NO 43
<211> LENGTH: 18
<212> TYPE: PRT
<213> ORGANISM: Homo sapiens

<400> SEQUENCE: 43

Gly Asp Ile His Ser Gly Tyr Ser Phe Gly Gly Gly Asp Tyr Gly Leu
1               5                  10                  15

Asp Val

<210> SEQ ID NO 44
<211> LENGTH: 127
<212> TYPE: PRT
<213> ORGANISM: Homo sapiens

<400> SEQUENCE: 44

Glu Val Gln Leu Val Glu Ser Gly Gly Gly Val Val Gln Pro Gly Lys
1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Val Ile Ser Tyr Pro Gly Thr Asn Glu Tyr Tyr Thr Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Ile His Ser Gly Tyr Ser Phe Gly Gly Gly Asp Tyr

```
                  100                 105                 110
Gly Leu Asp Val Trp Gly Gln Gly Thr Thr Val Thr Val Ser Ser
            115                 120                 125

<210> SEQ ID NO 45
<211> LENGTH: 11
<212> TYPE: PRT
<213> ORGANISM: Homo sapiens

<400> SEQUENCE: 45

Arg Ala Ser Gln Ser Ile Ser Gly Trp Leu Ala
1               5                   10

<210> SEQ ID NO 46
<211> LENGTH: 8
<212> TYPE: PRT
<213> ORGANISM: Homo sapiens

<400> SEQUENCE: 46

Lys Ala Ser Ser Leu Glu Ser Gly
1               5

<210> SEQ ID NO 47
<211> LENGTH: 9
<212> TYPE: PRT
<213> ORGANISM: Homo sapiens

<400> SEQUENCE: 47

Gln Gln Tyr Asn Asn Phe Pro Trp Thr
1               5

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Met
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asn Phe Pro Trp
                85                  90                  95

Thr Phe Gly Gln Gly Thr Lys Val Glu Phe Lys
            100                 105

<210> SEQ ID NO 49
<211> LENGTH: 5
<212> TYPE: PRT
<213> ORGANISM: Homo sapiens

<400> SEQUENCE: 49

Ser Tyr Ala Ile Ser
1               5

<210> SEQ ID NO 50
```

```
<211> LENGTH: 17
<212> TYPE: PRT
<213> ORGANISM: Homo sapiens

<400> SEQUENCE: 50

Gly Ile Ile Pro Ile Phe Gly Thr Ala Asn Tyr Ala Gln Lys Phe Gln
1               5                   10                  15

Gly

<210> SEQ ID NO 51
<211> LENGTH: 27
<212> TYPE: PRT
<213> ORGANISM: Homo sapiens

<400> SEQUENCE: 51

Asp Pro Arg His Tyr Gly Ser Gly Ser Tyr Tyr Asn Phe Gly Trp Gly
1               5                   10                  15

Phe Ala His Lys Arg Asn Tyr Gly Met Asp Val
            20                  25

<210> SEQ ID NO 52
<211> LENGTH: 136
<212> TYPE: PRT
<213> ORGANISM: Homo sapiens

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Arg His Tyr Gly Ser Gly Ser Tyr Tyr Asn Phe Gly
            100                 105                 110

Trp Gly Phe Ala His Lys Arg Asn Tyr Gly Met Asp Val Trp Gly Gln
        115                 120                 125

Gly Thr Thr Val Thr Val Ser Ser
    130                 135

<210> SEQ ID NO 53
<211> LENGTH: 11
<212> TYPE: PRT
<213> ORGANISM: Homo sapiens

<400> SEQUENCE: 53

Gln Gly Asp Ser Leu Arg Ser Tyr Tyr Ala Ser
1               5                   10

<210> SEQ ID NO 54
<211> LENGTH: 8
<212> TYPE: PRT
<213> ORGANISM: Homo sapiens

<400> SEQUENCE: 54

Gly Lys Asn Asn Arg Pro Ser Gly
1               5
```

<210> SEQ ID NO 55
<211> LENGTH: 9
<212> TYPE: PRT
<213> ORGANISM: Homo sapiens

<400> SEQUENCE: 55

Asn Ser Arg Asp Tyr Asn Val Arg Val
1               5

<210> SEQ ID NO 56
<211> LENGTH: 107
<212> TYPE: PRT
<213> ORGANISM: Homo sapiens

<400> SEQUENCE: 56

Ser Ser Glu Leu Thr Gln Asp Pro Ala Val Ser Val Ala Leu Gly Gln
1               5                   10                  15

Arg Val Thr Ile Thr Cys Gln Gly Asp Ser Leu Arg Ser Tyr Tyr Ala
            20                  25                  30

Ser Trp Tyr Gln Gln Lys Ser Gly Gln Ala Pro Leu Leu Val Leu Tyr
        35                  40                  45

Gly Lys Asn Asn Arg Pro Ser Gly Ile Pro Asp Arg Phe Ser Gly Ser
    50                  55                  60

Phe Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Tyr Asn Val Arg Val
                85                  90                  95

Phe Gly Gly Gly Thr Lys Leu Thr Val Leu Ser
            100                 105

<210> SEQ ID NO 57
<211> LENGTH: 5
<212> TYPE: PRT
<213> ORGANISM: Homo sapiens

<400> SEQUENCE: 57

Ser Tyr Ala Met His
1               5

<210> SEQ ID NO 58
<211> LENGTH: 17
<212> TYPE: PRT
<213> ORGANISM: Homo sapiens

<400> SEQUENCE: 58

Val Ile Ser Tyr Asp Gly Ser Asn Lys Tyr Tyr Ala Asp Ser Val Lys
1               5                   10                  15

Gly

<210> SEQ ID NO 59
<211> LENGTH: 10
<212> TYPE: PRT
<213> ORGANISM: Homo sapiens

<400> SEQUENCE: 59

Ser Ser Asp Lys Arg Cys Leu Val Asp Tyr
1               5                   10

<210> SEQ ID NO 60
<211> LENGTH: 119

```
<212> TYPE: PRT
<213> ORGANISM: Homo sapiens

<400> SEQUENCE: 60

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Asp Lys Arg Cys Leu Val Asp Tyr Trp Gly Gln Gly
            100                 105                 110

Thr Leu Val Thr Val Ser Ser
        115

<210> SEQ ID NO 61
<211> LENGTH: 11
<212> TYPE: PRT
<213> ORGANISM: Homo sapiens

<400> SEQUENCE: 61

Arg Ala Ser Gln Gly Ile Asn Pro Phe Leu Ala
1               5                   10

<210> SEQ ID NO 62
<211> LENGTH: 8
<212> TYPE: PRT
<213> ORGANISM: Homo sapiens

<400> SEQUENCE: 62

Thr Ala Ser Arg Leu Gln Ser Gly
1               5

<210> SEQ ID NO 63
<211> LENGTH: 9
<212> TYPE: PRT
<213> ORGANISM: Homo sapiens

<400> SEQUENCE: 63

Leu Gln His Lys His Tyr Pro Trp Thr
1               5

<210> SEQ ID NO 64
<211> LENGTH: 107
<212> TYPE: PRT
<213> ORGANISM: Homo sapiens

<400> SEQUENCE: 64

Asp Ile Gln Met Thr Gln Ser Pro Ser Ala Val Ser Ala Ser Leu Gly
1               5                   10                  15

Asp Arg Val Thr Ile Thr Cys Arg Ala Ser Gln Gly Ile Asn Pro Phe
            20                  25                  30

Leu Ala Trp Phe Gln Gln Lys Pro Gly Lys Val Pro Glu Arg Leu Ile
        35                  40                  45

Tyr Thr Ala Ser Arg Leu Gln Ser Gly Val Pro Ser Arg Phe Ser Gly
```

```
                50                  55                  60
        Ser Gly Thr Gly Thr Glu Phe Asn Leu Thr Ile Ser Ser Leu His Pro
        65                  70                  75                  80

Glu Asp Phe Ala Thr Tyr Tyr Cys Leu Gln His Lys His Tyr Pro Trp
                            85                  90                  95

Thr Phe Gly Gln Gly Thr Lys Val Glu Arg Lys
                        100                 105

<210> SEQ ID NO 65
<211> LENGTH: 381
<212> TYPE: DNA
<213> ORGANISM: Homo sapiens

<400> SEQUENCE: 65
caggtacagc tgcagcagtc aggggctgag gtgaagaagc ctggggcctc agtgaaggtc    60
gcctgcaagg cttctagata caacttcagc gcctattaca tgcactgggt gcgacaggcc   120
cccggacaag ggcctgagtg gatgggctgg atcaaccctc acagtggtgt cacaacatat   180
gcacagaagt ttcagggcag ggtcaccatg accaggaca cgtccatcgg cacagcctac    240
atggagctga gtaggctgag atctgacgac acggccctgt attactgtgc gagagggttt   300
gggtcctctt gtagtgatac cagttgctcc ttcagcggtt tggacgtctg gggccaaggg   360
accacggtca ccgtctcgag c                                              381

<210> SEQ ID NO 66
<211> LENGTH: 333
<212> TYPE: DNA
<213> ORGANISM: Homo sapiens

<400> SEQUENCE: 66
cagtctgccc tgactcagcc tgcctccgtg tctgggtctc ctggacagtc gatcaccatc    60
tcctgcactg gaaccagcag tgacgttggt ggttatgact atgtctcctg gtaccaacaa   120
cacccaggcg aagcccccaa gctcctcatt tatgatgtta ctaatcggcc ctcaggggtt   180
tctagtcgct tctctggctc caagtctggc aacacggcct ccctgaccat ctctggactc   240
cagcctgagg acgaggctga ttattactgc acctcatata caagcagcgt cacttatgtc    300
ttcggatctg ggaccacact caccgtccta agt                                 333

<210> SEQ ID NO 67
<211> LENGTH: 381
<212> TYPE: DNA
<213> ORGANISM: Homo sapiens

<400> SEQUENCE: 67
caggtgcagc tggtgcagtc tggggctgag gtgaagaagc ctggggcctc agtgaaggtc    60
gcctgcaagg cttctagata caacttcagc gcctattaca tgcactgggt gcgacaggcc   120
cccggacaag ggcctgagtg gatgggctgg atcaaccctc acagtggtgt cacaacatat   180
gcacggaagt ttcagggcag ggtcaccatg accaggaca cgtccatcgg cacagcctac    240
atggagctga gtaggctgag atctgacgac acggccctgt attactgtgc gagagggttt   300
gggtcctctt gtagtgatac cagttgctcc ttcagcggtt tggacgtctg gggccaaggg   360
accacggtca ccgtctcgag c                                              381

<210> SEQ ID NO 68
<211> LENGTH: 327
<212> TYPE: DNA
<213> ORGANISM: Homo sapiens
```

<400> SEQUENCE: 68

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacccct gtacactttt     300
ggccagggga ccaagctgga gatcaaa                                         327
```

<210> SEQ ID NO 69
<211> LENGTH: 381
<212> TYPE: DNA
<213> ORGANISM: Homo sapiens

<400> SEQUENCE: 69

```
caggtgcagc tggtgcagtc tggggctgag gtgaggaagc ctggggcctc agtgaaggtc      60
tcctgcaagg cttctagata tagcttcacc gcctactata tgcactgggt gcgacaggcc     120
cctggacaag gcttgagtg gatgggttgg atcaaccctc acagtggtgg cacaaattat     180
gcacagaagt ttcagggcag ggtcaccatg accaggaca cgtccaccag cacagcctac      240
atggagttga gcagtctgag atctgacgac acggccgtct tttactgtgc gagaggattt     300
gggtcctctt gtactagtac cagctgccag ttcagcggtt tggacgtctg ggccaaggg      360
accacggtca ccgtctcgag c                                               381
```

<210> SEQ ID NO 70
<211> LENGTH: 336
<212> TYPE: DNA
<213> ORGANISM: Homo sapiens

<400> SEQUENCE: 70

```
cagtctgccc tgactcagcc tgcctccgcg tccgggtctc ctggacagtc agtcaccatc      60
tcctgcactg gaaccagcag tgacgttggt ggttataact atgtctcctg gtaccaacag     120
cacccaggca aagcccccaa actcatgatt tatgaggtca ctaagcggcc ctcaggggtc     180
cctgatcgct tctctggctc caagtctggc aacacggcct ccctgaccgt ctctgggctc     240
caggctgagg atgaggctga ttattactgc agctcatatg caggcacaaa caatttgggg     300
gtcttcggaa ctgggaccaa ggtcaccgtc ctaggt                               336
```

<210> SEQ ID NO 71
<211> LENGTH: 372
<212> TYPE: DNA
<213> ORGANISM: Homo sapiens

<400> SEQUENCE: 71

```
gaggtgcagc tggtggagtc tggtcctacg ctggtgaaac ccacacagac cctcacgctg      60
acctgcacct tctctgggtt ctcactcaga actagtggag tggctgtggg ctggatccgt     120
cagccccag gaaaggccct ggagtggctt gcactcattt attgggatga tgataagcgc      180
tacagcccct ctctgaagag caggcttacc atcaccaagg acacctccaa aaaccaggtg     240
gtccttacaa tgaccaacat ggaccctgtg gacacagcca catattactg tgcacacaat     300
accggaacgg atttatattt tgactgggca tttgactact ggggccaggg aaccctggtc     360
accgtctcga gc                                                         372
```

```
<210> SEQ ID NO 72
<211> LENGTH: 336
<212> TYPE: DNA
<213> ORGANISM: Homo sapiens

<400> SEQUENCE: 72
cagtctgtgt tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcagggGtc     180
cctgaccgat tctctggctc caagtctggc acctcagcct ccctggccat cactgggctc     240
caggctgagg atgaggctga ttattactgc cagtcctatg acagcagcct gagtggttcg     300
gtgttcggcg agggaccaa gctgaccgtc ctaggt                                 336

<210> SEQ ID NO 73
<211> LENGTH: 372
<212> TYPE: DNA
<213> ORGANISM: Homo sapiens

<400> SEQUENCE: 73
cagatcacct tgaaggagtc tggtcctact ctggtgaaac ccacacagac cctcacgctg      60
acctgcacct ctctctggatt ctcactcaga actagtggcg tgggtgtggg ctggatccgt    120
cagcccccag gaaaggcccc ggagtggctt gcactcattt attgggatgg tgataagcgg    180
ttcagcccat ctctgaagag caggctcacc atcaacaagg acatctccaa aaaccaggtg    240
gtcctcacat tgaccaactt ggaccccgta gacacaggca catattactg tgcacacagt    300
ttttatcatg gttcgcaaag tcccggctgg ttcgacccct ggggccaggg aaccctggtc    360
accgtctcga gc                                                          372

<210> SEQ ID NO 74
<211> LENGTH: 330
<212> TYPE: DNA
<213> ORGANISM: Homo sapiens

<400> SEQUENCE: 74
cagtctgtgt tgacgcagcc gccctcagtg tctgcggccc caggacagaa ggtcaccatc      60
tcctgctctg gaagcagctc caacattggg aataattatg tatcctggta ccagcagctc    120
ccaggaacag cccccaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggata gcagcctgag tgctgtattc    300
ggcggaggga ccaagctgac cgtcctaggt                                      330

<210> SEQ ID NO 75
<211> LENGTH: 381
<212> TYPE: DNA
<213> ORGANISM: Homo sapiens

<400> SEQUENCE: 75
gaggtgcagc tggtggagtc tgggggaggc gtggtccagc ctgggaagtc cctgagactc      60
tcctgtgcag cgtctggatt caccttcagt agttatggca tgcactgggt ccgccaggct    120
ccaggcaagg ggctggagtg gtggcagtt atatcttatc ctggaactaa tgaatattat     180
acagactctg tgaagggccg attcaccatc tccagagaca attccaagaa cacgctgtat    240
ctgcaaatga acagcctgag agccgaggac acggctgtgt attactgtgc gagagggac    300 atccatagcg gttattcctt tgggggcggg gactacggtt tggacgtctg gggccaaggg    360
```

```
accacggtca ccgtctcgag c                                              381

<210> SEQ ID NO 76
<211> LENGTH: 321
<212> TYPE: DNA
<213> ORGANISM: Homo sapiens

<400> SEQUENCE: 76
gacatccaga tgacccagtc tccttccacc ctgtctgcat ctgttggaga cagagtcacc     60
atcacttgcc gggccagtca gagtattagt ggctggttgg cctggtatca gcagaaacca    120
gggaaagccc caaagctcct gatgtataag gcctccagtt tagaaagtgg ggtcccatca    180
agattcagcg gcagtggatc tgggacagaa ttcactctca ccatcagtag cctgcagcct    240
gatgattttg caacttatta ctgccaacag tataataatt cccgtggac gttcggccaa     300 gggaccaagg tggaattcaa a                                              321

<210> SEQ ID NO 77
<211> LENGTH: 408
<212> TYPE: DNA
<213> ORGANISM: Homo sapiens

<400> SEQUENCE: 77
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagacccc    300
cggcactatg gttcggggag ttattataac ttcggttggg ggttcgccca caaaagaaac    360
tacggtatgg acgtctgggg ccaagggacc acggtcaccg tctcgagc                 408

<210> SEQ ID NO 78
<211> LENGTH: 321
<212> TYPE: DNA
<213> ORGANISM: Homo sapiens

<400> SEQUENCE: 78
tcttctgagc tgactcagga ccctgctgtg tctgtggcct tgggcagag agtcacgatc     60 acatgccaag agacagtct cagaagctac tatgcaagct ggtatcagca gaagtcagga    120
caggcccctc tacttgtcct ctatggtaaa acaatcgcc cctcagggat cccagaccga    180
ttctctggct ccttctcagg aaatacagct tccttgacca tcaccggggc tcaggcggaa    240
gacgaggctg actattattg taattcccga gactacaatg tcagagtttt cggcggaggg    300
accaagctga ccgtcctaag t                                              321

<210> SEQ ID NO 79
<211> LENGTH: 357
<212> TYPE: DNA
<213> ORGANISM: Homo sapiens

<400> SEQUENCE: 79
gaggtgcagc tggtggagtc tgggggaggc gtggtccagc ctgggaggtc cctgagactc     60
tcctgtgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
```

```
ctgcaaatga acagcctgag agctgaggac acggctgtgt attactgtgc gagaagttcc    300
gacaaacggt gcctggttga ctactggggc cagggaaccc tggtcaccgt ctcgagc       357
```

<210> SEQ ID NO 80
<211> LENGTH: 321
<212> TYPE: DNA
<213> ORGANISM: Homo sapiens

<400> SEQUENCE: 80

```
gacatccaga tgacccagtc tccatctgcc gtgtctgcgt ctctaggaga cagagtcacc    60
atcacttgtc gggcgagtca gggcattaac ccttttttag cctggtttca gcagaaacca    120
ggcaaagtcc ctgagcgcct gatctatact gcatccagat tgcaaagtgg agtcccatcc    180
aggttcagcg gcagtggtac tgggacagaa ttcaatctca caatcagcag cctgcaccct    240
gaagactttg caacttatta ctgtcttcaa cataaacatt acccgtggac gttcggccaa    300
gggaccaagg tggaaaggaa a                                               321
```

<210> SEQ ID NO 81
<211> LENGTH: 56
<212> TYPE: DNA
<213> ORGANISM: Artificial Sequence
<220> FEATURE:
<223> OTHER INFORMATION: primer

<400> SEQUENCE: 81

```
gtcctcgcaa ctgcggccca gccggccatg gcccaggtgc agctggtgca gtctgg        56
```

<210> SEQ ID NO 82
<211> LENGTH: 56
<212> TYPE: DNA
<213> ORGANISM: Artificial Sequence
<220> FEATURE:
<223> OTHER INFORMATION: primer

<400> SEQUENCE: 82

```
gtcctcgcaa ctgcggccca gccggccatg gcccaggtca acttaaggga gtctgg        56
```

<210> SEQ ID NO 83
<211> LENGTH: 56
<212> TYPE: DNA
<213> ORGANISM: Artificial Sequence
<220> FEATURE:
<223> OTHER INFORMATION: primer

<400> SEQUENCE: 83

```
gtcctcgcaa ctgcggccca gccggccatg gccgaggtgc agctggtgga gtctgg        56
```

<210> SEQ ID NO 84
<211> LENGTH: 56
<212> TYPE: DNA
<213> ORGANISM: Artificial Sequence
<220> FEATURE:
<223> OTHER INFORMATION: primer

<400> SEQUENCE: 84

```
gtcctcgcaa ctgcggccca gccggccatg gcccaggtgc agctgcagga gtcggg        56
```

<210> SEQ ID NO 85
<211> LENGTH: 56
<212> TYPE: DNA
<213> ORGANISM: Artificial Sequence
<220> FEATURE:
<223> OTHER INFORMATION: primer -continued

```
<400> SEQUENCE: 85
gtcctcgcaa ctgcggccca gccggccatg gcccaggtgc agctgttgca gtctgc          56

<210> SEQ ID NO 86
<211> LENGTH: 56
<212> TYPE: DNA
<213> ORGANISM: Artificial Sequence
<220> FEATURE:
<223> OTHER INFORMATION: primer

<400> SEQUENCE: 86
gtcctcgcaa ctgcggccca gccggccatg gcccaggtac agctgcagca gtcagg          56

<210> SEQ ID NO 87
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (37)..(37)
<223> OTHER INFORMATION: n is a or g

<400> SEQUENCE: 87
gtcctcgcaa ctgcggccca gccggccatg gcccagntca ccttgaagga gtctggtcc      59

<210> SEQ ID NO 88
<211> LENGTH: 56
<212> TYPE: DNA
<213> ORGANISM: Artificial Sequence
<220> FEATURE:
<223> OTHER INFORMATION: primer

<400> SEQUENCE: 88
gtcctcgcaa ctgcggccca gccggccatg gcccaggtgc agctacagca gtgggg          56

<210> SEQ ID NO 89
<211> LENGTH: 56
<212> TYPE: DNA
<213> ORGANISM: Artificial Sequence
<220> FEATURE:
<223> OTHER INFORMATION: primer

<400> SEQUENCE: 89
gtcctcgcaa ctgcggccca gccggccatg gccgaggtgc agctggtgca gtctgg          56

<210> SEQ ID NO 90
<211> LENGTH: 64
<212> TYPE: DNA
<213> ORGANISM: Artificial Sequence
<220> FEATURE:
<223> OTHER INFORMATION: primer

<400> SEQUENCE: 90
gtcctcgcaa ctgcggccca gccggccatg gcccaggtgc agctggtgca atctgggtct     60
gagt                                                                   64

<210> SEQ ID NO 91
<211> LENGTH: 32
<212> TYPE: DNA
<213> ORGANISM: Artificial Sequence
<220> FEATURE:
<223> OTHER INFORMATION: primer

<400> SEQUENCE: 91
```
ggtggaggca ctcgagacgg tgaccagggt gc        32

<210> SEQ ID NO 92
<211> LENGTH: 32
<212> TYPE: DNA
<213> ORGANISM: Artificial Sequence
<220> FEATURE:
<223> OTHER INFORMATION: primer

<400> SEQUENCE: 92
ggtggaggca ctcgagacgg tgaccattgt cc        32

<210> SEQ ID NO 93
<211> LENGTH: 32
<212> TYPE: DNA
<213> ORGANISM: Artificial Sequence
<220> FEATURE:
<223> OTHER INFORMATION: primer

<400> SEQUENCE: 93
ggtggaggca ctcgagacgg tgaccagggt tc        32

<210> SEQ ID NO 94
<211> LENGTH: 32
<212> TYPE: DNA
<213> ORGANISM: Artificial Sequence
<220> FEATURE:
<223> OTHER INFORMATION: primer

<400> SEQUENCE: 94
ggtggaggca ctcgagacgg tgaccgtggt cc        32

<210> SEQ ID NO 95
<211> LENGTH: 56
<212> TYPE: DNA
<213> ORGANISM: Artificial Sequence
<220> FEATURE:
<223> OTHER INFORMATION: primer

<400> SEQUENCE: 95
gtcctcgcaa ctgcggccca gccggccatg gccgacatcc agatgaccca gtctcc        56

<210> SEQ ID NO 96
<211> LENGTH: 56
<212> TYPE: DNA
<213> ORGANISM: Artificial Sequence
<220> FEATURE:
<223> OTHER INFORMATION: primer

<400> SEQUENCE: 96
gtcctcgcaa ctgcggccca gccggccatg gccgatgttg tgatgactca gtctcc        56

<210> SEQ ID NO 97
<211> LENGTH: 56
<212> TYPE: DNA
<213> ORGANISM: Artificial Sequence
<220> FEATURE:
<223> OTHER INFORMATION: primer

<400> SEQUENCE: 97
gtcctcgcaa ctgcggccca gccggccatg gccgaaattg tgttgacgca gtctcc        56

<210> SEQ ID NO 98
<211> LENGTH: 56
<212> TYPE: DNA
<213> ORGANISM: Artificial Sequence

```
<220> FEATURE:
<223> OTHER INFORMATION: primer

<400> SEQUENCE: 98
gtcctcgcaa ctgcggccca gccggccatg gccgacatcg tgatgaccca gtctcc      56

<210> SEQ ID NO 99
<211> LENGTH: 56
<212> TYPE: DNA
<213> ORGANISM: Artificial Sequence
<220> FEATURE:
<223> OTHER INFORMATION: primer

<400> SEQUENCE: 99
gtcctcgcaa ctgcggccca gccggccatg gccgaaacga cactcacgca gtctcc      56

<210> SEQ ID NO 100
<211> LENGTH: 56
<212> TYPE: DNA
<213> ORGANISM: Artificial Sequence
<220> FEATURE:
<223> OTHER INFORMATION: primer

<400> SEQUENCE: 100
gtcctcgcaa ctgcggccca gccggccatg gccgaaattg tgctgactca gtctcc      56

<210> SEQ ID NO 101
<211> LENGTH: 56
<212> TYPE: DNA
<213> ORGANISM: Artificial Sequence
<220> FEATURE:
<223> OTHER INFORMATION: primer

<400> SEQUENCE: 101
gtcctcgcaa ctgcggccca gccggccatg gcccagtctg tgttgacgca gccgcc      56

<210> SEQ ID NO 102
<211> LENGTH: 56
<212> TYPE: DNA
<213> ORGANISM: Artificial Sequence
<220> FEATURE:
<223> OTHER INFORMATION: primer

<400> SEQUENCE: 102
gtcctcgcaa ctgcggccca gccggccatg gcccagtctg ccctgactca gcctgc      56

<210> SEQ ID NO 103
<211> LENGTH: 56
<212> TYPE: DNA
<213> ORGANISM: Artificial Sequence
<220> FEATURE:
<223> OTHER INFORMATION: primer

<400> SEQUENCE: 103
gtcctcgcaa ctgcggccca gccggccatg gcctcctatg tgctgactca gccacc      56

<210> SEQ ID NO 104
<211> LENGTH: 56
<212> TYPE: DNA
<213> ORGANISM: Artificial Sequence
<220> FEATURE:
<223> OTHER INFORMATION: primer

<400> SEQUENCE: 104
gtcctcgcaa ctgcggccca gccggccatg gcctcttctg agctgactca ggaccc      56
```

```
<210> SEQ ID NO 105
<211> LENGTH: 56
<212> TYPE: DNA
<213> ORGANISM: Artificial Sequence
<220> FEATURE:
<223> OTHER INFORMATION: primer

<400> SEQUENCE: 105
gtcctcgcaa ctgcggccca gccggccatg gcccacgtta tactgactca accgcc        56

<210> SEQ ID NO 106
<211> LENGTH: 56
<212> TYPE: DNA
<213> ORGANISM: Artificial Sequence
<220> FEATURE:
<223> OTHER INFORMATION: primer

<400> SEQUENCE: 106
gtcctcgcaa ctgcggccca gccggccatg gcccaggctg tgctcactca gccgcc        56

<210> SEQ ID NO 107
<211> LENGTH: 56
<212> TYPE: DNA
<213> ORGANISM: Artificial Sequence
<220> FEATURE:
<223> OTHER INFORMATION: primer

<400> SEQUENCE: 107
gtcctcgcaa ctgcggccca gccggccatg gccaatttta tgctgactca gcccca        56

<210> SEQ ID NO 108
<211> LENGTH: 44
<212> TYPE: DNA
<213> ORGANISM: Artificial Sequence
<220> FEATURE:
<223> OTHER INFORMATION: primer

<400> SEQUENCE: 108
tcgactggcg cgccgaacac tctcccctgt tgaagctctt tgtg                     44

<210> SEQ ID NO 109
<211> LENGTH: 43
<212> TYPE: DNA
<213> ORGANISM: Artificial Sequence
<220> FEATURE:
<223> OTHER INFORMATION: primer

<400> SEQUENCE: 109
tcgactggcg cgccgaacat tctgtagggg ccactgtctt ctc                      43
```